United States Patent
Finlay

(10) Patent No.: US 12,415,861 B2
(45) Date of Patent: Sep. 16, 2025

(54) ANTI C-MET ANTIBODIES

(71) Applicant: CENTESSA PHARMACEUTICALS (UK) LIMITED, Altrincham (GB)

(72) Inventor: William James Jonathan Finlay, Glasgow (GB)

(73) Assignee: CENTESSA PHARMACEUTICALS (UK) LIMITED, Altrincham (GB)

( * ) Notice: Subject to any disclaimer, the term of this patent is extended or adjusted under 35 U.S.C. 154(b) by 38 days.

(21) Appl. No.: 18/304,598

(22) Filed: Apr. 21, 2023

(65) Prior Publication Data

US 2023/0295311 A1    Sep. 21, 2023

Related U.S. Application Data

(63) Continuation of application No. 16/980,015, filed as application No. PCT/EP2019/056178 on Mar. 12, 2019, now Pat. No. 11,673,960.

(30) Foreign Application Priority Data

| Mar. 12, 2018 | (GB) | ..................................... | 1803892 |
| Jul. 31, 2018 | (GB) | ..................................... | 1812487 |
| Oct. 16, 2018 | (GB) | ..................................... | 1816841 |

(51) Int. Cl.
*C07K 16/28* (2006.01)

(52) U.S. Cl.
CPC ...... *C07K 16/2863* (2013.01); *C07K 2317/31* (2013.01); *C07K 2317/52* (2013.01); *C07K 2317/565* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 11,673,960 B2 | 6/2023 | Finlay |
| 2010/0129369 A1 | 5/2010 | Davies et al. |
| 2011/0239316 A1 | 9/2011 | Goetsch et al. |
| 2015/0118238 A1 | 4/2015 | Beuerlein et al. |
| 2021/0009694 A1 | 1/2021 | Finlay |

FOREIGN PATENT DOCUMENTS

| CN | 1889979 A | 1/2007 |
| JP | 2011501945 A | 1/2011 |
| JP | 2012509881 A | 4/2012 |
| JP | 2012510280 A | 5/2012 |
| JP | 2012530514 A | 12/2012 |
| JP | 2014533247 A | 12/2014 |
| JP | 2015511629 A | 4/2015 |
| JP | 2015519335 A | 7/2015 |
| JP | 2017043622 A | 3/2017 |
| JP | 2017507962 A | 3/2017 |
| WO | WO-2010069765 A1 | 6/2010 |
| WO | WO-2013169532 A1 | 11/2013 |
| WO | WO-2019175186 A1 | 9/2019 |

OTHER PUBLICATIONS

Luyue, Bai, et al., Preparation of Human Whole-Molecule Anti-C-Met Antibodies and Their Biological Properties on Nasopharyngeal Carcinoma Cells Impact. Journal of Nanjing Medical University (Natural Science Edition) 36(6):687-692 (2016).
U.S. Appl. No. 16/980,015 Corrected Notice of Allowability dated Mar. 16, 2023.
U.S. Appl. No. 16/980,015 Non-Final Office Action dated Jun. 13, 2022.
U.S. Appl. No. 16/980,015 Notice of Allowance dated Jan. 25, 2023.
Zhenfang, Xiong, et al., C-Met as a Tumor Treatment Characteristics of Targets and Their Inhibitors Application Prospects. Guangdong Medical Journal 35(22): 4 Pages (2014).
International Search Report and Written Opinion mailed Jun. 18, 2019 for International Application No. PCT/EP2019/056178, 14 pages.
Townsend, S. et al., "Augmented Binary Substitution: Single-pass CDR germlining and stabilization of therapeutic antibodies," PNAS, 112(50):15354-15359 (2015).

*Primary Examiner* — Marianne P Allen
(74) *Attorney, Agent, or Firm* — WILSON SONSINI GOODRICH & ROSATI

(57) ABSTRACT

Provided herein are antibody molecules that bind specifically to C-MET and related nucleic acid molecules, vectors and host cells. Also provided herein are medical uses of such antibody molecules.

19 Claims, 21 Drawing Sheets

Specification includes a Sequence Listing.

ANTI C-MET ANTIBODIES

CROSS-REFERENCE TO RELATED APPLICATIONS

This application is a continuation of U.S. patent application Ser. No. 16/980,015, filed Sep. 11, 2020, which is a 35 U.S.C. § 371 national phase application of International Patent Application No. PCT/EP2019/056178, filed on Mar. 12, 2019, which claims the benefit of GB Patent Application No. 1816841.9, filed on Oct. 16, 2018, GB Patent Application No. 1812487.5, filed on Jul. 31, 2018, and GB Patent Application No. 1803892.7, filed on Mar. 12, 2018, the disclosure of each of which is hereby incorporated by reference in its entirety.

DESCRIPTION OF THE TEXT FILE SUBMITTED ELECTRONICALLY

The contents of the electronic sequence listing (ULSL_001_04US_SeqList_ST26.xml; Size: 338,625 bytes; and Date of Creation: Apr. 17, 2023) are herein incorporated by reference in their entirety.

FIELD OF THE INVENTION

The invention relates to antibody molecules binding specifically to C-MET (also known as MET, MET proto-oncogene, receptor tyrosine kinase, AUTS9, HGFR, RCCP2, DFNB97, OSFD) and medical uses thereof.

BACKGROUND OF THE INVENTION

C-MET (also known as MET, MET proto-oncogene, receptor tyrosine kinase, AUTS9, HGFR, RCCP2, DFNB97, OSFD) is a transmembrane protein that belongs to the immunoglobulin superfamily and binds to the soluble factor HGF (hepatocyte growth factor), which is principally produced by mesenchymal cells. C-MET is a single-pass receptor tyrosine kinase that is expressed as a primary single chain precursor protein that is then post-translationally cleaved to produce alpha and beta subunits, which are disulfide linked to form the mature receptor. C-MET is mainly expressed by epithelial cells and has also been observed on multiple other cell types, such as endothelial cells, neurons, hepatocytes, hematopoietic cells, melanocytes and neonatal cardiomyocytes. On binding to HGF, this receptor dimerises, activating its tyrosine kinase activity. This kinase activation leads to further downstream activation of signal transduction molecules that play known roles in cell survival, proliferation, and differentiation.

Genetic amplification and/or overexpression of C-MET is strongly associated with the progression of several important types of cancer, such as Non-Small Cell Lung (NSCLC), Gastric cancer, Pancreatic cancer, Uveal Melanoma, and Papillary Renal Cell Carcinoma. Preclinical and clinical evidence suggests that blocking C-MET/HGF signalling can have clear therapeutic benefit in multiple cancers, but this has predominantly been achieved using small molecule inhibitors of C-MET kinase function. Resistance mutations commonly develop after tyrosine kinase inhibitor treatment, causing therapeutic efficacy to be lost. Therapeutic antibodies that antagonise C-MET signalling by blocking the ability of the receptors to dimerise have the potential to mediate anti-tumour effects via two mechanisms: 1. Potent inhibition of the MET signalling pathway by locking the receptors into a non-activating monomeric form. 2. Antibody effector-function mediated engagement of immune cells.

The majority of currently approved antibody therapeutics are derived from immunized rodents. Many of those antibodies have undergone a process known as "humanization", via the "grafting" of murine Complementarity-Determining Regions (CDRs) into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. Antibodies such as anti-C-MET, which potentially engage immune effector functions as part of their mechanism of action, are at particularly high risk of immunogenicity as they can encourage phagocytosis of C-MET+ target cells, leading to antigen processing of the antibody along with the target cell. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized antagonistic anti-C-MET antibody would therefore have as many residues as possible in the v-domains that are identical to those found in both the frameworks and CDRs of well-characterized human germline sequences. This high level of identity to high-stability germlines that are highly expressed in the maximum number of potential patients minimises the risk of a therapeutic antibody having unwanted immunogenicity in the clinic, or unusually high 'cost of goods' in manufacturing.

Townsend et al. (2015; PNAS 112: 15354-15359) describe a method for generating antibodies in which CDRs derived from rat, rabbit and mouse antibodies were grafted into preferred human frameworks and then subject to a human germ-lining approach termed "Augmented Binary Substitution". Although the approach demonstrated a fundamental plasticity in the original antibody paratopes, in the absence of highly accurate antibody-antigen co-crystal structural data, it is still not possible to reliably predict which individual residues in the CDR loops of any given antibody can be converted to human germline, and in what combination. Additionally, the Townsend et al. study did not address the addition of mutagenesis beyond the residues found in the human germline at positions where the removal of development risk motifs might be beneficial. This is a technological limitation which renders the process inherently inefficient, requiring an extra stage of modification of the starting antibody sequence. In addition, it cannot currently be accurately predicted what modifications in distal positions of the protein sequence of an individual v-domain, or even on the partner v-domain, might facilitate the removal of risk motifs while maintaining antigen binding affinity and specificity.

CDR germ-lining and development quality optimisation is thus a complex, multifactorial problem, as multiple functional properties of the molecule should preferably be maintained, including in this instance: target binding specificity, affinity to C-MET from both human and animal test species (e.g. cynomolgus monkey, also known as the crab-eating macaque, i.e. Macaca fascicularis), v-domain biophysical stability and/or IgG yield from protein expression platforms used in research, clinical and commercial supply. Antibody engineering studies have shown that mutation of even single residue positions in key CDRs can have dramatic effects on all of these desired molecular properties.

WO2011151412A1 describes an antagonistic murine anti-C-MET IgG molecule termed "224G11", and also the preparation of humanized forms (h224G11). Those humanized forms of 224G11 were produced using classical humanization techniques, i.e. by grafting of Kabat-defined murine CDRs into human heavy and light chain framework sequences, with some of the human framework residues being potentially back-mutated to the correspondingly positioned 224G11 murine residues. For reasons noted above, such humanized forms of 224G11 described in WO2011151412A1 are not ideal.

SUMMARY OF THE INVENTION

The present invention provides a number of anti-C-MET antibodies and medical uses thereof.

According to one aspect of the invention, there is provided an antibody molecule which specifically binds to human C-MET, and optionally also to cynomolgus monkey C-MET, or an antigen-binding portion thereof, wherein the antibody molecule or antigen-binding portion comprises a heavy chain variable region with:

an HCDR1 having amino acids in sequence in the following order: G-Y-I or any amino acid (such as T)-F-T-A or any amino acid (such as S)-Y-Y or any amino acid (such as A, S or T)-M-H (SEQ ID NO: 22);

an HCDR2 having amino acids in sequence in the following order: M-G-W or any amino acid (such as I)-I-K or any amino acid (such as N)-P-N or any amino acid (such as S)-N or any amino acid (such as G)-G-L or any amino acid (such as S)-A or any amino acid (such as T)-N or any amino acid (such as S)-Y-A-Q-K-F-Q-G (SEQ ID NO: 23); and an HCDR3 having amino acids in sequence in the following order: S or any amino acid (such as A/E/H/M/Q/TV)-E-I-T-T-E or any amino acid (such as D)-F or any amino acid (such as L)-D-Y or any amino acid (such as A/E/F/I/K/L/M/Q/SN/VW) (SEQ ID NO: 24).

In aspects of the invention, the HCDR1 of the antibody molecule or antigen-binding portion may exclude the sequence GYIFTAYTMH (SEQ ID NO: 25; 224G11 murine/humanized antibody HCDR1 disclosed in WO2011151412A1; US 2013/0216527A1), the HCDR2 of the antibody molecule or antigen-binding portion may exclude the sequence MGWIKPNNGLANYAQKFQG (SEQ ID NO: 26; 224G11 murine/humanized antibody HCDR1 disclosed in WO2011151412A1; US 2013/0216527A1), and/or the HCDR3 of the antibody molecule or antigen-binding portion may exclude the sequence SEITTEFDY (SEQ ID NO: 27; 224G11 murine/humanized antibody HCDR3 disclosed in WO2011151412A1; US 2013/0216527A1).

The antibody molecule or antigen-binding portion may further comprise a light chain variable region with:

an LCDR1 having amino acids in sequence in the following order: R-A-S-Q-S-V-D or any amino acid (for example, S or E)-S-Y-A-N or any amino acid (for example, Q)-S-F or any amino acid (for example, Y)-L-H or any amino acid (for example, A) (SEQ ID NO: 28);

an LCDR2 having amino acids in sequence in the following order: R or any amino acid (for example, A)-A or any amino acid (for example, G)-S-T or any amino acid (for example, S)-R-E-S or any amino acid (for example, T); and an LCDR3 having amino acids in sequence in the following order: Q-Q-S or any amino acid (for example, Y)-K or any amino acid (for example, G)-E or any amino acid (for example, D, S)-D or any amino acid (for example, S, E, R)-P-L-T (SEQ ID NO: 30).

In aspects of the invention, the LCDR1 of the antibody molecule or antigen-binding portion may exclude the sequence KSSESVDSYANSFLH (SEQ ID NO: 31; 224G11 murine/humanized antibody LCDR1 disclosed in WO2011151412A1; US 2013/0216527A1), and/or the LCDR2 of the antibody molecule or antigen-binding portion may exclude the sequence RASTRES (SEQ ID NO: 32; 224G11 murine/humanized antibody LCDR2 disclosed in WO2011151412A1; US 2013/0216527A1), and/or the LCDR3 of the antibody molecule or antigen-binding portion may exclude the sequence QQSKEDPLT (SEQ ID NO: 33; 224G11 murine/humanized antibody LCDR3 disclosed in WO2011151412A1; US 2013/0216527A1).

In some aspects, disclosed herein is an anti-C-MET antibody or an antigen-binding portion thereof, wherein the antibody comprises a heavy chain variable (VH) region and a light chain variable (VL) region, wherein (a) the HCDR1 comprises the amino acid sequence G-Y-$X_1$-F-T-$X_2$-Y-$X_3$-M-H, wherein $X_1$ is I or any other amino acid, $X_2$ is A or any other amino acid and $X_3$ is Y or any other amino acid (SEQ ID NO: 22);

(b) the HCDR2 comprises M-G-$X_1$-I-$X_2$-P-$X_3$-$X_4$-G-$X_5$-$X_6$-$X_7$-Y-A-Q-K-F-Q-G, wherein $X_1$ is W or any other amino acid, $X_2$ is K or any other amino acid, $X_3$ is N or any other amino acid, $X_4$ is N or any other amino acid, $X_5$ is L or any other amino acid, $X_6$ is A or any other amino acid and $X_7$ is N or any other amino acid (SEQ ID NO: 23);

(c) the HCDR3 comprises $X_1$-E-I-T-T-$X_2$-$X_3$-D-$X_4$, wherein $X_1$ is S or any other amino acid, $X_2$ is E or any other amino acid, $X_3$ is F or any other amino acid and $X_4$ is Y or any other amino acid (SEQ ID NO: 24);

(d) the LCDR1 comprises R-A-S-Q-S-V-$X_1$-S-Y-A-$X_2$-S-$X_3$-L-$X_4$, wherein $X_1$ is D or any other amino acid, $X_2$ is N or any other amino acid, $X_3$ is F or any other amino acid of F and $X_4$ is H or any other amino acid (SEQ ID NO: 28);

(e) the LCDR2 comprises $X_1$-$X_2$-S-$X_3$-R-E-$X_4$, wherein $X_1$ is R or any other amino acid, $X_2$ is A or any other amino acid, $X_3$ is T or any other amino acid and $X_4$ is S or any other amino acid; and (f) the LCDR3 comprises Q-Q-$X_1$-$X_2$-$X_3$-$X_4$-P-L-T, wherein $X_1$ is S or any other amino acid, $X_2$ is K or any other amino acid, $X_3$ is E or any other amino acid and $X_4$ is D or any other amino acid (SEQ ID NO: 30).

In some aspects, the invention provides an anti-C-MET antibody or an antigen-binding portion thereof, wherein the antibody comprises a heavy chain variable (VH) region and a light chain variable (VL) region, wherein (a) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYAQSYLH (SEQ ID NO: 57), LCDR2 of RGSTRET (SEQ ID NO: 56) and LCDR3 of QQSKESPLT (SEQ ID NO: 47);

(b) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 47);

(c) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKSEPLT (SEQ ID NO: 39);

(d) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(e) the VH region amino acid sequence comprises HCDR1 of GYTFTSYTMH (SEQ ID NO: 34), HCDR2 of MGWINPSGGLANYAQKFQG (SEQ ID NO: 54) and HCDR3 of SEITTDFDY (SEQ ID NO: 55); and the VL region amino acid sequence comprises LCDR1 of RASQSVDSYANSYLH (SEQ ID NO: 51), LCDR2 of RGSTRES (LCDR2; SEQ ID NO: 38) and LCDR3 of QQSKSEPLT (SEQ ID NO: 39);

(f) the VH region amino acid sequence comprises HCDR1 of GYTFTSYTMH (SEQ ID NO: 34), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(g) the VH region amino acid sequence comprises HCDR1 of GYTFTSYAMH (SEQ ID NO: 41), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(h) the VH region amino acid sequence comprises HCDR1 of GYTFTSYTMH (SEQ ID NO: 34), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(i) the VH region amino acid sequence comprises HCDR1 of GYIFTSYSMH (SEQ ID NO: 43), HCDR2 of MGWINPSNGLANYAQKFQG (SEQ ID NO: 44) and HCDR3 of QEITTEFDI (SEQ ID NO: 45); and the VL region amino acid sequence comprises LCDR1 of RASQSVESYAQSYLH (SEQ ID NO: 46), LCDR2 of RGSTRES (SEQ ID NO: 38) and LCDR3 of QQSKSDPLT (SEQ ID NO: 76);

(j) the VH region amino acid sequence comprises HCDR1 of GYIFTSYTMH (SEQ ID NO: 48), HCDR2 of MGWINPNGGLASYAQKFQG (SEQ ID NO: 49) and HCDR3 of SEITTEQDY (SEQ ID NO: 50); and the VL region amino acid sequence comprises LCDR1 of RASQSVDSYANSYLH (SEQ ID NO: 51), LCDR2 of RGSTRES (SEQ ID NO: 38) and LCDR3 of QQSKESPLT (SEQ ID NO: 47); or (k) the VH region amino acid sequence comprises HCDR1 of GYIFTSYTMH (SEQ ID NO: 48), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVESYANSYLH (SEQ ID NO: 52), LCDR2 of RGSTRES (SEQ ID NO: 38) and LCDR3 of QQYGSEPLT (SEQ ID NO: 53).

In some aspects, disclosed herein is an anti-C-MET antibody or an antigen-binding portion thereof, wherein the antibody comprises a heavy chain variable (VH) region and a light chain variable (VL) region, wherein
the VH region amino acid sequence comprises:
(a) HCDR1 of SEQ ID NO: 34, SEQ ID NO: 41, SEQ ID NO: 43 or SEQ ID NO: 48;
(b) HCDR2 of SEQ ID NO: 35, SEQ ID NO: 40, SEQ ID NO: 42, SEQ ID NO: 44, SEQ ID NO: 49 or SEQ ID NO: 54; and
(c) HCDR3 of SEQ ID NO: 36, SEQ ID NO: 45, SEQ ID NO: 50 or SEQ ID NO: 55; and the VL region amino acid sequence comprises:
(a') LCDR1 of SEQ ID NO: 37, SEQ ID NO: 46, SEQ ID NO: 51, SEQ ID NO: 52 or SEQ ID NO: 57;
(b') LCDR2 of SEQ ID NO: 38 or SEQ ID NO: 56; and
(c') LCDR3 of SEQ ID NO: 39, SEQ ID NO: 47, SEQ ID NO: 53 or SEQ ID NO: 76.

In some aspects, disclosed herein is an anti-C-MET antibody or an antigen-binding portion thereof, wherein the antibody comprises a heavy chain variable (VH) region and a light chain variable (VL) region, wherein
(a) the VH region amino acid sequence comprises SEQ ID NO:1 and the VL region amino acid sequence comprises SEQ ID NO:2;
(b) the VH region amino acid sequence comprises SEQ ID NO:3 and the VL region amino acid sequence comprises SEQ ID NO:4;
(c) the VH region amino acid sequence comprises SEQ ID NO:5 and the VL region amino acid sequence comprises SEQ ID NO:6;
(d) the VH region amino acid sequence comprises SEQ ID NO:7 and the VL region amino acid sequence comprises SEQ ID NO:8; or
(e) the VH region amino acid sequence comprises SEQ ID NO:9 and the VL region amino acid sequence comprises SEQ ID NO:10.

Also provided according to the invention is an immunoconjugate comprising the antibody molecule or antigen-binding portion thereof as defined herein linked, fused or conjugated to a therapeutic agent.

In another aspect the invention provides a nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-C-MET antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

Further provided herein is an antibody molecule or antigen-binding portion thereof as defined herein, or the immunoconjugate as defined herein, or the nucleic acid molecule as defined herein, or the vector as defined herein, or the pharmaceutical composition as defined herein, for use as a medicament. The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an autoimmune disease or an inflammatory disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

For example, the autoimmune disease or inflammatory disease may be arthritis, asthma, multiple sclerosis, psoriasis, Crohn's disease, inflammatory bowel disease, lupus, Grave's disease, Hashimoto's thyroiditis, or ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease, an inflammatory disease or a fibrotic disease.

The cardiovascular disease in any aspect of the invention may for example be coronary heart disease or atherosclerosis.

The fibrotic disease in any aspect of the invention may be selected from the group consisting of myocardial infarction, angina, osteoarthritis, pulmonary fibrosis, cystic fibrosis, bronchitis and asthma.

The invention also provides a method of producing an antibody molecule which specifically binds to human C-MET and optionally also to cynomolgus monkey C-MET, or an antigen-binding portion thereof, comprising the steps of:
(1) grafting anti-C-MET CDRs from a non-human source into a human v-domain framework to produce a humanized anti-C-MET antibody molecule or antigen-binding portion thereof;
(2) generating a phage library of clones of the humanized anti-C-MET antibody molecule or antigen-binding portion thereof comprising one or more mutations in the CDRs;
(3) screening the phage library for binding to human C-MET and optionally also to cynomolgus monkey C-MET;
(4) selecting clones from the screening step (3) having binding specificity to human C-MET and optionally also to cynomolgus monkey C-MET; and
(5) producing an antibody molecule which specifically binds to human C-MET and optionally also to cynomolgus monkey C-MET, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

BRIEF DESCRIPTION OF THE FIGURES

FIG. 10A: (1) h224G11 and (2) 08G07; FIG. 10B: (3) MH7 and (4) MH7-1; FIG. 10C: (5) MH7-2 and (6) MH7-3. In all panels, signal is measured in Fluorescence Units.

DETAILED DESCRIPTION OF THE INVENTION

Figure 1A:
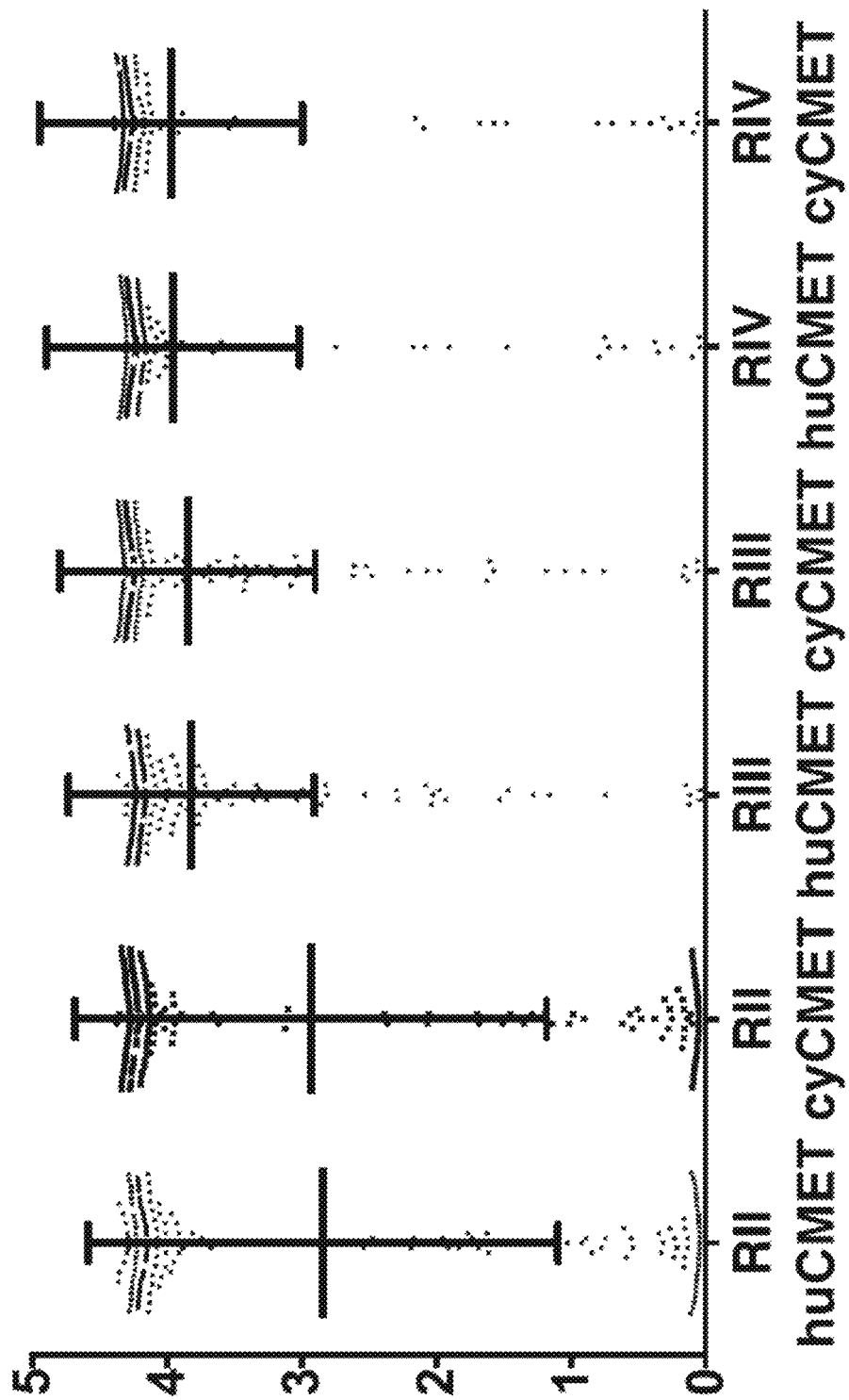
FIG. 1A-FIG. 1B. Direct binding ELISA and Alphascreen competition screening of library-derived anti-C-MET Fabs against human and cyno C-MET-Fc proteins. Clones were derived from multiple phage selection branches where phage populations were selected on biotinylated human, or cynomolgus monkey C-MET proteins in each of rounds II-IV. After each round of selection, library-derived clones were screened as periplasmically-expressed Fab proteins, against both human (huCMET) and cyno (cyCMET) in ELISA (FIG. 1A), and in blocking the binding of 224G11 IgG in binding to huCMET by Alphascreen (FIG. 1B). Mean±SD values in each round are represented in grey bars.

According to a first aspect of the invention, there is provided an antibody molecule which specifically binds to human C-MET and optionally also to cynomolgus monkey C-MET, or an antigen-binding portion thereof, wherein the antibody molecule or antigen-binding portion comprises a heavy chain variable region with:
- an HCDR1 having amino acids in sequence in the following order: G-Y-I or any amino acid (such as T)-F-T-A or any amino acid (such as S)-Y-Y or any amino acid (such as A, S or T)-M-H (SEQ ID NO: 22);
- an HCDR2 having amino acids in sequence in the following order: M-G-W or any amino acid (such as I)-I-K or any amino acid (such as N)-P-N or any amino acid (such as S)-N or any amino acid (such as G)-G-L or any amino acid (such as S)-A or any amino acid (such as T)-N or any amino acid (such as S)-Y-A-Q-K-F-Q-G (SEQ ID NO: 23); and
- an HCDR3 having amino acids in sequence in the following order: S or any amino acid (such as A/E/H/M/Q/T/V)-E-I-T-T-E or any amino acid (such as D)-F or any amino acid (such as L)-D-Y or any amino acid (such as A/E/F/I/K/LM/Q/S/V/W) (SEQ ID NO: 24).

In some aspects an anti-C-MET antibody or antigen-binding portion provided herein specifically binds to a C-MET protein comprising or consisting of SEQ ID NO:18 or SEQ ID NO:19. In some aspects an anti-C-MET antibody or antigen-binding portion provided herein specifically binds to a C-MET protein having an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:18 or SEQ ID NO:19.

In aspects of the invention, the HCDR1 of the antibody molecule or antigen-binding portion may exclude the sequence GYIFTAYTMH (SEQ ID NO: 25; 224G11 murine/humanized antibody HCDR1 disclosed in WO2011151412A1; US 2013/0216527A1), the HCDR2 of the antibody molecule or antigen-binding portion may exclude the sequence MGWIKPNNGLANYAQKFQG (SEQ ID NO: 26; 224G11 murine/humanized antibody HCDR1 disclosed in WO2011151412A1; US 2013/0216527A1), and/or the HCDR3 of the antibody molecule or antigen-binding portion may exclude the sequence SEITTEFDY (SEQ ID NO: 27; 224G11 murine/humanized antibody HCDR3 disclosed in WO2011151412A1; US 2013/0216527A1).

The antibody molecule or antigen-binding portion may further comprise a light chain variable region with:
- an LCDR1 having amino acids in sequence in the following order: R-A-S-Q-S-V-D or any amino acid (for example, S or E)-S-Y-A-N or any amino acid (for example, Q)-S-F or any amino acid (for example, Y)-L-H or any amino acid (for example, A) (SEQ ID NO: 28);
- an LCDR2 having amino acids in sequence in the following order: R or any amino acid (for example, A)-A or any amino acid (for example, G)-S-T or any amino acid (for example, S)-R-E-S or any amino acid (for example, T); and
- an LCDR3 having amino acids in sequence in the following order: Q-Q-S or any amino acid (for example, Y)-K or any amino acid (for example, G)-E or any amino acid (for example, D, S)-D or any amino acid (for example, S, E, R)-P-L-T (SEQ ID NO: 30).

In aspects of the invention, the LCDR1 of the antibody molecule or antigen-binding portion may exclude the sequence KSSESVDSYANSFLH (SEQ ID NO: 31; 224G11 murine/humanized antibody LCDR1 disclosed in WO2011151412A1; US 2013/0216527A1), and/or the LCDR2 of the antibody molecule or antigen-binding portion may exclude the sequence RASTRES (SEQ ID NO: 32; 224G11 murine/humanized antibody LCDR2 disclosed in WO2011151412A1; US 2013/0216527A1), and/or the LCDR3 of the antibody molecule or antigen-binding portion may exclude the sequence QQSKEDPLT (SEQ ID NO: 33; 224G11 murine/humanized antibody LCDR3 disclosed in WO2011151412A1; US 2013/0216527A1).

In some aspects, disclosed herein is an anti-C-MET antibody or an antigen-binding portion thereof, wherein the antibody comprises a heavy chain variable (VH) region and a light chain variable (VL) region, wherein
(a) the HCDR1 comprises the amino acid sequence G-Y-$X_1$-F-T-$X_2$-Y-$X_3$-M-H, wherein $X_1$ is I or any other amino acid, $X_2$ is A or any other amino acid and $X_3$ is Y or any other amino acid (SEQ ID NO: 22);
(b) the HCDR2 comprises M-G-$X_1$-I-$X_2$-P-$X_3$-$X_4$-G-$X_5$-$X_6$-$X_7$-Y-A-Q-K-F-Q-G, wherein $X_1$ is W or any other amino acid, $X_2$ is K or any other amino acid, $X_3$ is N or any other amino acid, $X_4$ is N or any other amino acid, $X_5$ is L or any other amino acid, $X_6$ is A or any other amino acid and $X_7$ is N or any other amino acid (SEQ ID NO: 23);
(c) the HCDR3 comprises $X_1$-E-I-T-T-$X_2$-$X_3$-D-$X_4$, wherein $X_1$ is S or any other amino acid, $X_2$ is E or any other amino acid, $X_3$ is F or any other amino acid and $X_4$ is Y or any other amino acid (SEQ ID NO: 24);
(d) the LCDR1 comprises R-A-S-Q-S-V-$X_1$-S-Y-A-$X_2$-S-$X_3$-L-$X_4$, wherein $X_1$ is D or any other amino acid, $X_2$ is N or any other amino acid, $X_3$ is F or any other amino acid of F and $X_4$ is H or any other amino acid (SEQ ID NO: 28);
(e) the LCDR2 comprises $X_1$-$X_2$-S-$X_3$-R-E-$X_4$, wherein $X_1$ is R or any other amino acid, $X_2$ is A or any other amino acid, $X_3$ is T or any other amino acid and $X_4$ is S or any other amino acid; and
(f) the LCDR3 comprises Q-Q-$X_1$-$X_2$-$X_3$-$X_4$-P-L-T, wherein $X_1$ is S or any other amino acid, $X_2$ is K or any other amino acid, $X_3$ is E or any other amino acid and $X_4$ is D or any other amino acid (SEQ ID NO: 30). In some aspects, the HCDR1 $X_1$ is T. In some aspects, the HCDR2 $X_3$ is a conservative substitution of N. In some aspects, the HCDR2 $X_4$ is a conservative substitution of N. In some aspects, the HCDR2 $X_7$ is a conservative substitution of N. In some aspects, the LCDR1 $X_2$ is a conservative substitution of N. In some aspects, the LCDR1 $X_3$ is a conservative substitution of F. In some aspects, the LCDR2 $X_3$ is a conservative substitution of T. In some aspects, the LCDR2 $X_4$ is a conservative substitution of S.

In some aspects, disclosed herein is an anti-C-MET antibody or an antigen-binding portion thereof, wherein the antibody comprises a heavy chain variable (VH) region comprising, in amino-terminal to carboxyl-terminal order, FR1-HCDR1-FR2-HCDR2-FR3-HCDR3-FR4 and a light chain variable (VL) region comprising, in amino-terminal to carboxyl-terminal order, FR1-LCDR1-FR2-LCDR2-FR3-LCDR3-FR4, wherein the HCDR1 is SEQ ID NO:22, the HCDR2 is SEQ ID NO:23, the HCDR3 is SEQ ID NO:24, the LCDR1 is SEQ ID NO:28, the LCDR2 is $X_1$-$X_2$-S-$X_3$-R-E-$X_4$, wherein $X_1$ is R or any other amino acid, $X_2$ is A or any other amino acid, $X_3$ is T or any other amino acid and $X_4$ is S or any other amino acid, and the LCDR3 is SEQ ID NO:30, wherein the heavy chain FR1, FR2, FR3 and FR4 amino acid sequences are the heavy chain FR1, FR2, FR3 and FR4 amino acid sequences in SEQ ID NO: 127 (see Table 2) and wherein the light chain FR1, FR2, FR3 and FR4 amino acid sequences are the light chain FR1, FR2, FR3 and FR4 amino acid sequences in SEQ ID NO: 129 (see Table 2).

As elaborated herein, the present inventors have succeeded for the first time in generating a number of optimized anti-C-MET antibody molecules using CDR sequences derived from the murine anti-C-MET antibody 224G11 disclosed in WO2011151412A1; US 2013/0216527A1. In embodiments of the present invention, these antibody molecules have been selected to have binding specificity to both human C-MET as well as cynomolgus monkey C-MET (to facilitate in vivo studies in an appropriate animal test species). Further refining of the optimized antibody molecules as described herein has provided improved variable domain stability, higher expression yields, and/or reduced immunogenicity.

Preferred optimized anti-C-MET antibody molecules of the present invention do not necessarily have the maximum number of human germline substitutions at corresponding murine CDR or other (such as framework) amino acid positions. As elaborated in the experimental section below, we have found that "maximally humanized" antibody molecules are not necessary "maximally optimized" in terms of anti-C-MET binding characteristics and/or other desirable features.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to C-MET. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence: G-Y-I/T-F-T-A/S-Y-Y/S/T/A-M-H (SEQ ID NO: 64); the HCDR2 may have the amino acid sequence: M-G-W/I-I-K/N-P-N/S-N/G-G-L/S-A/T-N/S-Y-A-Q-K-F-Q-G (SEQ ID NO: 65); and the HCDR3 may have the amino acid sequence: S/A/E/H/M/Q/T/V-E-1-T-T-E/D-F/L-D-Y/A/E/F/I/K/L/M/Q/S/V/W (SEQ ID NO: 66).

For example, the HCDR1 may have the amino acid sequence: G-Y-T-F-T-S-Y-A/S/T-M-H (SEQ ID NO: 67); the HCDR2 may have the amino acid sequence: M-G-W/I-I-N-P-S-G-G-S-T-S-Y-A-Q-K-F-Q-G (SEQ ID NO: 68); and the HCDR3 may have the amino acid sequence: S/A/E/Q/T-E-I-T-T-E/D-F-D-Y/I (SEQ ID NO: 69).

In the antibody molecule or antigen-binding portion thereof, the LCDR1 may have the amino acid sequence: R-A-S-Q-S-V-D/S/E-S-Y-A-N/Q-S-F/Y-L-H/A (SEQ ID NO: 70); the LCDR2 may have the amino acid sequence: R/A-A/G-S-T/S-R-E-T/S; and the LCDR3 may have the amino acid sequence: Q-Q-S/Y-K/G-E/D/S-D/S/E/R-P-L-T (SEQ ID NO: 72).

For example, the LCDR1 may have the amino acid sequence: R-A-S-Q-S-V-D/S/E-S-Y-A-N/Q-S-Y-L-H (SEQ ID NO: 73); the LCDR2 may have the amino acid sequence: R-G-S-T-R-E-T/S (SEQ ID NO: 74); and the LCDR3 may have the amino acid sequence: Q-Q-S/Y-K/G-E/S-D/S/E-P-L-T (SEQ ID NO: 75).

In specific embodiments of the invention, the antibody molecule or antigen-binding portion may comprise:

(a) the amino acid sequences RASQSVESYAQSYLH (LCDR1; SEQ ID NO: 46), RGSTRES (LCDR2; SEQ ID NO: 38), QQSKSDPLT (LCDR3; SEQ ID NO: 76), GYIFTSYSMH (HCDR1; SEQ ID NO: 43), MGWINPSNGLANYAQKFQG (HCDR2; SEQ ID NO: 44), QEITTEFDI (HCDR3; SEQ ID NO: 45), [Clone 04F09]; or (b) the amino acid sequences RASQSVDSYANSYLH (LCDR1; SEQ ID NO: 51), RGSTRES (LCDR2; SEQ ID NO: 38), QQSKESPLT (LCDR3; SEQ ID NO: 47), GYIFTSYTMH (HCDR1; SEQ ID NO: 48), MGWINPNGGLASYAQKFQG (HCDR2; SEQ ID NO: 49), SEITTEQDY (HCDR3; SEQ ID NO: 50), [Clone 07A01]; or (c) the amino acid sequences RASQSVSSYAQSYLH (LCDR1; SEQ ID NO: 57), RASTRET (LCDR2; SEQ ID NO: 77), QQSKESPLT (LCDR3; SEQ ID NO: 47), GYTFTSYSMH (HCDR1; SEQ ID NO: 78), MGWINPNGGLTNYAQKFRG (HCDR2; SEQ ID NO: 79), EEITTEFDY (HCDR3; SEQ ID NO: 80), [Clone 09A12]; or (d) the amino acid sequences RASQSVSSYANSYLH (LCDR1; SEQ ID NO: 37), RGSTRES (LCDR2; SEQ ID NO: 38), QQSKSDPLT (LCDR3; SEQ ID NO: 76), GYTFTSYTMH (HCDR1; SEQ ID NO: 34), MGWINPNNGSTNYAQKFQG (HCDR2; SEQ ID NO: 81), SEITTDFDY (HCDR3; SEQ ID NO: 55), [Clone 09B08]; or (e) the amino acid sequences RASQSVESYAQSYLH (LCDR1; SEQ ID NO: 46), RGSTRES (LCDR2; SEQ ID NO: 38), QQSKEEPLT (LCDR3; SEQ ID NO: 82), GYIFTAYSMH (HCDR1; SEQ ID NO: 83), MGIIKPSNGSTNYAQKFQG (HCDR2; SEQ ID NO: 84), AEITTEFDY (HCDR3; SEQ ID NO: 85), [Clone 07C10]; or (f) the amino acid sequences RASQSVESYANSYLH (LCDR1; SEQ ID NO: 52), RGSTRES (LCDR2; SEQ ID NO: 38), QQYGSEPLT (LCDR3; SEQ ID NO: 53), GYIFTSYTMH (HCDR1; SEQ ID NO: 48), MGWINPNGGSTSYAQKFQG (HCDR2; SEQ ID NO: 42), QEITTEFDY (HCDR3; SEQ ID NO: 36), [Clone 09E04]; or (g) the amino acid sequences RASQSVDSYANSYLH (LCDR1; SEQ ID NO: 51), RGSTRES (LCDR2; SEQ ID NO: 38), QQSKSEPLT (LCDR3; SEQ ID NO: 39), GYTFTSYTMH (HCDR1; SEQ ID NO: 34), MGWINPSGGLANYAQKFQG (HCDR2; SEQ ID NO: 54), SEITTDFDY (HCDR3; SEQ ID NO: 55), [Clone 08G07]; or (h) the amino acid sequences RASQSVDSYANSYLH (LCDR1; SEQ ID NO: 51), RGSTRES (LCDR2; SEQ ID NO: 38), QQSKSEPLT (LCDR3; SEQ ID NO: 39), GYIFTSYTMH (HCDR1; SEQ ID NO: 48), MGWIKPNNGSASYAQKFQG (HCDR2; SEQ ID NO: 86), SEITTDFDY (HCDR3; SEQ ID NO: 55), [Clone 04E10]; or (i) the amino acid sequences RASQSVDSYANSYLH (LCDR1; SEQ ID NO: 51), RGSTRET (LCDR2; SEQ ID NO: 56), QQSKSDPLT (LCDR3; SEQ ID NO: 76), GYIFTAYSMH (HCDR1; SEQ ID NO: 83), MGWIKPNNGSTNYAQKFQG (HCDR2; SEQ ID NO: 87), TEITTEFDY (HCDR3; SEQ ID NO: 88), [Clone 08G12]; or (j) the amino acid sequences RASQSVSSYANSYLH (LCDR1; SEQ ID NO: 37), RGSTRES (LCDR2; SEQ ID NO: 38), QQSKSEPLT (LCDR3; SEQ ID NO: 39), GYTFTSYTMH (HCDR1; SEQ ID NO: 34), MGWINPNGGSTSYAQKFQG (HCDR2; SEQ ID NO: 42), QEITTEFDY (HCDR3; SEQ ID NO: 36), [Clone MH1]; or (k) the amino acid sequences RASQSVSSYAQSYLH (LCDR1; SEQ ID NO: 57), RGSTRET (LCDR2; SEQ ID NO: 56), QQSGSSPLT (LCDR3; SEQ ID NO: 89), GYTFTSYTMH (HCDR1; SEQ ID NO: 34), MGWINPNGGSTSYAQKFQG (HCDR2; SEQ ID NO: 42), QEITTEFDY (HCDR3; SEQ ID NO: 36), [Clone MH2]; or (l) the amino acid sequences RASQSVSSYAQSYLH (LCDR1; SEQ ID NO: 57), RGSTRET (LCDR2; SEQ ID NO: 56), QQYGSSPLT (LCDR3; SEQ ID NO: 90), GYTFTSYTMH (HCDR1; SEQ ID NO: 34), MGWINPNGGSTSYAQKFQG (HCDR2; SEQ ID NO: 42), QEITTEFDY (HCDR3; SEQ ID NO: 36), [Clone MH3]; or (m) the amino acid sequences RASQSVSSYANSYLH (LCDR1; SEQ ID NO: 37), RGSTRES (LCDR2; SEQ ID NO: 38), QQSKSEPLT (LCDR3; SEQ ID NO: 39), GYTFTSYTMH (HCDR1; SEQ ID NO: 34), MGWINPSGGSTSYAQKFQG (HCDR2; SEQ ID NO: 40), QEITTEFDY (HCDR3; SEQ ID NO: 36), [Clone MH4]; or (n) the amino acid sequences RASQSVSSYAQSYLH (LCDR1; SEQ ID NO: 57), RGSTRET (LCDR2; SEQ ID NO: 56), QQSGSSPLT (LCDR3; SEQ ID NO: 89), GYTFTSYTMH (HCDR1; SEQ ID NO: 34), MGWINPSGGSTSYAQKFQG (HCDR2; SEQ ID NO: 40), QEITTEFDY (HCDR3; SEQ ID NO: 36), [Clone MH5]; or (o) the amino acid sequences RASQSVSSYAQSYLH (LCDR1; SEQ ID NO: 57), RGSTRET (LCDR2; SEQ ID NO: 56), QQYGSSPLT (LCDR3; SEQ ID NO: 90), GYTFTSYTMH (HCDR1; SEQ ID NO: 34), MGWINPSGGSTSYAQKFQG (HCDR2; SEQ ID NO: 40), QEITTEFDY (HCDR3; SEQ ID NO: 36), [Clone MH6]; or (p) the amino acid sequences RASQSVSSYANSYLH (LCDR1; SEQ ID NO: 37), RGSTRES (LCDR2; SEQ ID NO: 38), QQSKSEPLT (LCDR3; SEQ ID NO: 39), GYTFTSYTMH (HCDR1; SEQ ID NO: 34), MGI-INPSGGSTSYAQKFQG (HCDR2; SEQ ID NO: 35) QEITTEFDY (HCDR3; SEQ ID NO: 36), [Clone MH7]; or (q) the amino acid sequences RASQSVSSYAQSYLH (LCDR1; SEQ ID NO: 57), RGSTRET (LCDR2; SEQ ID NO: 56), QQSGSSPLT (LCDR3; SEQ ID NO: 89), GYTFTSYTMH (HCDR1; SEQ ID NO: 34), MGI-INPSGGSTSYAQKFQG (HCDR2; SEQ ID NO: 35) QEITTEFDY (HCDR3; SEQ ID NO: 36), [Clone MH8]; or (r) the amino acid sequences RASQSVSSYAQSYLH (LCDR1; SEQ ID NO: 57), RGSTRET (LCDR2; SEQ ID NO: 56), QQYGSSPLT (LCDR3; SEQ ID NO: 90), GYTFTSYTMH (HCDR1; SEQ ID NO: 34), MGI-INPSGGSTSYAQKFQG (HCDR2; SEQ ID NO: 35) QEITTEFDY (HCDR3; SEQ ID NO: 36), [Clone MH9]; or (s) the amino acid sequences RASQSVSSYANSYLH (LCDR1; SEQ ID NO: 37), RGSTRES (LCDR2; SEQ ID NO: 38), QQSKSEPLT (LCDR3; SEQ ID NO: 39), GYTFTSYAMH (HCDR1; SEQ ID NO: 41), MGWINPSGGSTSYAQKFQG (HCDR2; SEQ ID NO: 40), QEITTEFDY (HCDR3; SEQ ID NO: 36), [Clone MH10]; or (t) the amino acid sequences RASQSVSSYAQSYLH (LCDR1; SEQ ID NO: 57), RGSTRET (LCDR2; SEQ ID NO: 56), QQSGSSPLT (LCDR3; SEQ ID NO: 89), GYTFTSYAMH (HCDR1; SEQ ID NO: 41), MGWINPSGGSTSYAQKFQG (HCDR2; SEQ ID NO: 40), QEITTEFDY (HCDR3; SEQ ID NO: 36), [Clone MH11]; or (u) the amino acid sequences RASQSVSSYAQSYLH (LCDR1; SEQ ID NO: 57), RGSTRET (LCDR2; SEQ ID NO: 56), QQYGSSPLT (LCDR3; SEQ ID NO: 90), GYTFTSYAMH (HCDR1; SEQ ID NO: 41), MGWINPSGGSTSYAQKFQG (HCDR2; SEQ ID NO: 40), QEITTEFDY (HCDR3; SEQ ID NO: 36), [Clone MH12]; or (v) the amino acid sequences RASQSVSSYANSYLH (LCDR1; SEQ ID NO: 37), RGSTRET (LCDR2; SEQ ID NO: 56), QQSKSEPLT (LCDR3; SEQ ID NO: 39), GYTFTSYTMH (HCDR1; SEQ ID NO: 34), MGI-INPSGGSTSYAQKFQG (HCDR2; SEQ ID NO: 35) QEITTEFDY (HCDR3; SEQ ID NO: 36), [Clone MH7-1]; or (w) the amino acid sequences RASQSVSSYANSYLH (LCDR1; SEQ ID NO: 37), RGSTRET (LCDR2; SEQ ID NO: 56), QQSKESPLT (LCDR3; SEQ ID NO: 47), GYTFTSYTMH (HCDR1; SEQ ID NO: 34), MGI-INPSGGSTSYAQKFQG (HCDR2; SEQ ID NO: 35) QEITTEFDY (HCDR3; SEQ ID NO: 36), [Clone MH7-2]; or (x) the amino acid sequences RASQSVSSYAQSYLH (LCDR1; SEQ ID NO: 57), RGSTRET (LCDR2; SEQ ID NO: 56), QQSKESPLT (LCDR3; SEQ ID NO: 47), GYTFTSYTMH (HCDR1; SEQ ID NO: 34), MGI-INPSGGSTSYAQKFQG (HCDR2; SEQ ID NO: 35) QEITTEFDY (HCDR3; SEQ ID NO: 36), [Clone MH7-3].

In some aspects, disclosed herein is an anti-C-MET antibody or an antigen-binding portion thereof, wherein the antibody comprises a heavy chain variable (VH) region and a light chain variable (VL) region, wherein In some aspects, the invention provides an anti-C-MET antibody or an antigen-binding portion thereof, wherein the antibody comprises a heavy chain variable (VH) region and a light chain variable (VL) region, wherein (a) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYAQSYLH (SEQ ID NO: 57), LCDR2 of RGSTRET (SEQ ID NO: 56) and LCDR3 of QQSKESPLT (SEQ ID NO: 47);

(b) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 47);

(c) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKSEPLT (SEQ ID NO: 39);

(d) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(e) the VH region amino acid sequence comprises HCDR1 of GYTFTSYTMH (SEQ ID NO: 34), HCDR2 of MGWINPSGGLANYAQKFQG (SEQ ID NO: 54) and HCDR3 of SEITTDFDY (SEQ ID NO: 55); and the VL region amino acid sequence comprises LCDR1 of RASQSVDSYANSYLH (SEQ ID NO: 51), LCDR2 of RGSTRES (LCDR2; SEQ ID NO: 38) and LCDR3 of QQSKSEPLT (SEQ ID NO: 39);

(f) the VH region amino acid sequence comprises HCDR1 of GYTFTSYTMH (SEQ ID NO: 34), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(g) the VH region amino acid sequence comprises HCDR1 of GYTFTSYAMH (SEQ ID NO: 41), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(h) the VH region amino acid sequence comprises HCDR1 of GYTFTSYTMH (SEQ ID NO: 34), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(i) the VH region amino acid sequence comprises HCDR1 of GYIFTSYSMH (SEQ ID NO: 43), HCDR2 of MGWINPSNGLANYAQKFQG (SEQ ID NO: 44) and HCDR3 of QEITTEFDI (SEQ ID NO: 45); and the VL region amino acid sequence comprises LCDR1 of RASQSVESYAQSYLH (SEQ ID NO: 46), LCDR2 of RGSTRES (SEQ ID NO: 38) and LCDR3 of QQSKSDPLT (SEQ ID NO: 76);

(j) the VH region amino acid sequence comprises HCDR1 of GYIFTSYTMH (SEQ ID NO: 48), HCDR2 of MGWINPNGGLASYAQKFQG (SEQ ID NO: 49) and HCDR3 of SEITTEQDY (SEQ ID NO: 50); and the VL region amino acid sequence comprises LCDR1 of RASQSVDSYANSYLH (SEQ ID NO: 51), LCDR2 of RGSTRES (SEQ ID NO: 38) and LCDR3 of QQSKESPLT (SEQ ID NO: 47); or (k) the VH region amino acid sequence comprises HCDR1 of GYIFTSYTMH (SEQ ID NO: 48), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVESYANSYLH (SEQ ID NO: 52)

In some aspects, disclosed herein is an anti-C-MET antibody or an antigen-binding portion thereof, wherein the antibody comprises a heavy chain variable (VH) region and a light chain variable (VL) region, wherein the VH region comprises any one of the VH region amino acid sequences in Table 10 and the VL region comprises any one of the VL region amino acid sequences in Table 10.

In some aspects, disclosed herein is an anti-C-MET antibody or an antigen-binding portion thereof, wherein the antibody comprises a heavy chain variable (VH) region and a light chain variable (VL) region, wherein (a) the VH region amino acid sequence comprises SEQ ID NO:1 and the VL region amino acid sequence comprises SEQ ID NO:2;

(b) the VH region amino acid sequence comprises SEQ ID NO:3 and the VL region amino acid sequence comprises SEQ ID NO:4;

(c) the VH region amino acid sequence comprises SEQ ID NO:5 and the VL region amino acid sequence comprises SEQ ID NO:6;

(d) the VH region amino acid sequence comprises SEQ ID NO:7 and the VL region amino acid sequence comprises SEQ ID NO:8; or (e) the VH region amino acid sequence comprises SEQ ID NO:9 and the VL region amino acid sequence comprises SEQ ID NO:10.

In some aspects, disclosed herein is an anti-C-MET antibody or an antigen-binding portion thereof, wherein the antibody comprises a heavy chain variable (VH) region and a light chain variable (VL) region, wherein (a) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:1 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:2;

(b) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:3 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:4;

(c) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:5 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:6;

(d) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:7 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:8; or (e) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:9 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:10.

In some aspects, the antibody or antigen-binding portion as defined herein may be isolated.

The antibody molecule or antigen-binding portion as defined herein may cross-compete for binding to C-MET with an antibody or antigen-binding portion thereof comprising the sets of CDRs disclosed herein. In some embodiments, the invention provides an isolated anti-C-MET antibody or an antigen-binding portion thereof, wherein the antibody or antigen-binding portion cross-competes for binding to C-MET with the antibody or antigen-binding portion comprising the sets of CDRs disclosed herein; and (a) comprises fully germline human framework amino acid sequences; (b) does not comprise a 'DS' isomerisation site in the LCDR1, (c) does not comprise a 'NS' deamidation site in the LCDR1, (d) does not comprise an exposed 'F' side chain in the LCDR1 that constitutes and oxidation risk, (e) does not comprise a 'NG' deamidation site in the HCDR2, (e) does not comprise a 'NN' deamidation site in the HCDR2, (f) does not comprise an exposed 'W' side chain in the HCDR2 that constitutes and oxidation risk, and/or (g) does not comprise a 'DP' acid hydrolysis site in the LCDR3; and/or (h) does not comprise a human T cell epitope sequence in the LCDR2; and/or (i) does not comprise a human T cell epitope sequence in the LCDR3; and/or (j) exhibits a higher isoelectric point in comparison to the isoelectric point of antibody h224G11; and/or (k) exhibits an isoelectric point of 8.0 or above as measured by isoelectric focusing, when in human IgG4(S228P) format. The amino acid sequences of antibody h224G11 may be found in Table 2.

The terms "cross-compete", "cross-competition", "cross-block", "cross-blocked" and "cross-blocking" are used interchangeably herein to mean the ability of an antibody or portion thereof to interfere with the binding directly or indirectly through allosteric modulation of the anti-C-MET antibodies of the invention to the target C-MET (e.g., human C-MET). The extent to which an antibody or portion thereof is able to interfere with the binding of another to the target, and therefore whether it can be said to cross-block or cross-compete according to the invention, can be determined using competition binding assays. One example of a binding competition assay is Homogeneous Time Resolved Fluorescence (HTRF). One particularly suitable quantitative cross-competition assay uses a FACS- or an AlphaScreen-based approach to measure competition between the labelled (e.g. His tagged, biotinylated or radioactive labelled) antibody or portion thereof and the other antibody or portion thereof in terms of their binding to the target. In general, a cross-competing antibody or portion thereof is, for example, one which will bind to the target in the cross-competition assay such that, during the assay and in the presence of a second antibody or portion thereof, the recorded displacement of the immunoglobulin single variable domain or polypeptide according to the invention is up to 100% (e.g. in a FACS based competition assay) of the maximum theoretical displacement (e.g. displacement by cold (e.g. unlabeled) antibody or fragment thereof that needs to be cross-blocked) by the potentially cross-blocking antibody or fragment thereof that is present in a given amount. Preferably, cross-competing antibodies or portions thereof have a recorded displacement that is between 10% and 100%, or between 50% and 100%.

The antibody molecule or antigen-binding portion as defined herein may be thermally stable. In some cases, an antibody molecule or antigen-binding portion may have substantially the same thermal stability as murine anti-C-MET antibody 224G11 or h224G11. In some cases, an antibody molecule or antigen-binding portion may be more thermally stable than murine anti-C-MET antibody 224G11 or h224G11. In some examples, an antibody molecule or antigen-binding portion may have a melting temperature (Tm) from about 77° C. to about 81° C. and may be in a human IgG4 format. In some aspects, an antibody molecule or antigen-binding portion may have a Tm from about 77.2° C. to about 80.6° C. and may be in a human IgG4 format. In some cases, an antigen-binding portion is a Fab. The melting temperature of an antibody molecule or antigen-binding portion thereof may be analysed by a differential scanning calorimetry (DSC) assay.

In some examples, the antibody molecule or antigen-binding portion as defined herein may have a higher isoelectric point (pI) than murine anti-C-MET antibody 224G11 or h224G11.

In some cases, the antibody molecule or antigen-binding portion thereof may have a pI greater than about pH 7.3 or greater than about pH 7.4. For example, the antibody molecule or antigen-binding portion thereof may have a pI from about pH 7.3 to about pH 8.5. The isoelectric point of an antibody molecule or antigen-binding portion thereof may be analysed by a protein charge variant assay.

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 1318-1321). Removal of such a site for example by substitution, deletion and/or insertion and then optionally testing (experimentally and/or theoretically) for (a) binding activity and/or (b) loss of the PTM is contemplated.

For example, the 224G11 murine LCDR3 (as defined herein, i.e. the amino acid sequence QQSKEDPLT (SEQ ID NO: 33)) has been identified to have a putative acid hydrolysis site at residues 6 and 7 (DP). Removal this site at equivalent positions in an LCDR3 of the invention, for example by substitution of D (such as to S, or E), is envisaged (as for example in clone MH7 and others found in Tables 3 and 4).

In a further example, the 224G11 murine LCDR1 (as defined herein, i.e. the amino acid sequence KSSESVDSYANSFLH (SEQ ID NO: 31)) has been identified to have a putative isomerisation site at residue 7 (D). Removal this site at equivalent positions in an LCDR1 of the invention, for example by substitution of D (such as to S, or E), is envisaged (as for example in clone MH7 and others found in Tables 3 and 4).

In a further example, the 224G11 murine LCDR1 (as defined herein, i.e. the amino acid sequence KSSESVDSYANSFLH (SEQ ID NO: 31)) has been identified to have a putative deamidation site at residue 11 (N). Removal this site at equivalent positions in an LCDR1 of the invention, for example by substitution of N (such as to Q), is envisaged (as for example in clone 04F09 and others found in Tables 3 and 4).

In a further example, the 224G11 murine LCDR1 (as defined herein, i.e. the amino acid sequence KSSESVDSYANSFLH (SEQ ID NO: 31)) has been identified to have a putative oxidation site at residue 13 (F), which is in a known solvent-exposed region of the CDR loop. Removal this site at equivalent positions in an LCDR1 of the invention, for example by substitution of F (such as to Y), is envisaged (as for example in clone MH7 and others found in Tables 3 and 4).

In a further example, the 224G11 murine HCDR2 (as defined herein, i.e. the amino acid sequence MGWIKPNNGLANYAQKFQG (SEQ ID NO: 26)) has been identified to have a putative oxidation site at residue 3 (W), which is in a known solvent-exposed region of the CDR loop. Removal this site at equivalent positions in an HCDR2 of the invention, for example by substitution of W (such as to I), is envisaged (as for example in clone MH7 and others found in Tables 3 and 4).

In a further example, the 224G11 murine HCDR2 (as defined herein, i.e. the amino acid sequence MGWIKPNNGLANYAQKFQG (SEQ ID NO: 26)) has been identified to have a putative deamidation site at residue 7 (N), which is in a known solvent-exposed region of the CDR loop. Removal this site at equivalent positions in an HCDR2 of the invention, for example by substitution of N (such as to S), is envisaged (as for example in clone MH7 and others found in Tables 3 and 4).

In a further example, the 224G11 murine HCDR2 (as defined herein, i.e. the amino acid sequence MGWIKPNNGLANYAQKFQG (SEQ ID NO: 26)) has been identified to have a putative deamidation site at residue 8 (N), which is in a known solvent-exposed region of the CDR loop. Removal this site at equivalent positions in an HCDR2 of the invention, for example by substitution of N (such as to G), is envisaged (as for example in clone MH7 and others found in Tables 3 and 4).

The antibody molecule or antigen-binding portion thereof may be human, humanized or chimeric.

The antibody molecule or antigen-binding portion thereof may comprise one or more human variable domain framework scaffolds into which the CDRs have been inserted. For example, the VH region, the VL region, or both the VH and the VL region may comprise one or more human framework region amino acid sequences.

The antibody molecule or antigen-binding portion thereof may comprise an IGHV1-46 human germline scaffold into which the corresponding HCDR sequences have been inserted. The antibody molecule or antigen-binding portion thereof may comprise a VH region that comprises an IGHV1-46 human germline scaffold amino acid sequence into which a set of corresponding HCDR1, HCDR2 and HCDR3 amino acid sequences have been inserted.

The antibody molecule or antigen-binding portion thereof may comprise an IGKV3-20 human germline scaffold into which the corresponding LCDR sequences have been inserted. The antibody molecule or antigen-binding portion thereof may comprise a VL region that comprises an IGKV3-20 human germline scaffold amino acid sequence into which a set of corresponding LCDR1, LCDR2 and LCDR3 amino acid sequences have been inserted.

The antibody molecule or antigen-binding portion thereof may comprise an IGHV1-46 human germline scaffold into which the corresponding HCDR sequences have been inserted and an IGKV3-20 human germline scaffold into which the corresponding LCDR sequences have been inserted. The antibody molecule or antigen-binding portion thereof may comprise a VH region that comprises an IGHV1-46 human germline scaffold amino acid sequence into which a set of corresponding HCDR1, HCDR2 and HCDR3 amino acid sequences have been inserted and a VL region that comprises an IGKV3-20 human germline scaffold amino acid sequence into which a set of corresponding LCDR1, LCDR2 and LCDR3 amino acid sequences have been inserted. The HCDR1, HCDR2, HCDR3, LCDR1, LCDR2 and LCDR3 amino acid sequences may be the HCDR1, HCDR2, HCDR3, LCDR1, LCDR2 and LCDR3 amino acid sequences of any one of the clones in Table 4 or 8 (with all six CDR sequences being from the same clone).

In some aspects, the antibody molecule or antigen-binding portion thereof may comprise an immunoglobulin constant region. In some embodiments, the immunoglobulin constant region is IgG1, IgG2, IgG3, IgG4, IgA1 or IgA2. In additional embodiments, the immunoglobulin constant region is IgG1, IgG2, IgG3, IgG4(S228P), IgA1 or IgA2. The antibody molecule or antigen-binding portion thereof may comprise an immunologically inert constant region. In some aspects, an anti-C-MET antibody or antigen-binding portion thereof may comprise an immunoglobulin constant region comprising a wild-type human IgG1 constant region, a human IgG1 constant region comprising the amino acid substitutions L234A, L235A and G237A or a human IgG1 constant region comprising the amino acid substitutions L234A, L235A, G237A and P331S. In some aspects, an anti-C-MET antibody or antigen-binding portion thereof may comprise an immunoglobulin constant region comprising a wild-type human IgG2 constant region or a wild-type human IgG4 constant region. In some aspects, an anti-C-MET antibody may comprise an immunoglobulin constant region comprising any one of the amino acid sequences in Table 11. The Fc region sequences in Table 11 begin at the CH1 domain. In some aspects, an anti-C-MET antibody may comprise an immunoglobulin constant region comprising an amino acid sequence of an Fc region of human IgG4, human IgG4(S228P), human IgG2, human IgG1, human IgG1-3M or human IgG1-4M. For example, the human IgG4(S228P)

Fc region comprises the following substitution compared to the wild-type human IgG4 Fc region: S228P. For example, the human IgG1-3M Fc region comprises the following substitutions compared to the wild-type human IgG1 Fc region: L234A, L235A and G237A, while the human IgG1-4M Fc region comprises the following substitutions compared to the wild-type human IgG1 Fc region: L234A, L235A, G237A and P331S. In some aspects, a position of an amino acid residue in a constant region of an immunoglobulin molecule is numbered according to EU nomenclature (Ward et al., 1995 *Therap. Immunol.* 2:77-94). In some aspects, an immunoglobulin constant region may comprise an RDELT (SEQ ID NO:20) motif or an REEM (SEQ ID NO:21) motif (underlined in Table 11). The REEM (SEQ ID NO:21) allotype is found in a smaller human population than the RDELT (SEQ ID NO:20) allotype. In some aspects, an anti-C-MET antibody may comprise an immunoglobulin constant region comprising any one of SEQ ID NOS:11-17. In some aspects, an anti-C-MET antibody may comprise the six CDR amino acid sequences of any one of the clones in Table 4 or 8 and any one of the Fc region amino acid sequences in Table 11. In some aspects, an anti-C-MET antibody may comprise an immunoglobulin heavy chain constant region comprising any one of the Fc region amino acid sequences in Table 11 and an immunoglobulin light chain constant region that is a kappa light chain constant region or a lambda light chain constant region.

In some aspects, disclosed herein is an anti-C-MET antibody or an antigen-binding portion thereof, wherein the antibody comprises a heavy chain variable (VH) region, a light chain variable (VL) region and a heavy chain constant region, wherein (a) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); the VL region amino acid sequence comprises LCDR1 of RASQSVSSYAQSYLH (SEQ ID NO: 57), LCDR2 of RGSTRET (SEQ ID NO: 56) and LCDR3 of QQSKESPLT (SEQ ID NO: 47); and the heavy chain constant region comprises any one of SEQ ID NOS:11-17;

(b) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 47); and the heavy chain constant region comprises any one of SEQ ID NOS:11-17;

(c) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 39); and the heavy chain constant region comprises any one of SEQ ID NOS:11-17;

(d) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39); and the heavy chain constant region comprises any one of SEQ ID NOS: 11-17;

(e) the VH region amino acid sequence comprises HCDR1 of GYTFTSYTMH (SEQ ID NO: 34), HCDR2 of MGWINPSGGLANYAQKFQG (SEQ ID NO: 54) and HCDR3 of SEITTDFDY (SEQ ID NO: 55); the VL region amino acid sequence comprises LCDR1 of RASQSVDSYANSYLH (SEQ ID NO: 51), LCDR2 of RGSTRES (LCDR2; SEQ ID NO: 38) and LCDR3 of QQSKSEPLT (SEQ ID NO: 39); and the heavy chain constant region comprises any one of SEQ ID NOS:11-17;

(f) the VH region amino acid sequence comprises HCDR1 of GYTFTSYTMH (SEQ ID NO: 34), HCDR2 of MGWINPSGGSTSYAQKFQG (SEQ ID NO: 40) and HCDR3 of QEITTEFDY (SEQ ID NO: 36); the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39); and the heavy chain constant region comprises any one of SEQ ID NOS:11-17;

(g) the VH region amino acid sequence comprises HCDR1 of GYTFTSYAMH (SEQ ID NO: 41), HCDR2 of MGWINPSGGSTSYAQKFQG (SEQ ID NO: 40) and HCDR3 of QEITTEFDY (SEQ ID NO: 36); the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39); and the heavy chain constant region comprises any one of SEQ ID NOS: 11-17;

(h) the VH region amino acid sequence comprises HCDR1 of GYTFTSYTMH (SEQ ID NO: 34), HCDR2 of MGWINPNGGSTSYAQKFQG (SEQ ID NO: 42) and HCDR3 of QEITTEFDY (SEQ ID NO: 36); the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39); and the heavy chain constant region comprises any one of SEQ ID NOS: 11-17;

(i) the VH region amino acid sequence comprises HCDR1 of GYIFTSYSMH (SEQ ID NO: 43), HCDR2 of MGWINPSNGLANYAQKFQG (SEQ ID NO: 44) and HCDR3 of QEITTEFDI (SEQ ID NO: 45); the VL region amino acid sequence comprises LCDR1 of RASQSVESYAQSYLH (SEQ ID NO: 46), LCDR2 of RGSTRES (SEQ ID NO: 38) and LCDR3 of QQSKSDPLT (SEQ ID NO: 76); and the heavy chain constant region comprises any one of SEQ ID NOS: 11-17;

(j) the VH region amino acid sequence comprises HCDR1 of GYIFTSYTMH (SEQ ID NO: 48), HCDR2 of MGWINPNGGLASYAQKFQG (SEQ ID NO: 49) and HCDR3 of SEITTEQDY (SEQ ID NO: 50); the VL region amino acid sequence comprises LCDR1 of RASQSVDSYANSYLH (SEQ ID NO: 51), LCDR2 of RGSTRES (SEQ ID NO: 38) and LCDR3 of QQSKESPLT (SEQ ID NO: 47); and the heavy chain constant region comprises any one of SEQ ID NOS: 11-17; or (k) the VH region amino acid sequence comprises HCDR1 of GYIFTSYTMH (SEQ ID NO: 48), HCDR2 of MGWINPNGGSTSYAQKFQG (SEQ ID NO: 42)

and HCDR3 of QEITTEFDY (SEQ ID NO: 36); the VL region amino acid sequence comprises LCDR1 of RASQSVESYANSYLH (SEQ ID NO: 52), LCDR2 of RGSTRES (SEQ ID NO: 38) and LCDR3 of QQYGSEPLT (SEQ ID NO: 53); and the heavy chain constant region comprises any one of SEQ ID NOS: 11-17.

In some aspects, disclosed herein is an anti-C-MET antibody or an antigen-binding portion thereof, wherein the antibody comprises a heavy chain variable (VH) region, a light chain variable (VL) region and a heavy chain constant region, wherein
- (a) the VH region amino acid sequence comprises or consists of SEQ ID NO:1; the VL region amino acid sequence comprises or consists of SEQ ID NO:2; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
- (b) the VH region amino acid sequence comprises or consists of SEQ ID NO:3; the VL region amino acid sequence comprises or consists of SEQ ID NO:4; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
- (c) the VH region amino acid sequence comprises or consists of SEQ ID NO:5; the VL region amino acid sequence comprises or consists of SEQ ID NO:6; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
- (d) the VH region amino acid sequence comprises or consists of SEQ ID NO:7; the VL region amino acid sequence comprises or consists of SEQ ID NO:8; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A; or
- (e) the VH region amino acid sequence comprises or consists of SEQ ID NO:9; the VL region amino acid sequence comprises or consists of SEQ ID NO:10; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A.

In some aspects, disclosed herein is an anti-C-MET antibody or an antigen-binding portion thereof, wherein the antibody comprises a heavy chain variable (VH) region, a light chain variable (VL) region and a heavy chain constant region, wherein
- (a) the VH region amino acid sequence comprises or consists of SEQ ID NO:1; the VL region amino acid sequence comprises or consists of SEQ ID NO:2; and the heavy chain constant region comprises any one of SEQ ID NOS:11-17;
- (b) the VH region amino acid sequence comprises or consists of SEQ ID NO:3; the VL region amino acid sequence comprises or consists of SEQ ID NO:4; and the heavy chain constant region comprises any one of SEQ ID NOS:11-17;
- (c) the VH region amino acid sequence comprises or consists of SEQ ID NO:5; the VL region amino acid sequence comprises or consists of SEQ ID NO:6; and the heavy chain constant region comprises any one of SEQ ID NOS:11-17;
- (d) the VH region amino acid sequence comprises or consists of SEQ ID NO:7; the VL region amino acid sequence comprises or consists of SEQ ID NO:8; and the heavy chain constant region comprises any one of SEQ ID NOS:11-17; or
- (e) the VH region amino acid sequence comprises or consists of SEQ ID NO:9; the VL region amino acid sequence comprises or consists of SEQ ID NO:10; and the heavy chain constant region comprises any one of SEQ ID NOS:11-17.

The antibody molecule or antigen-binding portion thereof may be a Fab fragment, a F(ab)$_2$ fragment, an Fv fragment, a tetrameric antibody, a tetravalent antibody, a multispecific antibody (for example, a bispecific antibody), a domain-specific antibody, a single domain antibody, a monoclonal antibody or a fusion protein. In one embodiment, an antibody may be a bispecific antibody that binds specifically to a first antigen and a second antigen, wherein the first antigen is C-MET and the second antigen is not C-MET. Antibody molecules and methods for their construction and use are described, in for example Holliger & Hudson (2005, Nature Biotechnol. 23(9): 1126-1136).

In another aspect of the invention, there is provided an immunoconjugate comprising the antibody molecule or antigen-binding portion thereof of the invention as defined herein linked to a therapeutic agent.

Examples of suitable therapeutic agents include cytotoxins, radioisotopes, chemotherapeutic agents, immunomodulatory agents, anti-angiogenic agents, antiproliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the anti-folates, vinca alkaloids, and the anthracyclines. Plant toxins, other bioactive proteins, enzymes (i.e., ADEPT), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, downregulate self-antigen expression, or mask MHC antigens.

Also provided is a nucleic acid molecule encoding the antibody molecule or antigen-binding portion thereof of the invention as defined herein. A nucleic acid molecule may encode (a) the VH region amino acid sequence; (b) the VL region amino acid sequence; or (c) both the VH and the VL region amino acid sequences of an anti-C-MET antibody or an antigen-binding portion thereof described herein. In some aspects, the nucleic acid molecule as defined herein may be isolated.

Further provided is a vector comprising the nucleic acid molecule of the invention as defined herein. The vector may be an expression vector.

Also provided is a host cell comprising the nucleic acid molecule or the vector of the invention as defined herein. The host cell may be a recombinant host cell.

In a further aspect there is provided a method of producing an anti-C-MET antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

The invention also provides a method for inhibiting C-MET signalling in a cell, the method comprising contacting the cell with an anti-C-MET antibody molecule or antigen-binding portion thereof described herein. In some embodiments, an anti-C-MET antibody molecule or antigen-binding portion of the invention locks C-MET into a nonactivating monomeric form.

Further provided is a method for enhancing an immune response in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein. In some embodiments, an anti-C-MET antibody molecule or antigen-binding portion of the invention engages a subject's immune cells via antibody effector-function mediated engagement.

In a further aspect there is provided a method for treating or preventing cancer in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

For example, the cancer may be Gastrointestinal Stromal cancer (GIST), pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, or cancer of hematological tissues.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an autoimmune disease or an inflammatory disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

For example, the autoimmune disease or inflammatory disease may be arthritis, asthma, multiple sclerosis, psoriasis, Crohn's disease, inflammatory bowel disease, lupus, Grave's disease and Hashimoto's thyroiditis, or ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of a cardiovascular disease or a fibrotic disease.

The cardiovascular disease in any aspect of the invention may for example be coronary heart disease or atherosclerosis.

The fibrotic disease in any aspect of the invention may be, for example, myocardial infarction, angina, osteoarthritis, pulmonary fibrosis, asthma, cystic fibrosis or bronchitis.

In one embodiment, the invention provides an anti-C-MET antibody or an antigen-binding portion thereof comprising the amino acid sequences disclosed herein for use in therapy.

The pharmaceutical composition of the invention may comprise a pharmaceutically acceptable excipient, carrier or diluent. A pharmaceutically acceptable excipient may be a compound or a combination of compounds entering into a pharmaceutical composition which does not provoke secondary reactions and which allows, for example, facilitation of the administration of the anti-C-MET antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-C-MET antibody molecule.

In some embodiments, the anti-C-MET antibody molecule may be provided in a lyophilised form for reconstitution prior to administration. For example, lyophilised antibody molecules may be re-constituted in sterile water and mixed with saline prior to administration to an individual.

The anti-C-MET antibody molecules will usually be administered in the form of a pharmaceutical composition, which may comprise at least one component in addition to the antibody molecule. Thus pharmaceutical compositions may comprise, in addition to the anti-C-MET antibody molecule, a pharmaceutically acceptable excipient, carrier, buffer, stabilizer or other materials well known to those skilled in the art. Such materials should be non-toxic and should not interfere with the efficacy of the anti-C-MET antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-C-MET antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringe's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-C-MET antibody molecule may be administered alone or in combination with other treatments, either simultaneously or sequentially dependent upon the condition to be treated.

An anti-C-MET antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-C-MET antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 μg to 1 g for systemic applications, and 1 μg to 1 mg for topical applications. An initial higher loading dose, followed by one or more lower doses, may be administered. Typically, the antibody will be a whole antibody, e.g. the IgG4(S228P) or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-C-MET antibody molecules as described herein may be administered as sub-cutaneous injections. Sub-cutaneous injections may be administered using an auto-injector, for example for long or short-term prophylaxis/treatment.

In some embodiments, the therapeutic effect of the anti-C-MET antibody molecule may persist for several multiples of the antibody half-life in serum, depending on the dose. For example, the therapeutic effect of a single dose of the anti-C-MET antibody molecule may persist in an individual for 1 month or more, 2 months or more, 3 months or more, 4 months or more, 5 months or more, or 6 months or more.

The invention also provides a method of producing an antibody molecule which specifically binds to human C-MET and optionally also to cynomolgus monkey C-MET or an antigen-binding portion thereof, comprising the steps of:
(1) grafting anti-C-MET CDRs from a non-human source into a human v-domain framework to produce a humanized anti-C-MET antibody molecule or antigen-binding portion thereof;
(2) generating a phage library of clones of the humanized anti-C-MET antibody molecule or antigen-binding portion thereof comprising one or more mutations in the CDRs;
(3) selecting the phage library for binding to human C-MET and optionally also to cynomolgus monkey C-MET;
(4) screening clones from the selection step (3) having binding specificity to human C-MET and optionally also to cynomolgus monkey C-MET; and
(5) producing an antibody molecule which specifically binds to human C-MET and optionally also to cynomolgus monkey C-MET, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

Refinements applicable to the above method are as described in Example 1 below.

As used herein, the term "C-MET" refers to the MET protein and variants thereof that retain at least part of the biological activity of C-MET. In some cases, as used herein, C-MET includes all mammalian species of native sequence C-MET, including human, rat, mouse and chicken. The term "C-MET" may be used to include variants, isoforms and species homologs of human C-MET. Antibodies of the invention may cross-react with C-MET from species other than human, in particular C-MET from cynomolgus monkey (Macaca fascicularis). Examples of human and cynomolgus C-MET amino acid sequences are provided in Table 12. In certain embodiments, the antibodies may be completely specific for human C-MET and may not exhibit non-human cross-reactivity.

As used herein, an "antagonist" as used in the context of the antibody of the invention or an "anti-C-MET antagonist antibody" (interchangeably termed "anti-C-MET antibody") refers to an antibody which is able to bind to C-MET and inhibit C-MET biological activity and/or downstream pathway(s) mediated by C-MET signalling. An anti-C-MET antagonist antibody encompasses antibodies that can block, antagonize, suppress or reduce (including significantly)C-MET biological activity, including downstream pathways mediated by C-MET signalling, such as receptor binding and/or elicitation of a cellular response to C-MET. For the purposes of the present invention, it will be explicitly understood that the term "anti-C-MET antagonist antibody" encompass all the terms, titles, and functional states and characteristics whereby C-MET itself, and C-MET biological activity, or the consequences of the activity or biological activity, are substantially nullified, decreased, or neutralized in any meaningful degree.

The antibody "specifically binds" "specifically interacts", "preferentially binds", "binds" or "interacts" with C-MET if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark and camelid antibodies), maxibodies, minibodies, intrabodies, diabodies, triabodies, tetrabodies, v-NAR and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody molecule, as used herein, refers to one or more fragments of an intact antibody that retain the ability to specifically bind to C-MET. Antigen binding functions of an antibody molecule can be performed by fragments of an intact antibody. Examples of binding fragments encompassed within the term "antigen binding portion" of an antibody molecule include Fab; Fab'; F(ab')2; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, CH2 and CH3. As is known in the art, an Fc region can be present in dimer or monomeric form.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, and contribute to the formation of the antigen binding site of antibodies. When choosing FR to flank CDRs, for example when humanizing or optimizing an antibody, FRs from antibodies which contain CDR sequences in the same canonical class are preferred.

The CDR definitions used in the present application combine the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 Aug. 2016]). The CDR definition used herein (a "Unified" definition) incorporates the lessons of all such prior insights and includes all appropriate loop positions required to sample the full residue landscape that potentially mediates target-binding complementarity.

Table 1 shows the amino acid sequences of the 224G11 murine anti-C-MET antibody CDRs as defined herein (a "Unified" scheme), in comparison to well-known alternative systems for defining the same CDRs.

As used herein the term "conservative substitution" refers to replacement of an amino acid with another amino acid which does not significantly deleteriously change the functional activity. A preferred example of a "conservative substitution" is the replacement of one amino acid with another amino acid which has a value ≥0 in the following BLOSUM 62 substitution matrix (see Henikoff & Henikoff, 1992, PNAS 89: 10915-10919):

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4. |

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')2 or other antigen-binding sub-sequences of antibodies) that contain minimal sequence derived from non-human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody or fully human antibody" refers to an antibody molecule, or antigen-binding portion thereof, derived from transgenic mice carrying human antibody genes or from human cells.

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to C-MET, which is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a Biacore® system.

The term "potency" is a measurement of biological activity and may be designated as $IC_{50}$, or effective concentration of an antibody or antibody drug conjugate to the antigen C-MET to inhibit 50% of activity measured in a C-MET activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to C-MET.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neoadjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation of Optimized Anti-C-MET Therapeutic Antibodies

Introduction

In this example, we successfully generate a panel of antagonistic, optimized anti-C-MET antibodies. These anti-C-MET antibodies are well expressed, biophysically stable, highly soluble and of maximized amino acid sequence identity to preferred human germlines.

Materials and Methods

C-MET Library Generation and Selection

The C-MET Fab repertoire was assembled by mass oligo synthesis and PCR. The amplified Fab repertoire was then cloned via restriction-ligation into a phagemid vector, transformed into E. coli TG-1 cells, and the phage repertoire rescued essentially as previously described in detail (Finlay et al., 2011, Methods Mol Biol 681: 383-401).

Phage selections were performed by coating streptavidin magnetic microbeads with biotinylated C-MET target protein (either human or cyno), washing the beads thrice with PBS and resuspending in PBS pH7.4 plus 5% skim milk protein. These beads were coated at 100 nM target protein in round 1 of selection, followed by reduced antigen concentrations in three successive rounds. In each round, phage were eluted using trypsin before re-infection into TG1 cells.

Periplasmic Extracts Production (Small-Scale)

Production of soluble Fabs in individual E. coli clones was performed. E. coli TG1 cells in logarhythmic growth phase were induced with isopropyl 1-thio-β-D-galactopyranoside. Periplasmic extracts containing soluble Fab were generated by a freeze/thaw cycle: Bacterial cell pellets were frozen at −20° C. for overnight and then thawed at room temperature and resuspended in PBS pH 7.4. The supernatants containing the soluble Fab were collected after shaking at room temperature and centrifugation.

IgG Expression and Purification

Mammalian codon-optimized synthetic genes encoding the heavy and light chain variable domains of the lead panel anti-C-MET antibodies plus the h224G11 and grafted (Graft) were cloned into mammalian expression vectors comprising IgG4(S228P) ('IgG4(S228P)'; human IgG4 containing S228P mutation in the hinge that stabilises the tertiary structure of the molecule) and human $C_K$ domains, respectively. Co-transfection of heavy and light chain containing vector in mammalian expression system was performed, followed by protein A-based purification of the IgG, quantification and QC on denaturing and non-denaturing SDS-PAGE.

Direct Binding ELISA for Fab and IgG

Binding and cross-reactivity of the lead panel to the recombinant proteins was initially assessed by binding ELISA. The human C-MET human Fc tagged recombinant protein and the cynomolgus monkey C-MET human Fc tagged recombinant protein were coated to the surface of MaxiSorp™ flat-bottom 96 well plate at 1 µg/ml. The purified IgG samples were titrated in two fold serial dilutions starting from 500 nM to 0.98 nM and allowed to bind to the coated antigens. The Fabs were detected using mouse anti-c-myc antibody followed by donkey anti-mouse IgG conjugated to horseradish peroxidase. The IgGs were detected using the mouse anti-human IgG conjugated to horseradish peroxidase. Binding signals were visualized with 3,3',5,5'-Tetramethylbenzidine Substrate Solution (TMB) and the absorbance measured at 450 nm. IgG binding analysis via ELISA on negatively charged biomolecular surfaces to calculate off-target binding and PK risk were performed as previously described (see Avery et al., 2018, MAbs 10 (2), 244-255).

Alphascreen Epitope Competition Assay for IgG4(S228P) Antibodies

The AlphaScreen assay (Perkin Elmer) was performed in a 25 µl final volume in 384-well white microtiter plates (Greiner). The reaction buffer contained 1×PBS pH 7.3 (Oxoid, Cat. nr. BR0014G) and 0.05% (v/v) Tween® 20 (Sigma, Cat. nr. P9416). Purified IgG samples were titrated in three fold serial dilutions starting at 50 nM final concentration and incubated with biotinylated human C-MET-His (Acrobiosystems) at 1 nM final concentration for 20 minutes at room temperature. The parental IgG and the anti-human IgG4(S228P) Acceptor beads at were added and the mix was incubated for 1 hour at room temperature. Followed by addition of the Streptavidin Donor beads and incubation for 30 minutes at room temperature. The emission of light was measured in the EnVision multilabel plate reader (Perkin Elmer) and analysed using the EnVision manager software. Values were reported as Counts Per Second (CPS) and corrected for crosstalk.

Biacore® analyses of IgG affinity for monomeric human and cyno C-MET in solution Affinity (KD) of purified IgGs was determined via SPR with antigen in-solution on a Biacore® 3000 (GE). A mouse anti-human antibody (CH1 specific) was immobilized on a CM5 Sensor Chip to a level of 2000 RU in acetate buffer at pH 4.5 using amine coupling following the Wizard instructions for two channels. One channel was used for background signal correction. The standard running buffer HBS-EP pH 7.4 was used. Regeneration was performed with a single injection of 10 µl of 10 mM Glycine at pH 1.5 at 20 µl/minute. IgG samples were injected for 2 minutes at 50 nM at 30 µl/min followed by and off-rate of 60 seconds. The monomeric antigen (human C-MET His tagged or cynomolgus monkey C-MET His tag) was injected in two fold serial dilutions from 100 nM down to 6 nM, for 2 minutes at 30 µl/min followed by an off-rate of 300 seconds. The obtained sensorgrams were analysed using the Biacore® 3000 evaluation (BIAevaluation) software. The KD was calculated by simultaneous fitting of the association and dissociation phases to a 1:1 Langmuir binding model.

Flow Cytometry of IgGs

Purified IgGs were tested in FACs for binding to human and cyno C-MET expressed on CHO-K1 stable cell lines and CHO-K1 wild-type cells. The IgG samples were titrated in three-fold serial dilutions starting at 500 nM to 0.08 nM. Binding of IgGs was detected with a mouse anti-human IgG conjugated to FITC. Results were analyzed by examining the Mean Fluorescence Intensity (MFI) of 10000 cells per sample in the BL-1 channel detector of a flow cytometer (Attune™ NxT Acoustic Focusing Cytometer, Invitrogen/ThermoFisher Scientific). The EC50 values were calculated using the MFI values in GraphPad Prism software (GraphPad Software, La Jolla, CA) and 4 parameters.

Antibody v-Domain T Cell Epitope Content: In Silico Analyses

In silico technologies (Abzena, Ltd.), which are based on identifying the location of T cell epitopes in therapeutic antibodies and proteins, were used for assessing potential immunogenicity in antibody v-domains. iTope™ was used to analyse the VL and VH sequences of key leads for peptides with promiscuous high affinity binding to human MHC class II. Promiscuous high affinity MHC class II binding peptides are thought to correlate with the presence of T cell epitopes that are high risk indicators for clinical immunogenicity of drug proteins. The iTope™ software predicts favourable interactions between amino acid side chains of a peptide and specific binding pockets (in particular pocket positions; p1, p4, p6, p7 and p9) within the open-ended binding grooves of 34 human MHC class II alleles.

These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. This process successfully discriminates with high accuracy between peptides that either bind or do not bind MHC class II molecules.

In addition, the sequences were analysed using TCED™ (T Cell Epitope Database™) search for matches to T cell epitopes previously identified by in vitro human T cell epitope mapping analyses of other protein sequences. The TCED™ is used to search any test sequence against a large (>10,000 peptides) database of peptides derived from unrelated protein and antibody sequences.

Differential Scanning Calorimetry (DSC) Analysis

The Tm of test articles was analysed using a MicroCal PEAQ-DSC (Malvern Instruments, Malvern, UK) running version 1.22 software. The samples were heated at a rate of 200° C./hour over a range of 20-110° C. Thermal data was normalised based on protein concentration. The Tm of the protein was determined from the heating scan data.

Charge Variant Assay

Charge variant profiling of test articles was determined by Protein Charge Variant Assay on a LabChip GXII Touch HT (PerkinElmer, Beaconsfield, UK), according to the manufacturer's protocol.

Isoelectric Focusing assay IEF analysis for the lead IgG4 (S228P) proteins was performed to assess possible differences in pI. Electrophoresis was performed using an Invitrogen™ Novex™ pH 3-10 IEF Protein Gel, using Novex™ IEF Sample Buffer pH 3-10, Novex™ IEF Anode and Cathode Buffers. pI values were estimated based on the IEF pI marker values (Serva). Brentuximab and Infliximab IgG1s were included as controls.

Results and Discussion

CDR Grafting onto Preferred Human Germline v-Genes

The CDRs of an antagonistic murine anti-C-MET IgG 224G11 (224G11; see WO2011151412A1 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds IGHV1-46 and IGKV3-20, which are known to have good solubility, high physical stability and are used at high frequency in the expressed human antibody repertoire.

Those scaffolds and grafted CDR definitions are outlined in Table 2. The heavy and light chain sequences for chimeric anti-C-MET antibody m224G11 and humanized h224G11 are also shown in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. The IGHV1-46/IGKV3-20 graft was therefore taken forward as the template for CDR mutagenesis and selection of improved clones.

Library Generation and Screening

The CDR-grafted IGKV3-20/IGHV1-46 v-domain sequences were combined into a Fab phage display format and a mutagenesis library cassette was generated by oligo synthesis and assembly. The final Fab library was ligated into a phage display vector and transformed into E. coli via electroporation to generate $2.5 \times 10^9$ independent clones. Library build quality was verified by sequencing 96 clones, across both v-domains. This sequencing data showed that the positions encoding either the murine or human germline residue at each position of variance had been effectively sampled at a frequency of approximately 50% (or e.g. 33% in positions where 3 amino acids where encoded). Libraries were rescued using helper phage M13 and selections performed on biotinylated human and cynomolgus monkey C-MET-Fc proteins in multiple separate branches.

Figure 1B:
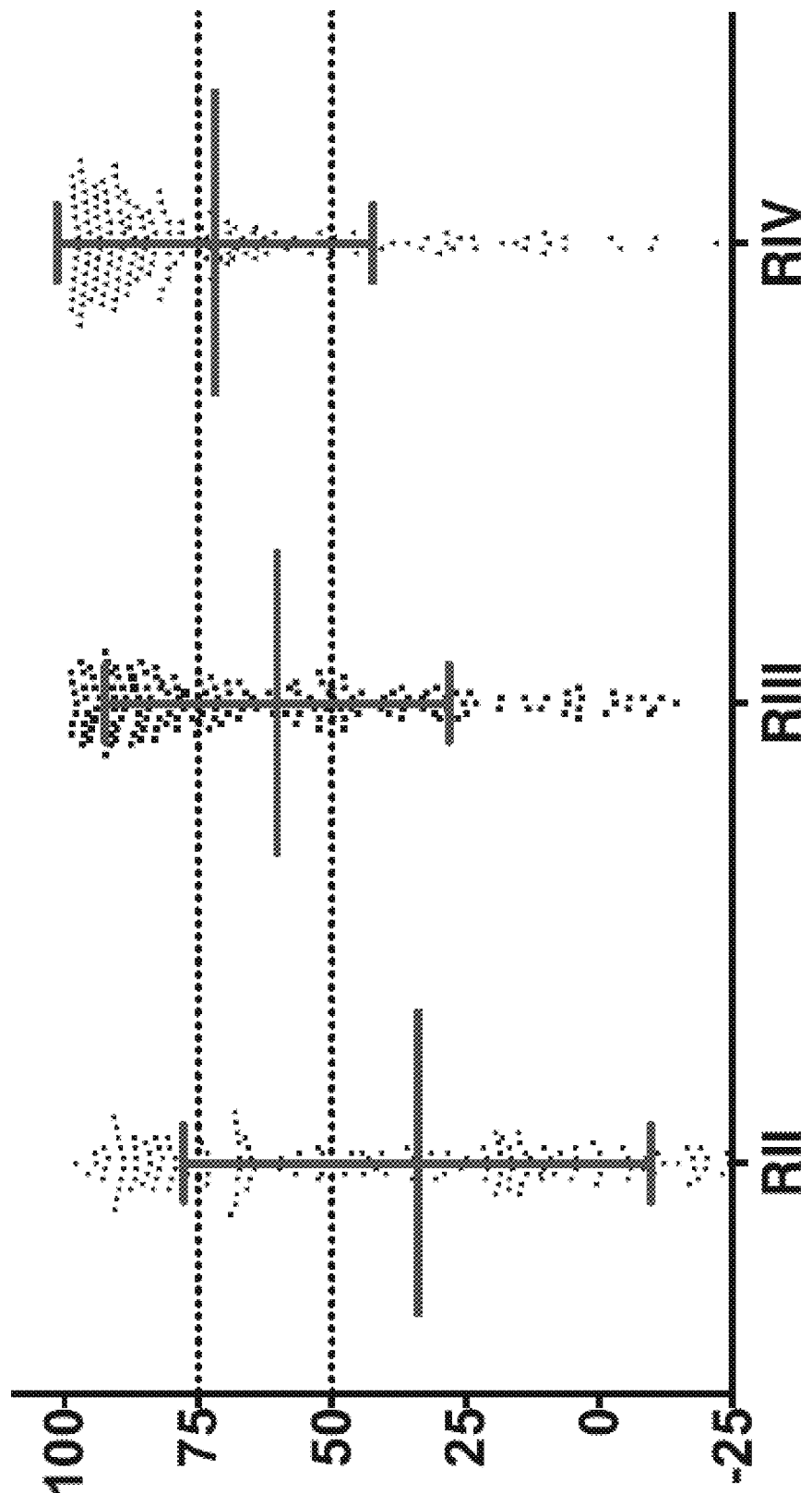

Post-selection screening and DNA sequencing revealed the presence of 131 unique, human and cyno C-MET-binding Fab clones that exhibited strong binding to human and cyno C-MET in ELISA (FIG. 1A) and >50% inhibition of 224G11 IgG4(S228P) binding to human C-MET in Alphascreen assay (FIG. 1B). Amongst these 131 clones, the framework sequences remained fully germline while humanizing mutations were also observed in all CDRs (Table 3). Lead clones were ranked based on level of CDR germlining versus ELISA and Alphascreen signals for binding to both human and cyno C-MET-Fc. The v-domains of the 9 top clones from this ranking were then sub-cloned into IgG expression vectors for further testing as below (Table 4).

While germ-lining mutations were observed in all CDRs for the lead clones derived directly from library selections, it remained possible that sequence analyses might allow further clones to be designed to have maximal humanization. The 131 sequence-unique hits with binding signals against human and cyno protein were therefore used to analyse the retention frequency for murine amino acids in the CDRs of this functionally characterized population.

Figure 2A:
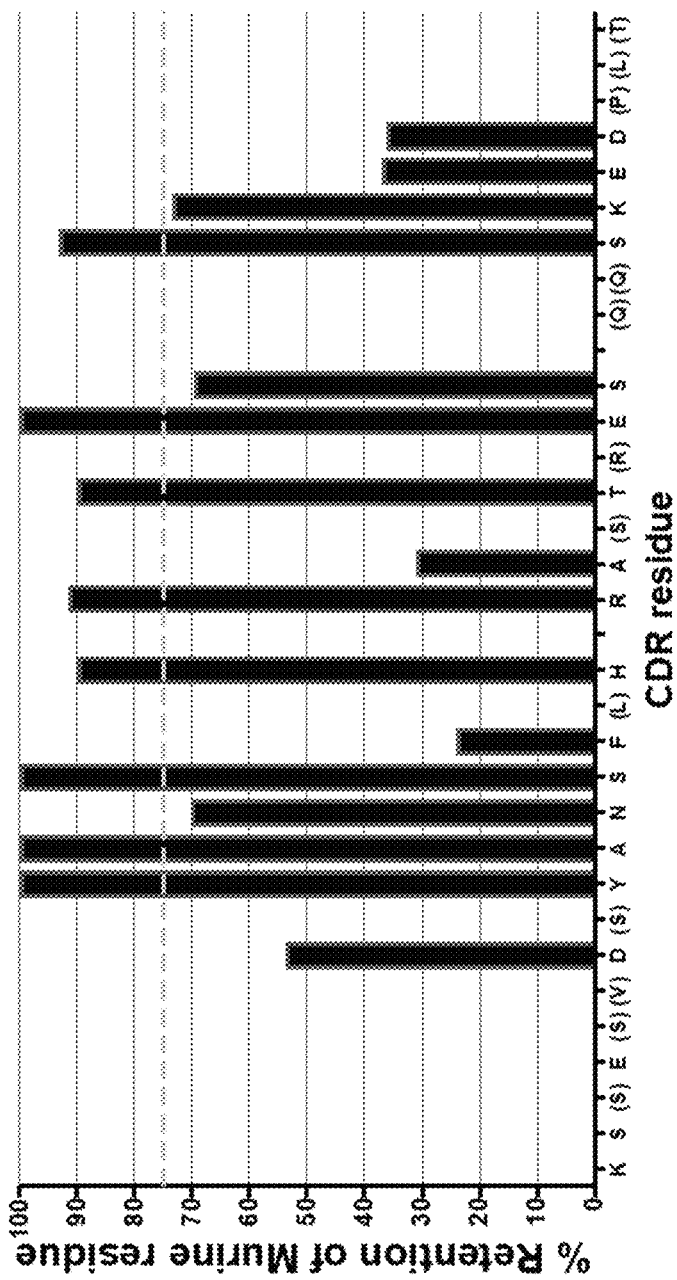
FIG. 2A-FIG. 2B. Analysis of CDR residue tolerance for mutation to germline. A plot of murine amino acid retention frequencies in the CDRs of the ELISA-positive population of 131 unique Fab clones that demonstrated human and cyno CMET cross-reactivity is shown for VL (SEQ ID NOs: 58-60) (FIG. 2A) and VH (SEQ ID NOs: 61-63) (FIG. 2B) domains, respectively. Only those residues targeted for human/murine residue mutagenesis are plotted, other than in the HCDR3. CDR residues noted in parentheses on the X-axes were identical to those found in the human germlines used for grafting (IGKV3-20 and IGHV1-46). Those residues in the CDRs that are not in parentheses, but whose values are set at 0, were mutated to human germline during the grafting process. In both plots the dashed line in grey at 75% represents the cut off for tolerance of murine residue replacement by human germline.
Figure 2B:
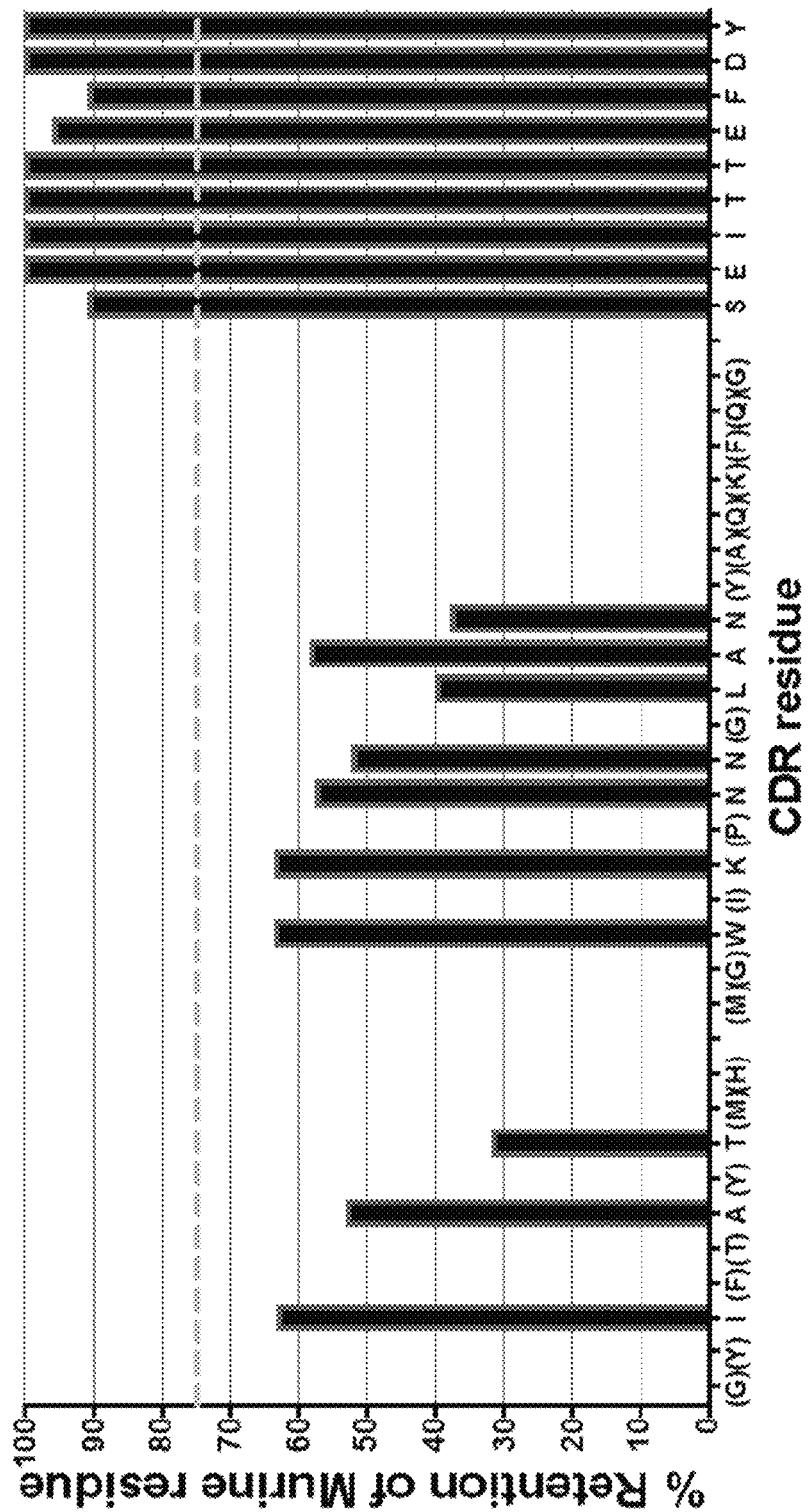

Positional amino acid retention frequency was expressed as a percentage found in the VL and VH domains (FIGS. 2A & B, respectively). Murine residues with RF <75% were regarded as positions that are possibly not essential to the target-binding paratope and are likely to be open to germ-lining, in a series of combinatorial designs (Table 4). In a surprising finding, none of the 10 murine residues in the HCDR1 and HCDR2 exhibited retention frequency above 75% (FIG. 2A). This analysis strongly suggested that the entire VH sequence outside the HCDR3 could possibly be rendered germline identity to IGHV1-46. In the $V_L$ domain, in contrast, 8 of 16 murine CDR residues derived from the h224G11 sequence were retained with frequencies >75% (FIG. 3A).

Designs containing combinations of those murine residues with RF >75% were given the prefix "MH" (MH=Maximally Humanized). In total 4 designer $V_H$ and 3 designer $V_L$ domains were generated. These constructs were co-transfected in a matrixed fashion to create 12 final designer IgGs in total (Table 4). The MH and library-derived clone v-domains were generated by gene synthesis and (along with the control antibodies), cloned into human expression vectors for production in IgG4(S228P) format. All IgGs were readily expressed and purified from transient transfections of mammalian cells.

Lead IgG Specificity and Potency Characteristics

Figure 3A:
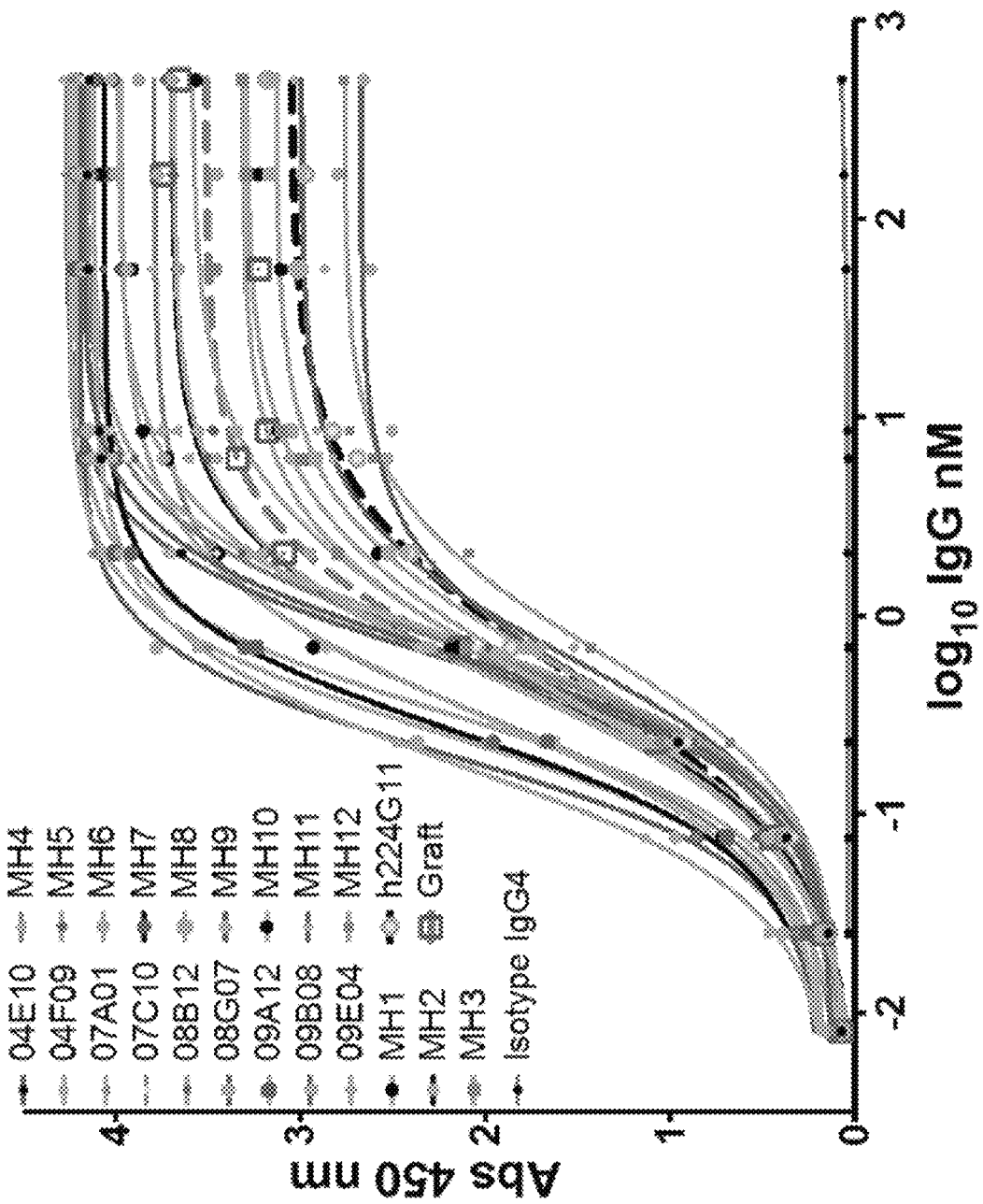
FIG. 3A-FIG. 3B. Direct titration ELISA for IgG binding to human and cyno C-MET-Fc proteins. Humanized h224G11, Grafted clone (Graft), library-derived and designer clones in human IgG4(S228P) format were titrated (in nM) in a direct binding ELISA against human (FIG. 3A) and cyno (FIG. 3B)C-MET-Fc proteins. All clones other than Isotype IgG4 control demonstrated binding activity against both orthologs of C-MET, with approximately equivalent or improved human and cyno C-MET binding.
Figure 3B:
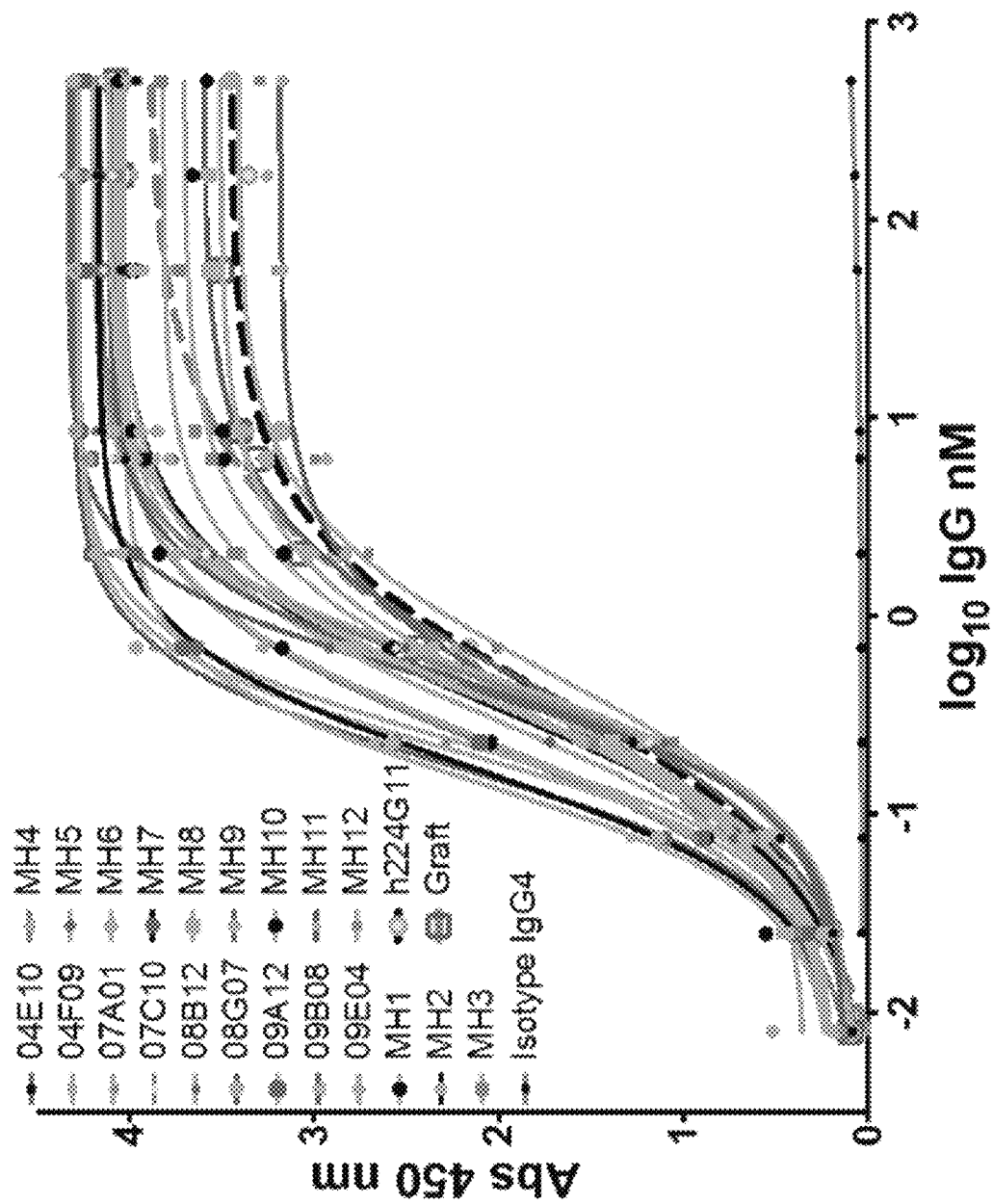

The purified IgGs described above were then tested for binding to human and cyno C-MET-Fc in direct titration ELISA format (FIGS. 3A & B). This analysis demonstrated that all library derived and designer (MH) clones retained binding activity for human and cyno C-MET that was equivalent to, or improved over, the h224G11 IgG4(S228P).

Figure 4:
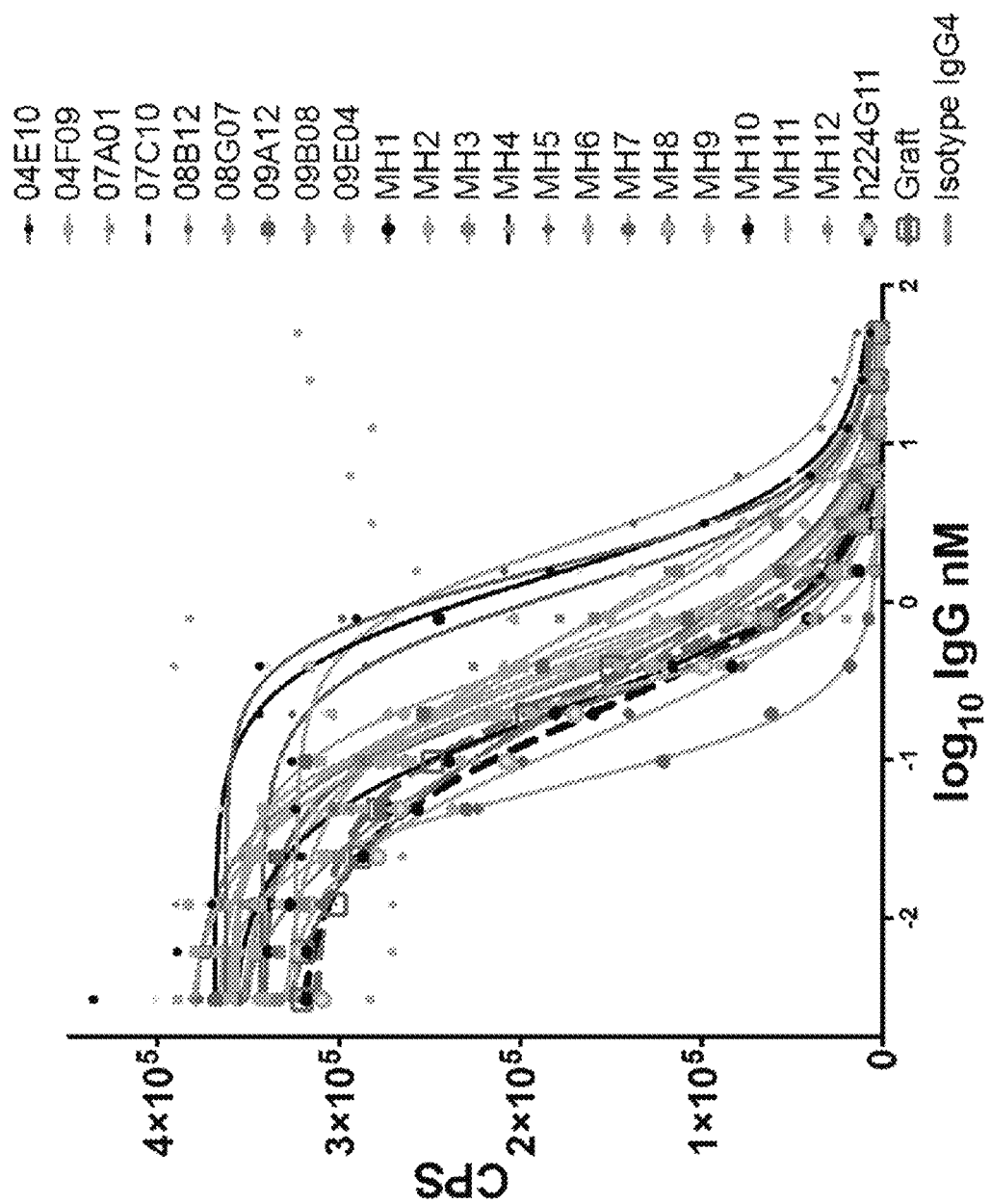
FIG. 4. Epitope competition analysis of IgG4(S228P) proteins in Alphascreen. Anti-C-MET IgG4(S228P) clones were applied in an epitope competition assay using Alphascreen technology. In this assay, library-derived and designer IgGs were analysed for their retention of the parental 224G11 epitope by competing for 224G11 IgG4 (S228P) binding to human C-MET protein, in solution. All clones analysed showed strong, concentration-dependent neutralisation of 224G11 binding to C-MET.

An Alphascreen assay was established to allow the testing of IgGs for epitope competition with h224G11 IgG binding to biotinylated monomeric human C-MET. In this assay, the top-performing library-derived and designer IgGs were more effectively differentiated. While all clones exhibited full, concentration-dependent neutralisation, and the majority of clones exhibited equivalent or improved competition for the h224G11 epitope over h224G11 (FIG. 4), some exhibited less potent epitope competition including: 08B12, 04E10, 09B08, 07C10.

Biacore® analyses of binding affinity were performed for all IgGs to solution-phase, monomeric human and cyno C-MET proteins. In all cases, accurate 1:1 binding affinities with low Chi$^2$ values were obtained (Table 5). These analyses showed that library-derived clones which consistently gave the highest EC50 and IC50 values in Fab and IgG ELISA and Alphascreen assays also showed highest affinity binding to human and cyno C-MET. Unexpectedly, library-derived clones 08G07, 04F09, 09E04, 07A01 and designer clones MH4 and MH7 all exhibited significantly improved binding affinities for human C-MET in comparison to h224G11 (Table 5). Importantly, these improvements in affinity were recapitulated in cyno binding, with each of these clones exhibiting affinities within 2-fold of the human C-MET affinity. Affinity differentials of less than 3-fold between human and cyno target orthologs are highly beneficial in pre-clinical drug development analyses as they allow significantly better design and interpretation of e.g. monkey safety, PK and PD modelling experiments. The Biacore® analyses also showed that the reduced epitope competition potency observed for clones 08B12, 04E10, 09B08, 07C10 in the Alphascreen assay (FIG. 4) was driven by reduced human C-MET binding affinity, rather than any alteration in binding epitope.

In addition, comparison of the affinities of MH clones confirmed the influence of the LCDR3 in maintaining binding affinity, as mutations of the residues 'SK' at positions 3 and 4 both resulted in approximately 10 to 20-fold loss of KD for clones MH8 and MH9 in comparison to clone MH7, against both human and cyno C-MET (Table 5). Comparison of clones MH4 and MH10 also confirmed that the mutation of HCDR1 residue 8 (T to A) led to an approximately 2-fold reduction in binding affinity for human C-MET in clone MH10, but no significant reduction in affinity for cyno C-MET (Table 5). Importantly, however, this T>A mutation in clone MH10 rendered the HCDR1 fully germline for the human germline sequence IGHV1-3. As IGHV1-3 and IGHV1-46 are sequence-identical 10 amino acids in either N or C-terminal directions from the T>A mutation, this rendered the HCDR1 sequence fully deimmunised for human t cell epitopes due to thymic tolerance (human t-cell epitopes being based on core 9-mer amino acid sequence).

The findings outlined above confirmed that the MH7 clone could fully retain (and improve over) the binding affinity, epitope specificity and species cross-reactivity of h224G11, while retaining only a single non-germline amino acid in the VH domain (excluding the HCDR3, for which there is no corresponding germline). In addition, the fully germlined HCDR2 of MH7 removed 3 potential amino acid development liability sequences found in the h224G11 antibody: A putative oxidation risk at position 3 (VW, plus two deamidation risk motifs at positions 7 and 8 (both N). In the light chain of MH7, three additional development liability sequences found in h224G11 were removed: a 'DS' aspartic acid isomerisation motif in LCDR1 position 7, and oxidation risk at LCDR1 position 13 (F) and a 'DP' acid hydrolysis motif in LCDR3 at position 6. These improvements in primary sequence are of direct consequence in both manufacturing and clinical development of an antibody therapeutic as they are all potential protein degradation risk motifs, leading to intrinsic product heterogeneity. Such risk motifs can lead to costly development issues where multiple process modifications must be made to maximise intact antibody yield and to minimise product heterogeneity. Degradation motifs are also a clinical development risk, as accelerated antibody breakdown in the body can reduce both half-life and potency of the molecule.

Flow Cytometric Analyses of Lead IgG Binding Specificity at the Cell Membrane

Figure 5A:
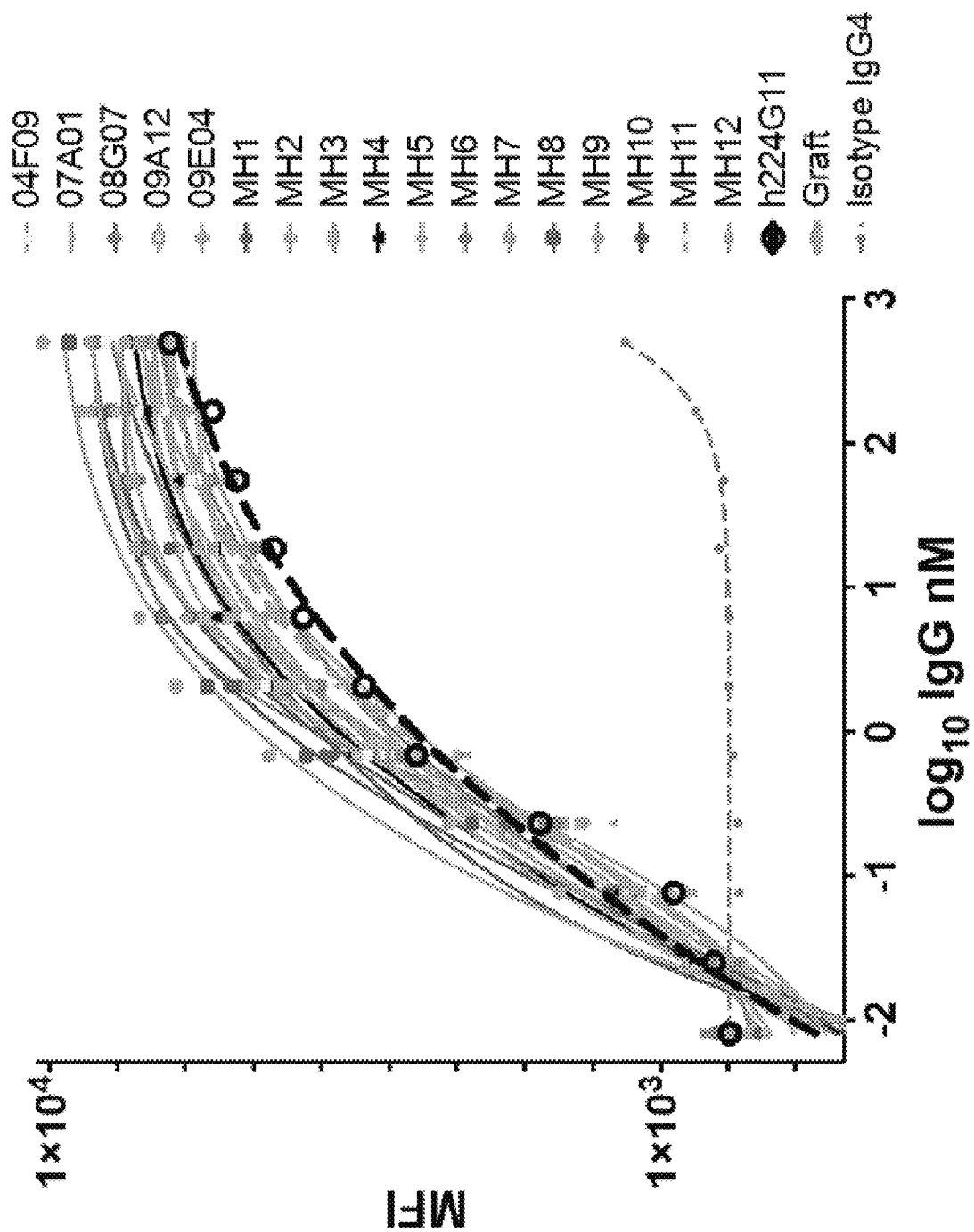
FIG. 5A-FIG. 5B. Flow cytometric binding to human and cyno C-MET+ CHO-K1 cells for library-derived and primary designer leads. Anti-C-MET controls h224G11 and Graft, library-derived and designer leads in IgG4(S228P) format were examined for specific binding on human C-MET-transfected CHO-K1 cells (FIG. 5A) and cyno C-MET-transfected CHO-K1 cells (FIG. 5B). IgGs were tested at concentrations ranging from 500-0.08 nM. Concentration-dependent binding was observed against both human and cyno cell lines for all C-MET-specific antibodies but not isotype control IgG4.
Figure 5B:
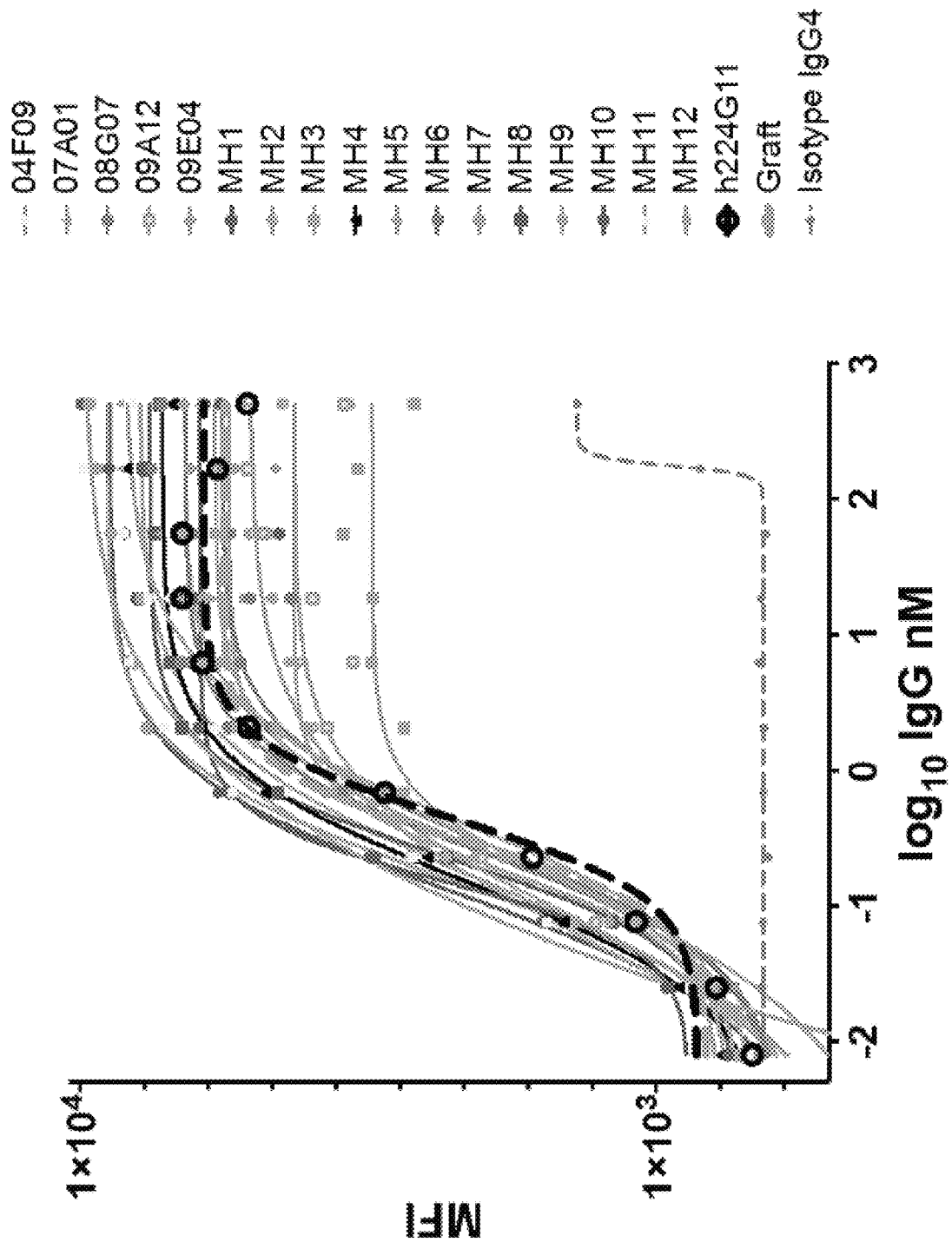

Antibodies to C-MET were analysed for concentration-dependent binding at the cell surface via flow cytometry. CHO-K1 cells were stably transfected with either human or cyno C-MET full-length cDNAs. Anti-C-MET IgGs and an isotype control IgG4(S228P) were then all tested in IgG4(S228P) format, over a concentration range of 500-0.08 nM for binding to human (FIG. 5A) and cyno (FIG. 5B) CHO-K1 cells. All IgGs other than the isotype control showed concentration-dependent binding to human and cyno C-MET+ cells, equivalent to, or improved over h224G11, with a maximum MFI in each case being >10-fold higher than observed background signals for Isotype IgG4. Several clones, including MH1, MH4, MH7 and MH10 exhibited stronger binding profiles and improved EC50 values for binding to both human and cyno+ CHO-K1 cells, in comparison to h224G11 (Table 6).

Antibody v-Domain T Cell Epitope Analyses

In silico technologies (Abzena, Ltd.), which are based on identifying the location of T cell epitopes in therapeutic antibodies and proteins, were used for assessing the immunogenicity of both the h224G11 and lead antibody v-domains. Analysis of the v-domain sequences was performed with overlapping 9mer peptides (with each overlapping the last peptide by 8 residues) which were tested against each of the 34 MHC class II allotypes. Each 9mer was scored based on the potential 'fit' and interactions with the MHC class II molecules. The peptide scores calculated by the software lie between 0 and 1. Peptides that produced a high mean binding score (>0.55 in the iTope™ scoring function) were highlighted and, if >50% of the MHC class II binding peptides (i.e. 17 out of 34 alleles) had a high binding affinity (score >0.6), such peptides were defined as 'high affinity' MHC class II binding peptides which are considered a high risk for containing CD4+ T cell epitopes. Low affinity MHC class II binding peptides bind a high number of alleles (>50%) with a binding score >0.55 (but without a majority >0.6). Further analysis of the sequences was performed using the TCED™. The sequences were used to interrogate the TCED™ by BLAST search in order to identify any high sequence homology between peptides (T cell epitopes) from unrelated proteins/antibodies that stimulated T cell responses in previous in vitro T cell epitope mapping studies performed at Abzena Ltd.

Peptides were grouped into four classes: High Affinity Foreign ('HAF'—high immunogenicity risk), Low Affinity Foreign ('LAF'—lower immunogenicity risk), TCED+ (previously identified epitope in TCED™ database), and Germline Epitope ('GE'—human germline peptide sequence with high MHC Class II binding affinity). Germline Epitope 9mer peptides are unlikely to have immunogenic potential due to T cell tolerance, as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic.

As shown in Table 7, the h224G11 v-domains sequences were found to contain significant foreign epitope risk despite having been humanized onto germline framework sequences. In the VL domain, h224G11 was found to contain two HAF peptide motifs ('LLIYRASTR' (SEQ ID NO: 91) and 'IYRASTRES' (SEQ ID NO: 92), both containing LCDR2 residues) and one LAF motif ('VAVYYCQQS' (SEQ ID NO: 93)). In the VH domain, h224G11 was also found to contain two HAF peptide motifs ('IFTAYTMH' (SEQ ID NO: 94), containing HCDR1 residues, and 'VYY-CARSEI' (SEQ ID NO: 95), containing HCDR3 residues) and one LAF motif ('MGWIKPNNG' (SEQ ID NO: 96), containing HCDR2 residues).

Key lead v-domains exhibited significant beneficial changes in peptide epitope content in comparison to h224G11 (Table 7). As the v-domain engineering process undertaken here had successfully selected for antibodies that maintained anti-MET potency without the need for many of the murine residues included in the CDRs of h224G11 (Table 2, Table 4), multiple HAF and LAF epitopes found in the v-domains of h224G11 were ablated in library-derived and designer leads, leading to reduced HAF and/or LAF content (Table 7). GE epitope content was also found to be significantly increased in the VH regions of lead clones, and TCED+ epitopes were not observed in any lead clone (Table 7). These findings were exemplified by the clone MH7, where the near-complete germlining of the VH domain CDRs 1 and 2 not only removed several development liability sequences (as described above), but also ablated the HAF peptide motif 'IFTAYTMHW' (SEQ ID NO: 97), and the LAF motif 'MGWIKPNNG' (SEQ ID NO: 96), while instating two new GEs that span the framework two and HCDR2 ('LEWMGIINP (SEQ ID NO: 97)' and 'MGI-INPSGG' (SEQ ID NO: 98)). Clone MH7 was therefore left with only a single potential foreign epitope in its VH domain (Table 7).

Importantly, it was observed that the extensive mutagenesis performed in the LCDR1, which removed development liability motifs in several leads (Table 4) did not generate any T cell epitope risk motifs. Multiple foreign epitopes found in the h224G11 VL sequence were also eliminated by germlining mutations found in the CDRs of lead clones. For example, a HAF peptide 'IYRASTRES' (SEQ ID NO: 92) found in the LCDR2 of h224G11 was found to be ablated in all lead clones that contained the mutation S>T at position 9 (Table 4). Similarly, a LAF peptide motif in the LCDR3 of h224G11 was ablated in the LCDR3 sequences 'QQYGSE-PLT' (SEQ ID NO: 53) and 'QQSKESPLT' (SEQ ID NO: 47), as found in multiple library-derived and designer clones (Table 4). As the clones MH7 and 07A01 both contained multiple CDR sequences with reduced immunogenic potential, and demonstrated maintained epitope specificity and affinity improvements over h224G11 (Table 5, FIG. 4), the findings above allowed the design of second-generation maximally deimmunised clones MH7-1, MH7-2 and MH7-3 (Table 7, Table 8). Clone MH7-3 not only improved the predicted immunogenicity of clone MH7, but also removed the final CDR amino acid liability motif (a deamidation risk site), by converting the amino acids 'NS' at positions 11 and 12 of LCDR1 with the motif 'QS' (Table 8).

Analyses of Second-Generation Designer Clones

Figure 6A:
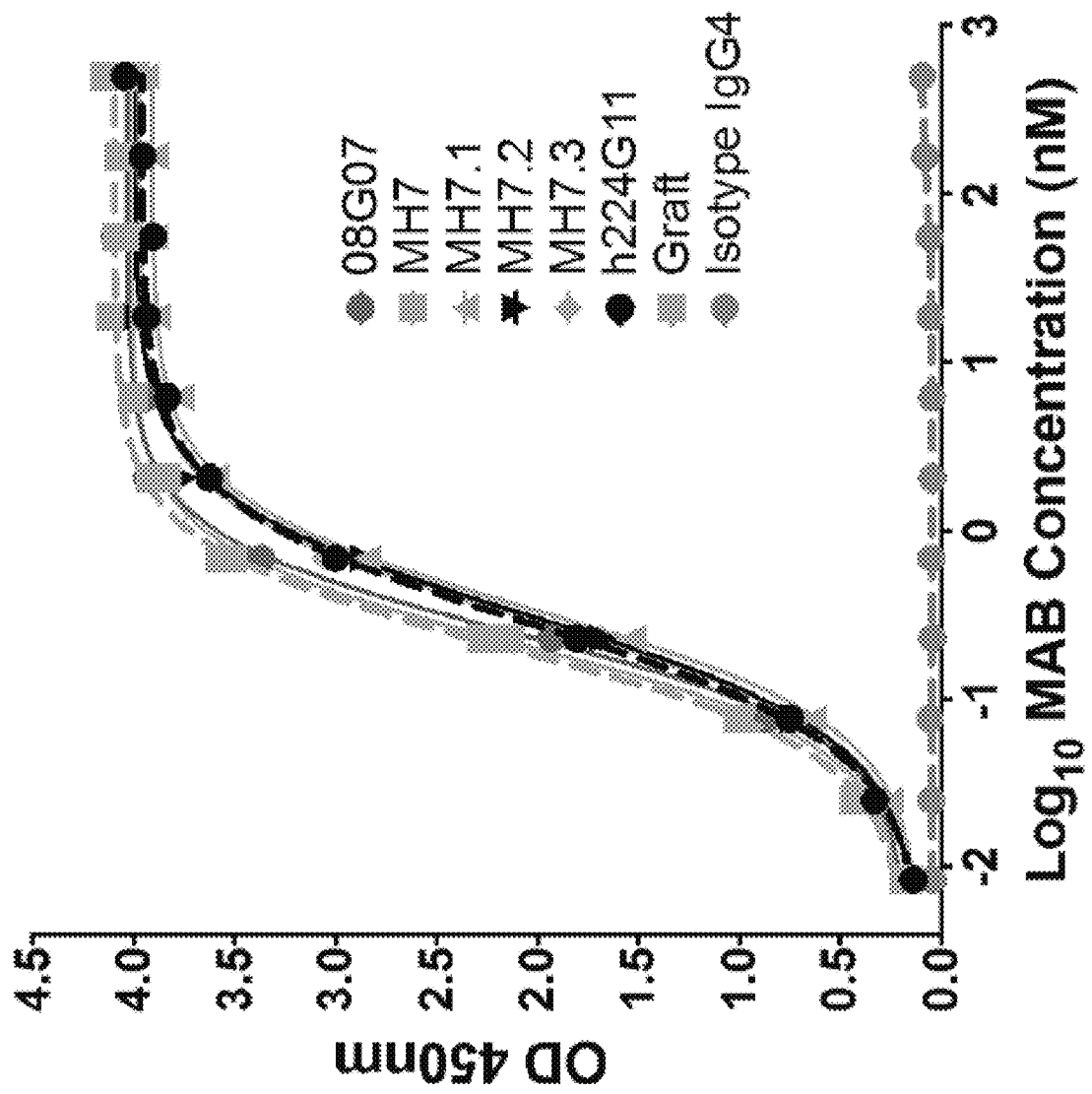
FIG. 6A-FIG. 6B. Direct titration ELISA for IgG binding to human and cyno C-MET-Fc proteins. Humanized h224G11, Grafted clone (Graft) and clones 08G07, MH7, MH7-1, MH7-2, MH7-3 in human IgG4(S228P) format were titrated (in nM) in a direct binding ELISA against human (FIG. 6A) and cyno (FIG. 6B)C-MET-Fc proteins. All clones other than Isotype IgG4 control demonstrated binding activity against both orthologs of C-MET, with approximately equivalent or improved human and cyno C-MET binding.
Figure 6B:
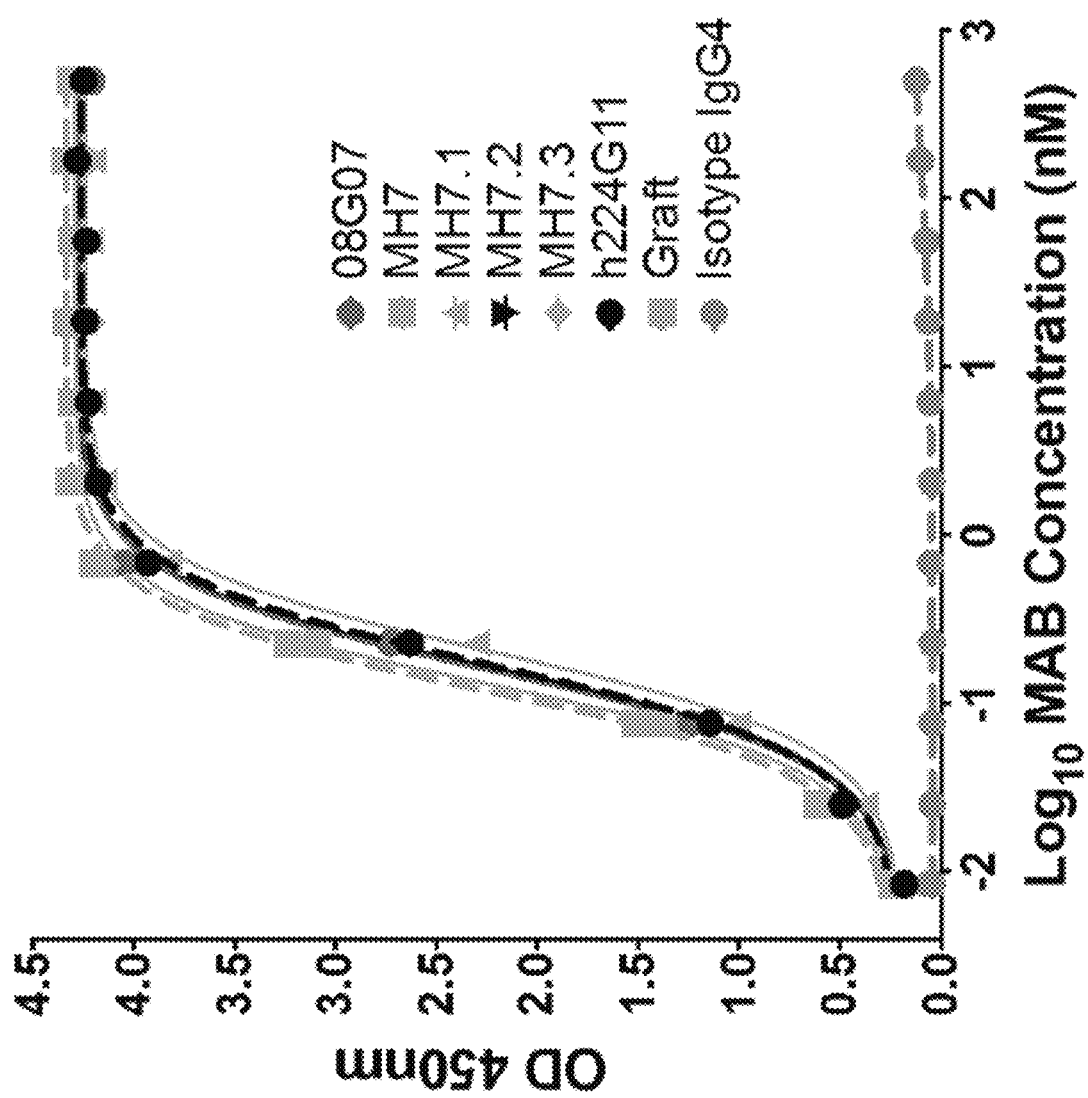

Clones MH7-1, MH7-2 and MH7-3 were readily expressed and purified as IgG4(S22P) and were then tested for binding to human and cyno C-MET-Fc in direct titration ELISA format (FIG. 6A, 6B). This analysis demonstrated that all 3 clones retained full binding activity for human and cyno C-MET that was equivalent to, or improved over, the h224G11, Grafted, MH7 and 08G07 IgG4(S228P) proteins.

Figure 7:
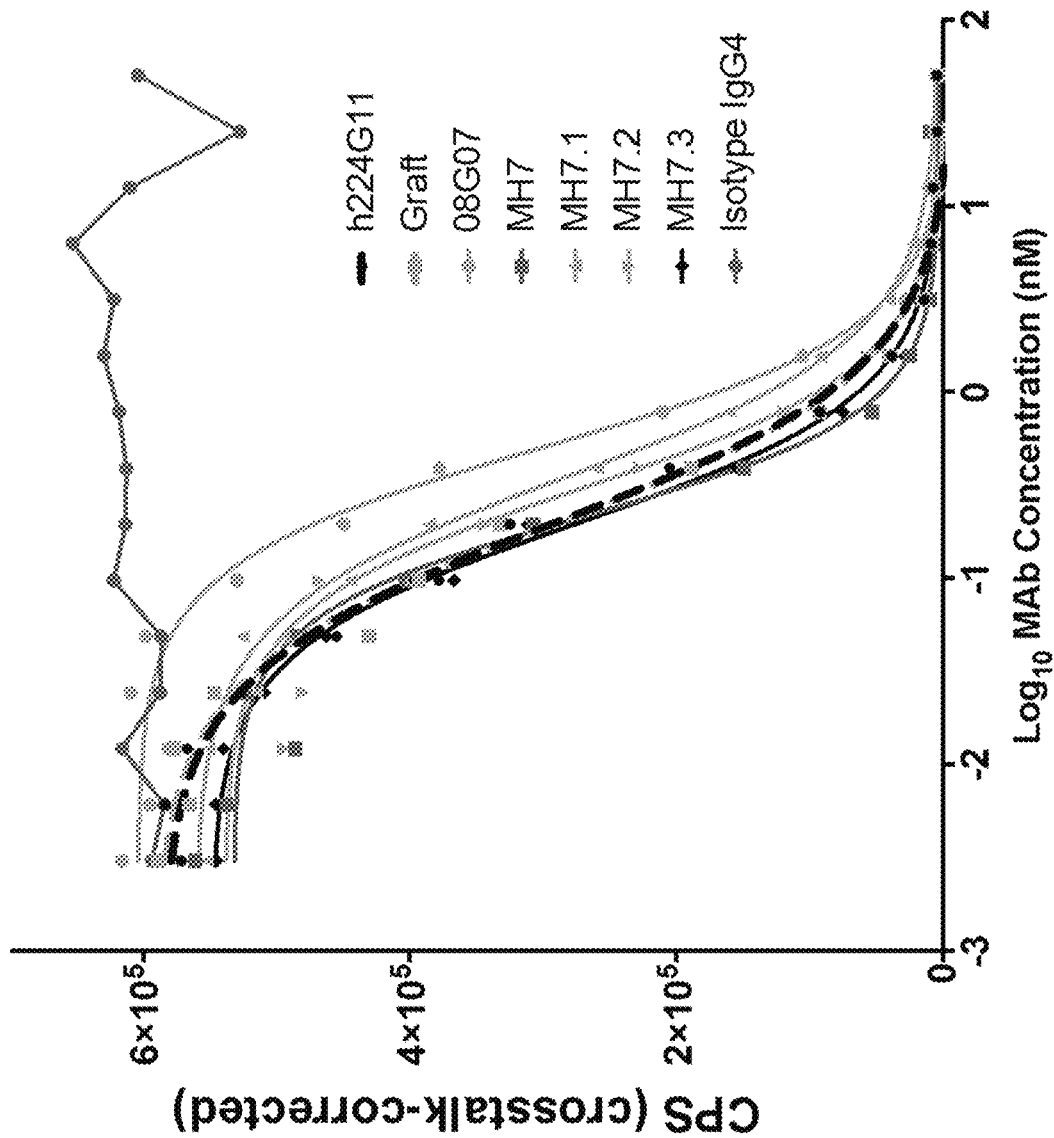
FIG. 7. Epitope competition analysis of IgG4(S228P) proteins in Alphascreen. Anti-Humanized h224G11, Grafted clone (Graft) and clones 08G07, MH7, MH7-1, MH7-2, MH7-3 in human IgG4(S228P) format were titrated (in nM) in an epitope competition assay using Alphascreen technology. In this assay, library-derived and designer IgGs were analysed for their retention of the parental 224G11 epitope by competing for 224G11 IgG4(S228P) binding to human C-MET protein, in solution. All clones analysed showed strong, concentration-dependent neutralisation of 224G11 binding to C-MET.

The Alphascreen assay, as described above, was then used to allow the testing of IgGs for epitope competition with h224G11 IgG binding to biotinylated monomeric human C-MET. This analysis demonstrated that all 3 clones retained full epitope reactivity that was equivalent to h224G11 (FIG. 7).

Figure 8A:
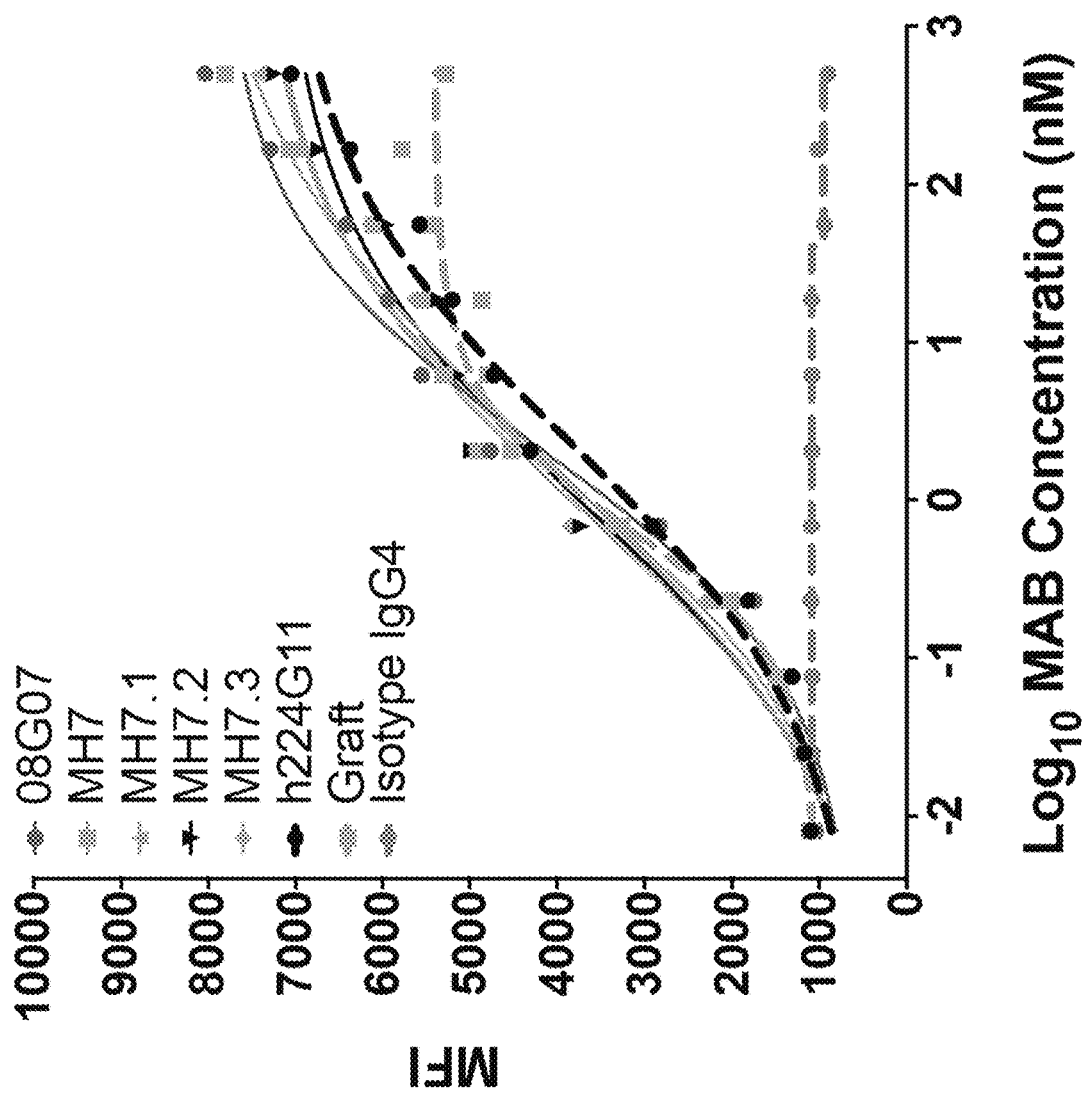
FIG. 8A-FIG. 8C. Flow cytometric binding to human and cyno C-MET+ CHO-K1 cells for library-derived and primary designer leads. Humanized h224G11, Grafted clone (Graft) and clones 08G07, MH7, MH7-1, MH7-2, MH7-3 in human IgG4(S228P) format were were examined for specific binding on human C-MET-transfected (FIG. 8A), cyno C-MET-transfected (FIG. 8B) and untransfected (FIG. 8C) CHO-K1 cells. IgGs were tested at concentrations ranging from 500-0.08 nM. Concentration-dependent binding was observed against both human and cyno cell lines for all C-MET-specific antibodies but not isotype control IgG4.
Figure 8B:
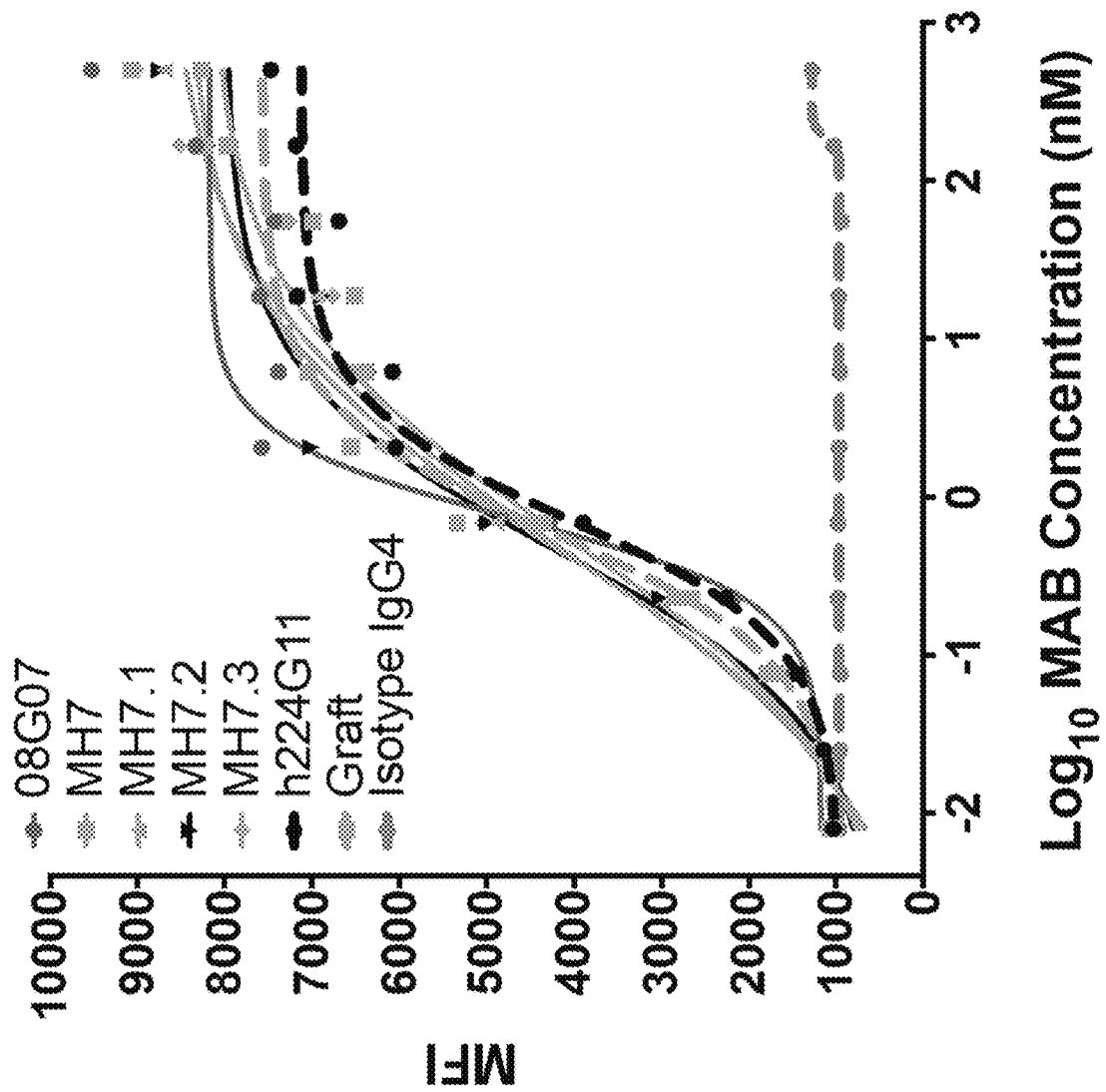
Figure 8C:
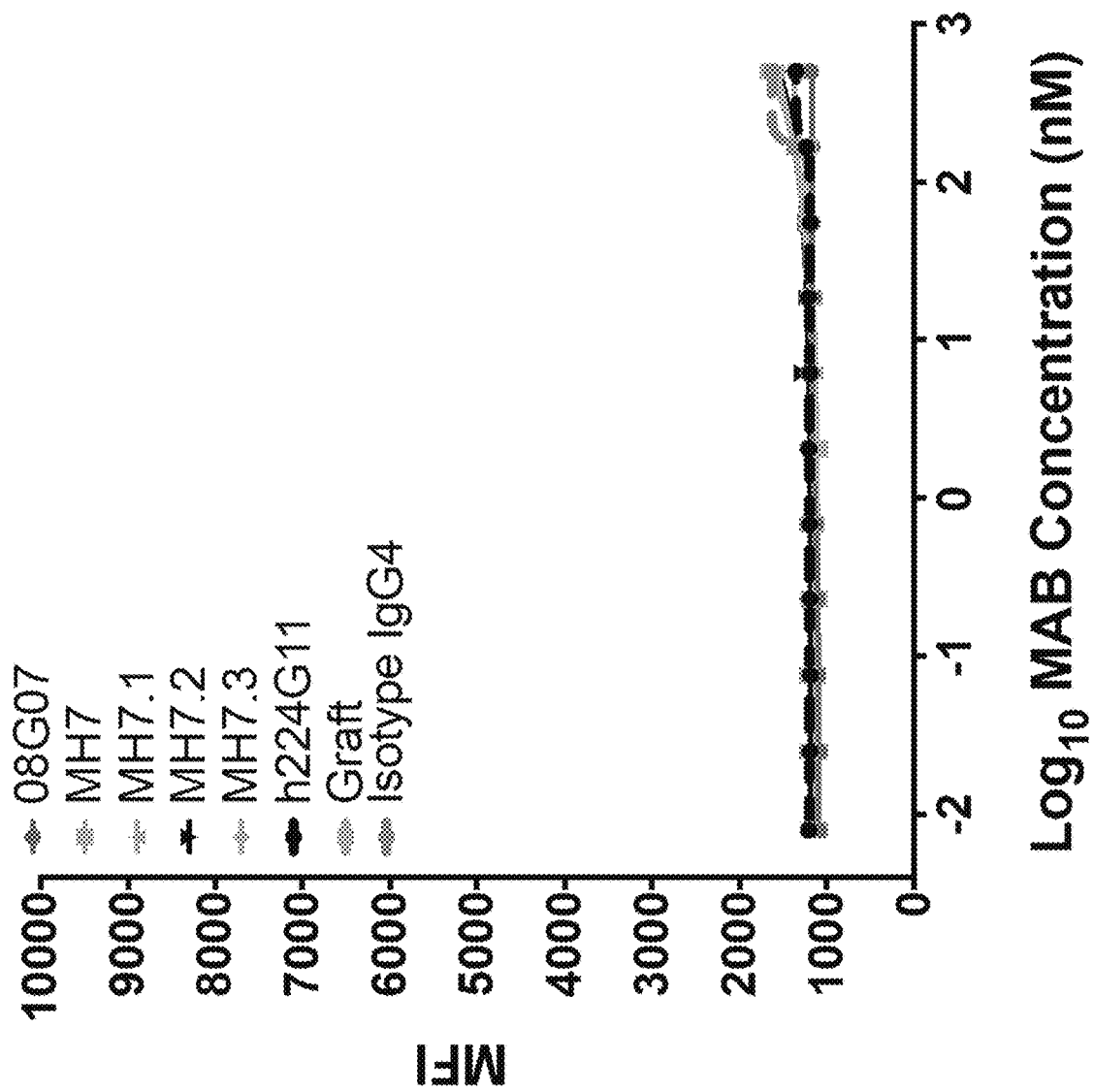
Figure 9:
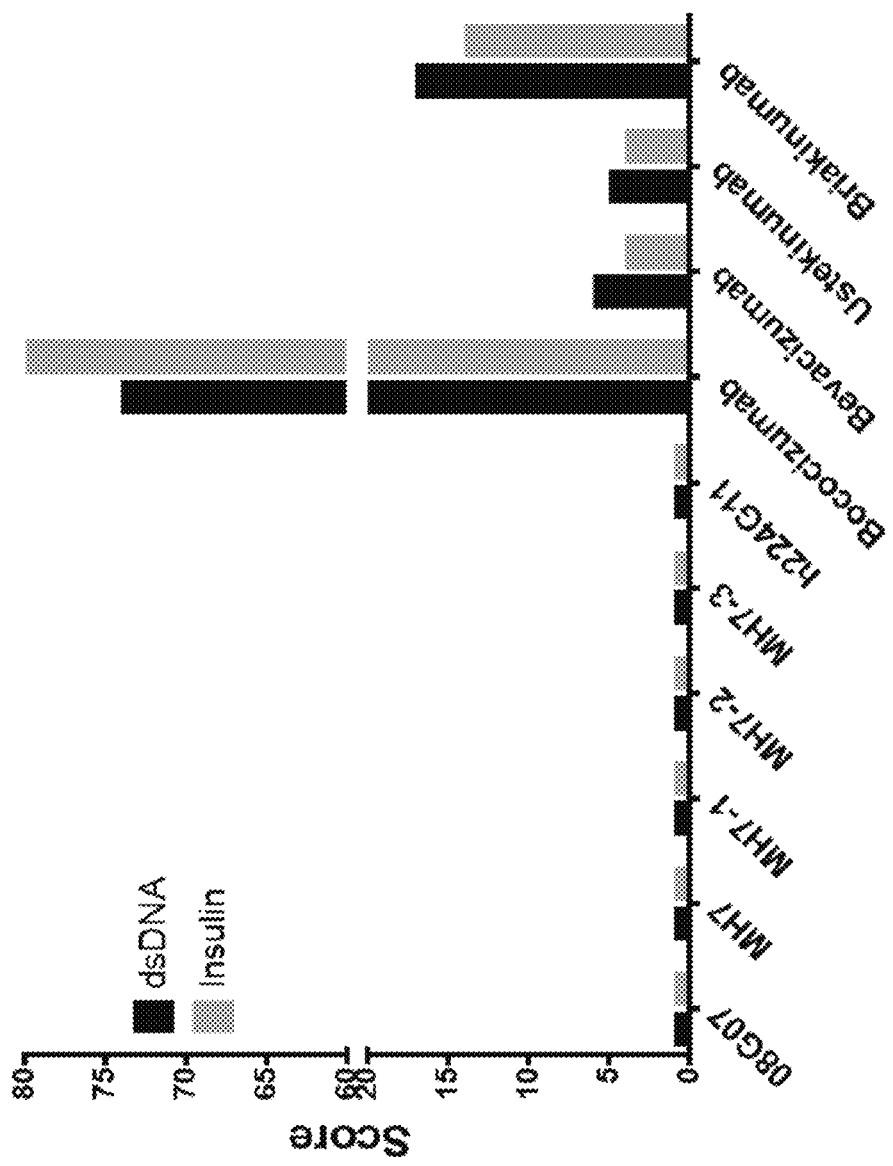
FIG. 9. Development risk ELISAs. Humanized h224G11 and clones 08G07, MH7, MH7-1, MH7-2, MH7-3 in human IgG4(S228P) format were examined for nonspecific binding to the negatively charged biomolecules Insulin and double-stranded DNA (dsDNA). All lead clones demonstrated binding scores of 1.0, significantly lower than either of the negative control IgG1 Ustekinumab and Bevacizumab analogs. Strong off-target binding to insulin or dsDNA, as observed for Bococizumab and Briakinumab analogues, has been shown to be a high-risk indicator of poor pharmacokinetics of therapeutic antibodies.

In flow cytometric analyses, clones 08G07, MH7, MH7-1, MH7-2, MH7-3, h224G11, Grafted, and an isotype control IgG were each tested in IgG4(S228P) format, over a concentration range of 500-0.08 nM for binding to human (FIG. 8A), cyno (FIG. 8B) and untransfected (FIG. 8C) CHO-K1 cells. All IgGs other than the isotype control showed concentration-dependent binding to human and cyno C-MET+ cells, equivalent to, or improved over h224G11, with a maximum MFI in each case being >10-fold higher than observed background signals for Isotype IgG4. No binding was observed for any IgG against untransfected cells.

In polyreactivity ELISAs designed to identify the risk of poor PK in humans (Avery et al. Mabs, 2018), clones 08G07, MH7, MH7-1, MH7-2, MH7-3 and h224G11 all demonstrated baseline signals (all reactivity scores 1.0) against both insulin and dsDNA. These signals were lower than those of the negative control, clinically-approved antibodies Bevacizumab and Ustekinumab (scores 4.0-6.0). Positive control antibodies Briakinumab and Bococizumab, which suffered from short PK in humans, both exhibited strong positive signals >15.0.

In Biacore® analyses of binding affinity to the purified recombinant ectodomain, clones MH7-1, MH7-2, MH7-3 all retained high binding affinity to both human and cyno orthologs of C-MET (Table 9).

Charge Variant Analysis

Figure 10A:
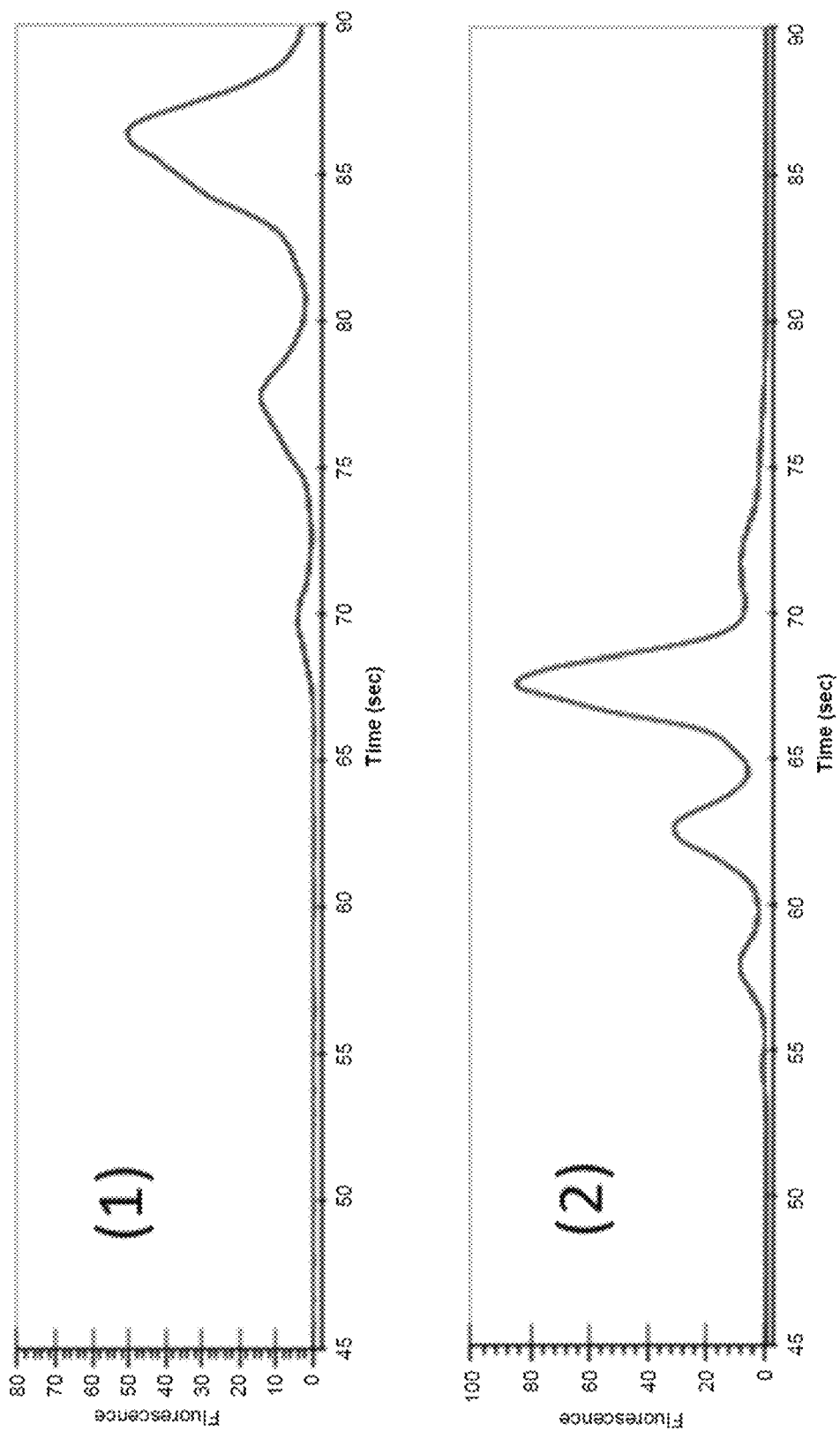
FIG. 10A-FIG. 10C. Charge variant profiles of IgGs. Protein Charge Variant Assay data for the following antibodies in IgG4(S228P) form are shown.
Figure 10B:
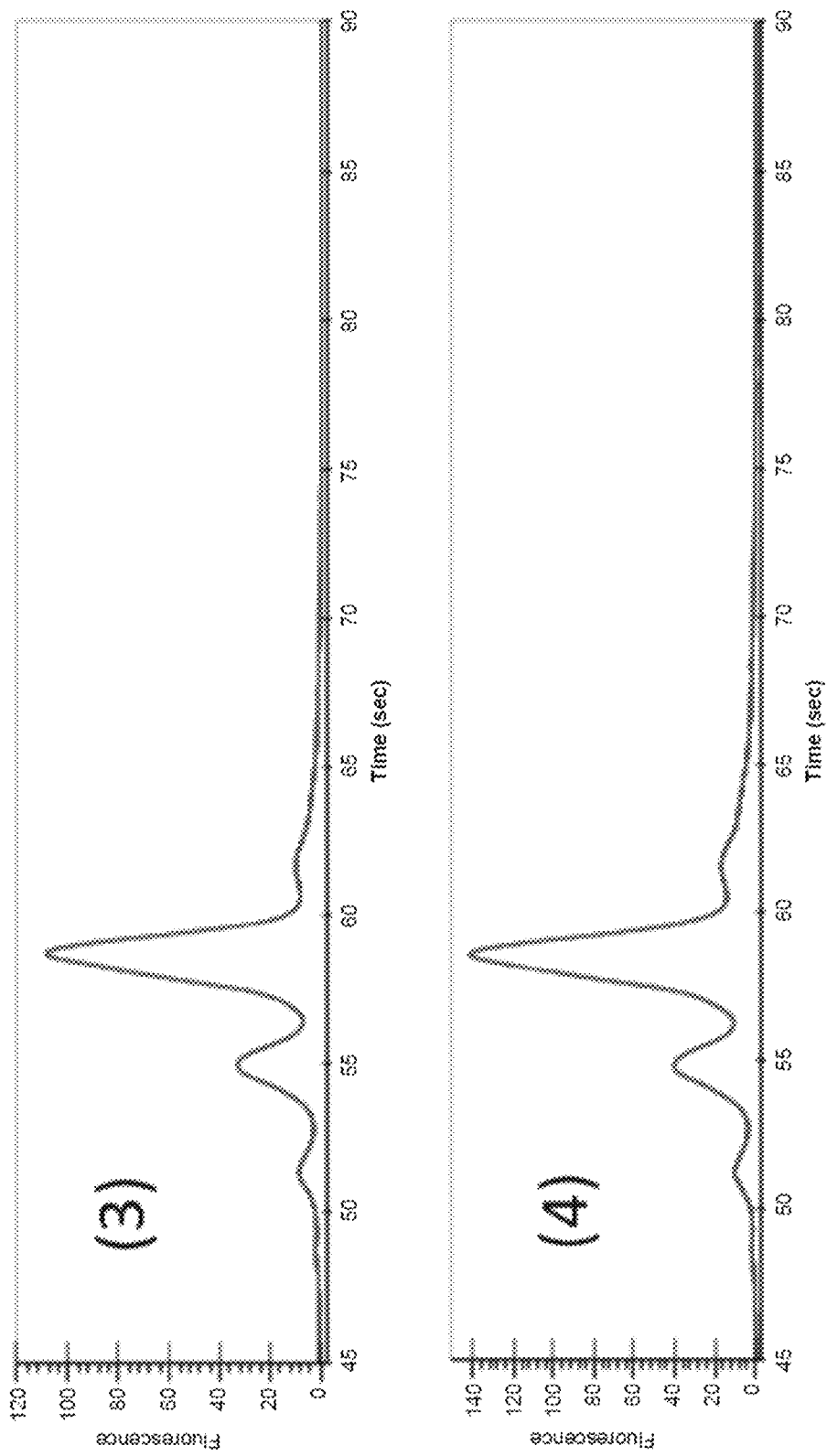
Figure 10C:
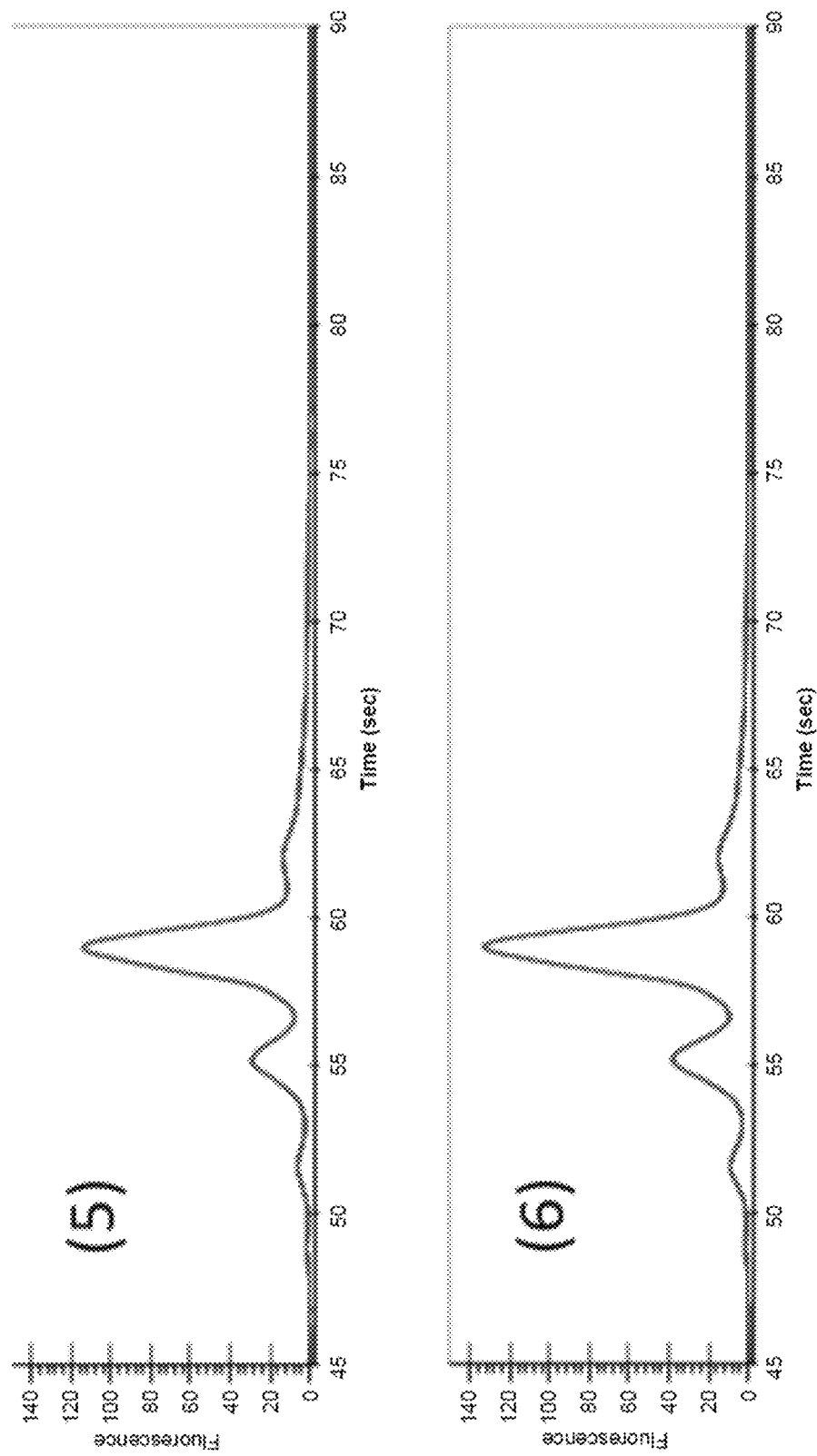

Charge heterogeneity analysis is important in the characterisation of monoclonal antibodies because it provides information about product quality, uniformity and stability. Heterogeneity in recombinant proteins can be caused by enzymatic post-translational modifications (such as glycosylation, lysine truncation) or chemical modifications during purification and storage (such as oxidation or deamidation). Protein Charge Variant Assays such as LabChip® GXII Touch HT allow identification of basic and acidic protein variants relative to the main peak. This microfluidics chip technology electrophoretically separates protein charge variants after fluorescent labelling. The charge variant profiles of six antibodies in IgG4(S228P) form (08G07, MH7, MH7-1, MH7-2, MH7-3 and h224G11), analysed using this method, are depicted in FIG. 10. Unusually for a human IgG, the IgG4 form of h224G11 did not achieve full resolution in the available assay, due to it having a low apparent pI (manufacturer's recommended pI range of main isoform being 7.0 to 9.5), hence only 3 isoforms were identified when this protein was analysed as other, more acidic isoforms (pI<7.0) were likely impossible to resolve (FIG. 10). In contrast, clones 08G07, MH7, MH7-1, MH7-2, MH7-3 in IgG4 form displayed a more homogeneous, well resolved, less complex profile, with the main isoform counting for more than 60% of the total protein. The profiles shown in FIG. 10 suggest that the pI of the main isoform of h224G11 IgG4 is close to 7.0, while those of the clones 08G07, MH7, MH7-1, MH7-2 and MH7-3 IgG4s are all significantly higher, due to the reduction in number of negatively-charged residues in their primary CDR sequence in comparison to h224G11. In addition, the lowered content of deamidation risk motifs in the CDRs of clones 08G07, MH7, MH7-1, MH7-2 and MH7-3, in comparison with h224G11, may further reduce the presence of −ve charge (acidic) variants. This unexpected marked increase in the pI of the lead clones in IgG4 form, over h224G11, is potentially highly beneficial in clinical formulation. The pH of buffers used for antibody liquid formulations is preferred to be at acidic pH, such as pH6, to minimise the progression of e.g. deamidation events during storage. To minimise the risk of antibody aggregation in solution, it is therefore beneficial for the final antibody to have a main functional pI in the basic range, above pH7.4 and preferably above pH8.0.

Figure 11:
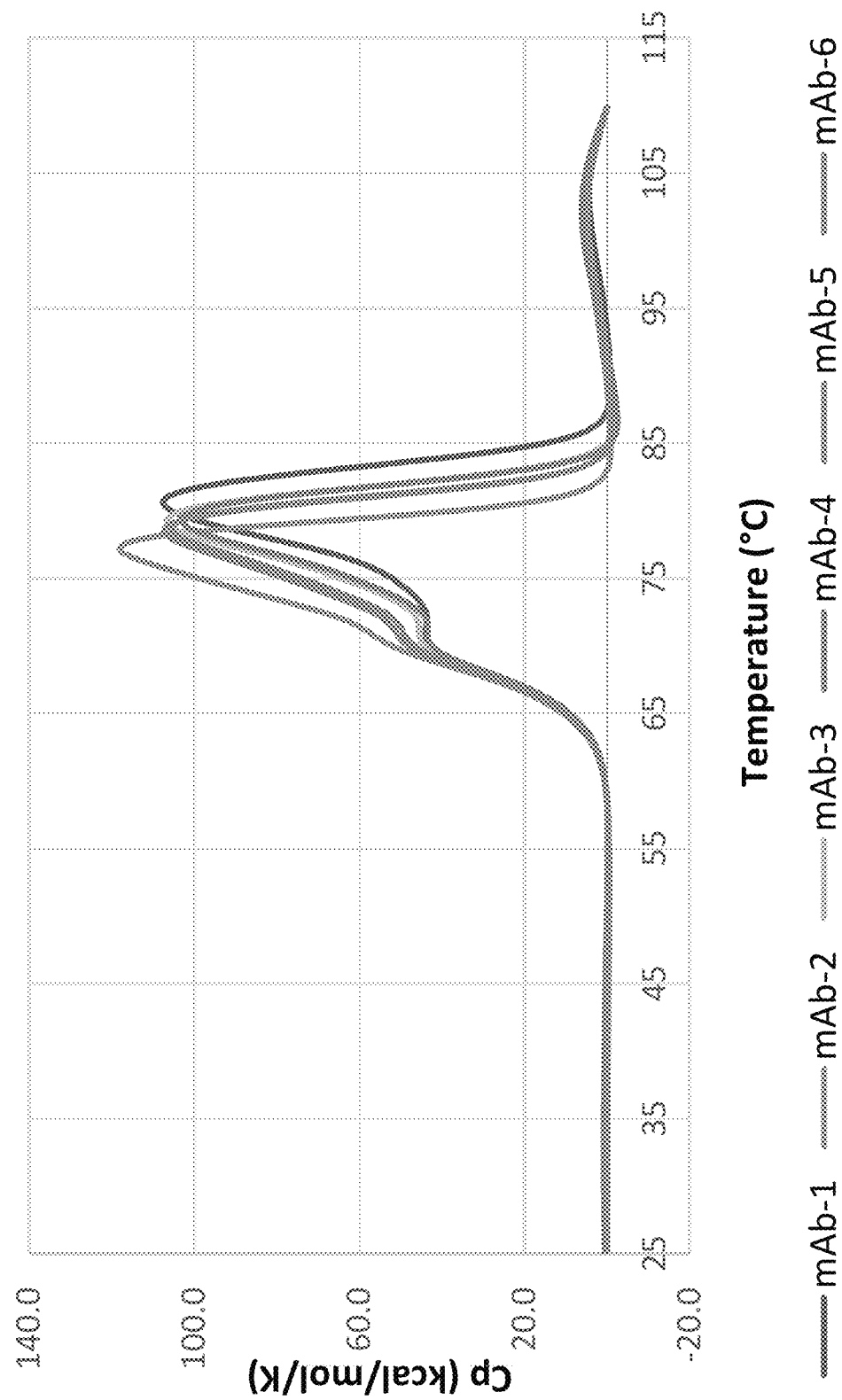
FIG. 11. Differential Scanning Calorimetry (DSC) of IgGs. DSC assay data for the following antibodies in IgG4 (S228P) form are shown: (mAb-1) h224G11, (mAb-2) 08G07, (mAb-3) MH7, (mAb-4) MH7-1, (mAb-5) MH7-2 and (mAb-6) MH7-3.

In addition, the antibodies 08G07, MH7, MH7-1, MH7-2, MH7-3 and h224G11 in IgG4(S228P) form were all analysed in a DSC assay to establish their thermal stability, a surrogate measurement for overall physical stability of the molecule (FIG. 11). All 6 IgGs were found to have highly similar, thermally stable Fab structures, with Tm values spanning a narrow range (77.2-80.6° C.).

Figure 12:
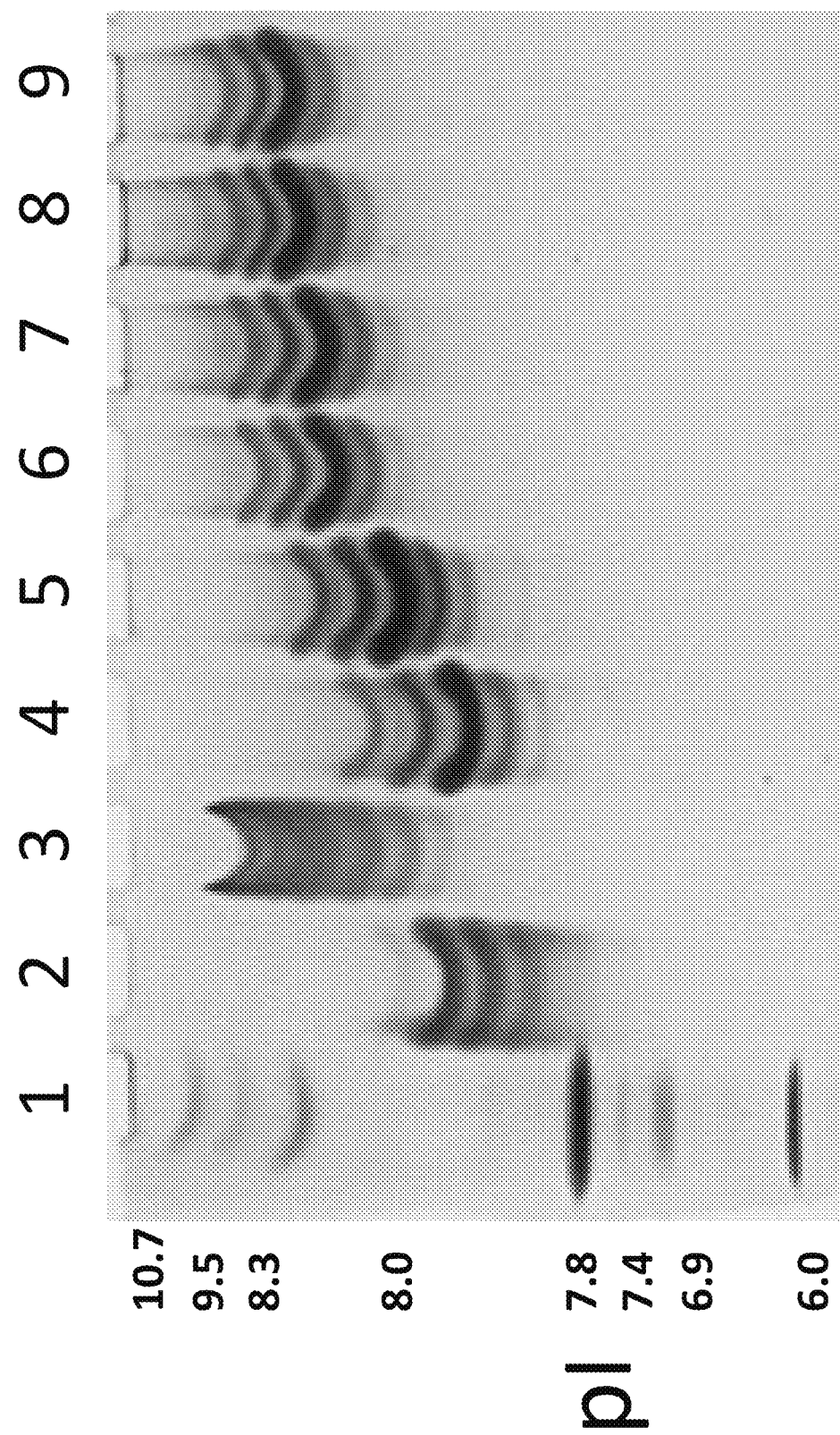
FIG. 12. Isoelectric Focusing analysis. IEF Assay data for the following protein samples are shown: (1) IEF Marker SERVALYT™ 3-10, (2) Brentuximab IgG1, (3) Infiximab IgG1, (4) h224G11 IgG4(S228P), (5) 08G07 IgG4(S228P), (6) MH7 IgG4(S228P), (7) MH7-1 IgG4(S228P), (8) MH7-2 IgG4(S228P) and (9) MH7-3 IgG4(S228P).

As the full spread of charge isoforms of h224G11 could not be resolved via the charge variant assay, the pI characteristics of h224G11 and lead clones 08G07, MH7, MH7-1, MH7-2 and MH7-3 were examined experimentally via Isoelectric Focusing (IEF). Control IgG1 proteins Brentuximab and Infliximab were also included and demonstrated the expected profiles (FIG. 12). In this analysis, the findings of the charge variant assay were confirmed, with clone h224G11 exhibiting a significantly lower pI range than observed for 08G07, MH7, MH7-1, MH7-2 and MH7-3 (FIG. 12). For clone h224G11, it's IgG4(S228P) protein exhibited visible charge isoforms (bands on IEF) across the pI range 7.4 to ~8.2. Charge isoforms in the range of 7.4 are not only a formulation risk, but are also at risk of poor solubility in blood, as their pI is the same as mammalian blood pH, leading to possible in vivo aggregation in man. Lead clone 08G07, in contrast, exhibited visible isoforms from >7.8 to ~8.3 (FIG. 12). Importantly, clones MH7, MH7-1, MH7-2 and MH7-3 all improved yet further over 08G07. Indeed, the progressive improvement in pI of clones was evident up to clone MH7.3, which exhibited a range of visible isoforms from pI 8.0 to >8.3 with a main isoform at 8.3 (FIG. 12). As the v-domain framework regions of all lead clones are identical, this finding illustrated again that the application of non-human mutagenesis and removal of negatively charged residues and asparagines in the CDRs specifically drove not only reduced risk of post-translational modifications in CDR loops, but significantly improved the overall true pI values of lead clones, improving the formulation quality and potential in vivo performance of all clones 08G07, MH7, MH7-1, MH7-2 and MH7-3.

The combined analyses outlined herein demonstrated that, surprisingly, deep sampling of both germline and non-germline amino acids in the CDRs of these antibodies allowed the simultaneous optimisation of both immunogenicity risk and chemical stability risks in the final molecules, without significantly compromising the potency or biophysical stability of the final molecules.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

TABLE 1

Amino acid sequences of 224G11 anti-C-MET CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| Unified | GYIFTAYTMH (SEQ ID NO: 100) | MGWIKPNNGLANYAQKFQG (SEQ ID NO: 106) | SEITTEFDY (SEQ ID NO: 113) | KSSESVDSYANSFLH (SEQ ID NO: 117) | RASTRES (SEQ ID NO: 121) | QQSKEDPLT (SEQ ID NO: 123) |
| Kabat | AYTMH (SEQ ID NO: 101) | WIKPNNGLANYAQKFQG (SEQ ID NO: 107) | SEITTEFDY (SEQ ID NO: 113) | KSSESVDSYANSFLH (SEQ ID NO: 117) | RASTRES (SEQ ID NO: 121) | QQSKEDPLT (SEQ ID NO: 123) |
| Chotia | GYIFTAY (SEQ ID NO: 102) | KPNNGL (SEQ ID NO: 108) | SEITTEFDY (SEQ ID NO: 113) | KSSESVDSYANSFLH (SEQ ID NO: 117) | RASTRES (SEQ ID NO: 121) | QQSKEDPLT (SEQ ID NO: 123) |
| IMGT | GYIFTAYT (SEQ ID NO: 103) | IKPNNGLA (SEQ ID NO: 109) | ARSEITTEFDY (SEQ ID NO: 114) | ESVDSYANSF (SEQ ID NO: 118) | RAS (SEQ ID NO:) | QQSKEDPLT (SEQ ID NO: 123) |
| AHo | ASGYIFTAYTMH (SEQ ID NO: 104) | IKPNNGLANYAQKFQG (SEQ ID NO: 110) | SEITTEFD (SEQ ID NO: 115) | SSESVDSYANSF (SEQ ID NO: 119) | RASTRES (SEQ ID NO: 121) | SKEDPL (SEQ ID NO: 124) |
| AbM | GYIFTAYTMH (SEQ ID NO: 100) | WIKPNNGLAN (SEQ ID NO: 111) | SEITTEFDY (SEQ ID NO: 113) | KSSESVDSYANSFLH (SEQ ID NO: 117) | RASTRES (SEQ ID NO: 121) | QQSKEDPLT (SEQ ID NO: 123) |
| Contact | TAYTMH (SEQ ID NO: 105) | MGWIKPNNGLAN (SEQ ID NO: 112) | ARSEITTEFD (SEQ ID NO: 116) | VDSYANSFLHWY (SEQ ID NO: 120) | LLIYRASTRE (SEQ ID NO: 122) | QQSKEDPL (SEQ ID NO: 125) |

TABLE 2

Amino acid sequence of h224G11 anti-C-MET v-domains and human germline CDR grafts.

| V DOMAIN | Human germline[1] | Amino acid sequence[2] |
|---|---|---|
| h224G11-VH | IGHV1-2 | QVQLVQSGAEVKKPGASVKVSCKASGYIFTAYTMHWVRQAPGQGLEWMGWIKPNNGLANYAQKFQGRVTMTRDTSISTAYMELSRLRSDDTAVYYCARSEITTEFDYWGQGTLVTVSS (SEQ ID NO: 126) |
| VH graft | IGHV1-46[3] | QVQLVQSGAEVKKPGASVKVSCKASGYIFTAYTMHWVRQAPGQGLEWMGWIKPNNGLANYAQKFQGRVTMTRDTSTSTVYMELSSLRSEDTAVYYCARSEITTEFDYWGQGTLVTVSS (SEQ ID NO: 127) |
| h224G11-VL | IGKV4-1 | DIVMTQSPDSLAVSLGERATINCKSSESVDSYANSFLHWYQQKPGQPPKLLIYRASTRESGVPDRFSGSGSGTDFTLTISSLQAEDVAVYYCQQSKEDPLTFGGGTKVEIK (SEQ ID NO: 128) |
| VL graft | IGKV3-20[3] | EIVLTQSPGTLSLSPGERATLSCRASQSVDSYANSFLHWYQQKPGQAPRLLIYRASTRESGIPDRFSGSGSGTDFTLTISRLEPEDFAVYYCQQSKEDPLTFGGGTKVEIK (SEQ ID NO: 129) |

[1] Human germline definitions used for grafting, based on IMGT system.
[2] CDR residues are in bold and underlined. As noted above, the "Unified" CDR definitions used in this manuscript are an expanded definition in comparison to the classical Kabat definition. Each sequence above shows the framework regions (FRs) and the CDRs in the following order: FR1-CDR1-FR2-CDR2-FR3-CDR3-FR4.
[3] Grafts are fully germline in the framework regions, used as the template for CDR mutant library construction.

TABLE 3

Amino acid sequences of unique CDRs from 131 unique anti-C-MET v-domains.

| LCDR1 | LCDR2 | LCDR3 | HCDR1 | HCDR2 | HCDR2 | HCDR3 |
|---|---|---|---|---|---|---|
| RASQSVDSYANSFLA (SEQ ID NO: 130) | AASTRES (SEQ ID NO: 143) | QQSGEDPLTF (SEQ ID NO: 150) | GYIFTAYSMH (SEQ ID NO: 83) | MGIIKPNGGLASYAQKFQG (SEQ ID NO: 174) | MGIIKPSGGSTNYAQKFQG (SEQ ID NO: 193) | AEITTEFDY (SEQ ID NO: 85) |
| RASQSVDSYANSFLH (SEQ ID NO: 131) | AGSTRES (SEQ ID NO: 144) | QQSGEPLTF (SEQ ID NO: 151) | GYIFTAYYMH (SEQ ID NO: 168) | MGIIKPNGGSTSYAQKFQG (SEQ ID NO: 175) | MGIIKPNNGASYAQKFQG (SEQ ID NO: 215) | EEITTEFDY (SEQ ID NO: 80) |
| RASQSVDSYANSYLA (SEQ ID NO: 132) | AGSTRET (SEQ ID NO: 145) | QQSGESPLTF (SEQ ID NO: 152) | GYIFTSYSMH (SEQ ID NO: 43) | MGIIKPNNGSTSYAQKFQG (SEQ ID NO: 176) | MGIIKPSGGLANYAQKFQG (SEQ ID NO: 217) | HEITTEFDY (SEQ ID NO: 238) |
| RASQSVDSYANSYLH (SEQ ID NO: 51) | RASSRES (SEQ ID NO: 146) | QQSGSDPLTF (SEQ ID NO: 153) | GYIFTSYTMH (SEQ ID NO: 48) | MGIIKPSGGSTNYAQKFQG (SEQ ID NO: 84) | MGIIKPSGSASYAQKFQG (SEQ ID NO: 218) | MEITTEFDY (SEQ ID NO: 239) |
| RASQSVDSYAQSFLH (SEQ ID NO: 133) | RASSRET (SEQ ID NO: 147) | QQSGSEPLTF (SEQ ID NO: 154) | GYIFTSYYMH (SEQ ID NO: 169) | MGIIKPSNGTSYAQKFQG (SEQ ID NO: 177) | MGIINPNGGLASYAQKFQG (SEQ ID NO: 219) | QEITTEFDI (SEQ ID NO: 45) |
| RASQSVDSYAQSYLA (SEQ ID NO: 134) | RASTRET (SEQ ID NO: 77) | QQSGSRPLTF (SEQ ID NO: 155) | GYTFTAYSMH (SEQ ID NO: 170) | MGIINPNGGSASYAQKFQG (SEQ ID NO: 178) | MGIINPNGGSASYAQKFQG (SEQ ID NO: 220) | QEITTEFDY (SEQ ID NO: 36) |
| RASQSVDSYAQSYLH (SEQ ID NO: 135) | RGSSRES (SEQ ID NO: 148) | QQSGSSPLTF (SEQ ID NO: 156) | GYTFTAYTMH (SEQ ID NO: 171) | MGIINPSGGLANYAQKFQG (SEQ ID NO: 179) | MGIINPNNGLANYAQKFQG (SEQ ID NO: 221) | QEITTELDY (SEQ ID NO: 240) |
| RASQSVESYANSFLA (SEQ ID NO: 136) | RGSSRET (SEQ ID NO: 149) | QQSKEEPLTF (SEQ ID NO: 157) | GYTFTAYYMH (SEQ ID NO: 172) | MGIINPSGGSTNYAQKFQG (SEQ ID NO: 180) | MGIINPSGGLASYAQKFQG (SEQ ID NO: 222) | SEITTDFDY (SEQ ID NO: 55) |
| RASQSVESYANSYLA (SEQ ID NO: 137) | RGSTRES (SEQ ID NO: 38) | QQSKESPLTF (SEQ ID NO: 158) | GYTFTSYSMH (SEQ ID NO: 78) | MGIINPSNGLANYAQKFQG (SEQ ID NO: 201) | MGIINPSNGTNYAQKFQG (SEQ ID NO: 223) | SEITTEEDY (SEQ ID NO: 241) |
| RASQSVESYANSYLH (SEQ ID NO: 52) | RGSTRET (SEQ ID NO: 56) | QQSKSDPLTF (SEQ ID NO: 159) | GYTFTSYTMH (SEQ ID NO: 34) | MGIINPSNGLASYAQKFQG (SEQ ID NO: 202) | MGIINPSNGTSYAQKFQG (SEQ ID NO: 224) | SEITTEFDA (SEQ ID NO: 242) |
| RASQSVESYAQSFLH (SEQ ID NO: 138) | | QQSKSEPLTF (SEQ ID NO: 160) | GYTFTSYYMH (SEQ ID NO: 173) | MGIINPSNGLTSYAQKFQG (SEQ ID NO: 203) | MGWIKPNGGLTSYAQKFQG (SEQ ID NO: 225) | SEITTEFDE (SEQ ID NO: 243) |
| RASQSVESYAQSYLH (SEQ ID NO: 46) | | QQSKSSPLTF (SEQ ID NO: 161) | | MGIINPSNGSASYAQKFQG (SEQ ID NO: 204) | MGWIKPNNGLTSYAQKFQG (SEQ ID NO: 226) | SEITTEFDF (SEQ ID NO: 244) |

TABLE 3-continued

Amino acid sequences of unique CDRs from 131 unique anti-C-MET v-domains.

| LCDR1 | LCDR2 | LCDR3 | HCDR1 | HCDR2 | HCDR2 | HCDR3 |
|---|---|---|---|---|---|---|
| RASQSVSSYANSFLH (SEQ ID NO: 139) | | QQYGSDPLTF (SEQ ID NO: 162) | | MGWIKPSNGLASYAQKFQG (SEQ ID NO: 183) | MGWIKPNNGLANYAQKFQG (SEQ ID NO: 205) | SEITTEFDI (SEQ ID NO: 245) |
| RASQSVSSYANSYLA (SEQ ID NO: 140) | | QQYGSEPLTF (SEQ ID NO: 163) | | MGWIKPSNGSANYAQKFQG (SEQ ID NO: 184) | MGWIKPNNGGSASYAQKFQG (SEQ ID NO: 206) | SEITTEFDK (SEQ ID NO: 246) |
| RASQSVSSYANSYLH (SEQ ID NO: 37) | | QQYKEEPLTF (SEQ ID NO: 164) | | MGWIKPSNGSASYAQKFQG (SEQ ID NO: 185) | MGWIKPNNGSTSYAQKFQG (SEQ ID NO: 207) | SEITTEFDL (SEQ ID NO: 247) |
| RASQSVSSYAQSFLA (SEQ ID NO: 141) | | QQYKESPLTF (SEQ ID NO: 165) | | MGWIKPSNGSTSYAQKFQG (SEQ ID NO: 186) | MGWIKPSNGLTSYAQKFQG (SEQ ID NO: 208) | SEITTEFDM (SEQ ID NO: 248) |
| RASQSVSSYAQSFLH (SEQ ID NO: 142) | | QQYKSDPLTF (SEQ ID NO: 166) | | MGWINPNGGLTNYAQKFRG (SEQ ID NO: 79) | MGWIKPSNGSTNYAQKFQG (SEQ ID NO: 49) | SEITTEFDQ (SEQ ID NO: 249) |
| RASQSVSSYAQSYLH (SEQ ID NO: 57) | | QQYKSSPLTF (SEQ ID NO: 167) | | MGWINPNGGLTSYAQKFQG (SEQ ID NO: 187) | MGWINPNGGSASYAQKFQG (SEQ ID NO: 231) | SEITTEFDS (SEQ ID NO: 250) |
| | | | | MGWINPNNGLANYAQKFQG (SEQ ID NO: 188) | MGWINPNNGLTNYAQKFQG (SEQ ID NO: 232) | SEITTEFDV (SEQ ID NO: 251) |
| | | | | MGWINPNNGLASYAQKFQG (SEQ ID NO: 189) | MGWINPNNGSANYAQKFQG (SEQ ID NO: 233) | SEITTEFDW (SEQ ID NO: 252) |
| | | | | MGWINPSGGLASYAQKFQG (SEQ ID NO: 190) | MGWINPSGGLANYAQKFQG (SEQ ID NO: 234) | SEITTELDY (SEQ ID NO: 253) |
| | | | | MGWINPSGGSASYAQKFQG (SEQ ID NO: 191) | MGWINPSGGLTNYAQKFQG (SEQ ID NO: 54) | SEITTEQDY (SEQ ID NO: 50) |
| | | | | MGWINPSGGSTSYAQKFQG (SEQ ID NO: 40) | MGWINPSGGLTSYAQKFQG (SEQ ID NO: 235) | SEITTEWDY (SEQ ID NO: 254) |
| | | | | MGWINPSNGLANYAQKFQG | MGWINPSNGSASYAQKFQG | TEITTEFDY |

TABLE 3-continued

Amino acid sequences of unique CDRs from 131 unique anti-C-MET v-domains.

| LCDR1 | LCDR2 | LCDR3 | HCDR1 | HCDR2 | HCDR3 |
|---|---|---|---|---|---|
| | | | | (SEQ ID NO: 44) | (SEQ ID NO: 88) |
| | | | MGWINPSNGLTNYAQKFQG (SEQ ID NO: 192) | MGWINPSGGSTNYAQKFQG (SEQ ID NO: 213) | |
| | | | | MGWINPSNGSTSYAQKFQG (SEQ ID NO: 214) | |
| | | | | MGWINPSNGSTSYAQKFQG (SEQ ID NO: 236) | |
| | | | | (SEQ ID NO: 237) | VEITTEFDL (SEQ ID NO: 255) |

TABLE 4

Amino acid sequences of CDRs of unique, library-derived and designer, human/cyno cross-reactive anti-C-MET IgGs.

| CLONE | LCDR1 | LCDR2 | LCDR3 | HCDR1 | HCDR2 | HCDR3 |
|---|---|---|---|---|---|---|
| 04F09 | RASQSVESYAQSYLH (SEQ ID NO: 46) | RGSTRES (SEQ ID NO: 38) | QQSKSDPLT (SEQ ID NO: 76) | GYIFTSYSMH (SEQ ID NO: 43) | MGWINPSNGLANYAQKFQG (SEQ ID NO: 44) | QEITTEFDI (SEQ ID NO: 45) |
| 07A01 | RASQSVDSYANSYLH (SEQ ID NO: 51) | RGSTRES (SEQ ID NO: 38) | QQSKESPLT (SEQ ID NO: 47) | GYIFTSYTMH (SEQ ID NO: 48) | MGWINPNGGLASYAQKFQG (SEQ ID NO: 49) | SEITTEQDY (SEQ ID NO: 50) |
| 09A12 | RASQSVSSYAQSYLH (SEQ ID NO: 57) | RASTRET (SEQ ID NO: 77) | QQSKESPLT (SEQ ID NO: 47) | GYTFTSYSMH (SEQ ID NO: 78) | MGWINPNGGLTNYAQKFRG (SEQ ID NO: 79) | EEITTEFDY (SEQ ID NO: 80) |
| 09B08 | RASQSVDSYANSYLH (SEQ ID NO: 51) | RGSTRES (SEQ ID NO: 38) | QQSKSDPLT (SEQ ID NO: 76) | GYTFTSYTMH (SEQ ID NO: 34) | MGWINPNNGSTNYAQKFQG (SEQ ID NO: 81) | SEITTDFDY (SEQ ID NO: 55) |
| 07C10 | RASQSVESYAQSYLH (SEQ ID NO: 46) | RGSTRES (SEQ ID NO: 38) | QQSKEEPLT (SEQ ID NO: 82) | GYIPTAYSMH (SEQ ID NO: 83) | MGIIKPSNGSTNYAQKFQG (SEQ ID NO: 84) | AEITTEFDY (SEQ ID NO: 85) |
| 09E04 | RASQSVDSYANSYLH (SEQ ID NO: 52) | RGSTRES (SEQ ID NO: 38) | QQYGSEPLT (SEQ ID NO: 53) | GYIFTSYTMH (SEQ ID NO: 48) | MGWINPNGGSTSYAQKFQG (SEQ ID NO: 42) | QEITTEFDY (SEQ ID NO: 36) |
| 08G07 | RASQSVDSYANSYLH (SEQ ID NO: 51) | RGSTRES (SEQ ID NO: 38) | QQSKSEPLT (SEQ ID NO: 39) | GYTFTSYTMH (SEQ ID NO: 34) | MGWINPSGGLANYAQKFQG (SEQ ID NO: 54) | SEITTDFDY (SEQ ID NO: 55) |
| 04E10 | RASQSVDSYANSYLH (SEQ ID NO: 51) | RGSTRES (SEQ ID NO: 38) | QQSKSEPLT (SEQ ID NO: 39) | GYIFTSYTMH (SEQ ID NO: 48) | MGWIKPNNGSASYAQKFQG (SEQ ID NO: 86) | SEITTEEDY (SEQ ID NO: 241) |
| 08B12 | RASQSVDSYANSYLH (SEQ ID NO: 51) | RGSTRET (SEQ ID NO: 56) | QQSKSDPLT (SEQ ID NO: 76) | GYIPTAYSMH (SEQ ID NO: 83) | MGWIKPNNGSTNYAQKFQG (SEQ ID NO: 87) | TEITTEFDY (SEQ ID NO: 88) |
| MH1 | RASQSVSSYANSYLH (SEQ ID NO: 37) | RGSTRES (SEQ ID NO: 38) | QQSKSEPLT (SEQ ID NO: 39) | GYTFTSYTMH (SEQ ID NO: 34) | MGWINPNGGSTNYAQKFQG (SEQ ID NO: 42) | QEITTEFDY (SEQ ID NO: 36) |
| MH2 | RASQSVSSYAQSYLH (SEQ ID NO: 57) | RGSTRET (SEQ ID NO: 56) | QQYGSSPLT (SEQ ID NO: 89) | GYTFTSYTMH (SEQ ID NO: 34) | MGWINPNGGSTSYAQKFQG (SEQ ID NO: 42) | QEITTEFDY (SEQ ID NO: 36) |
| MH3 | RASQSVSSYAQSYLH (SEQ ID NO: 57) | RGSTRET (SEQ ID NO: 56) | QQYGSPLT (SEQ ID NO: 90) | GYTFTSYTMH (SEQ ID NO: 34) | MGWINPNGGSTSYAQKFQG (SEQ ID NO: 42) | QEITTEFDY (SEQ ID NO: 36) |

TABLE 4-continued

Amino acid sequences of CDRs of unique, library-derived and designer, human/cyno cross-reactive anti-C-MET IgGs.

| CLONE | LCDR1 | LCDR2 | LCDR3 | HCDR1 | HCDR2 | HCDR3 |
|---|---|---|---|---|---|---|
| MH4 | RASQSVSSYANSYLH (SEQ ID NO: 37) | RGSTRES (SEQ ID NO: 38) | QQSKSEPLT (SEQ ID NO: 39) | GYTFTSYTMH (SEQ ID NO: 34) | MGWINPSGGSTSYAQKFQG (SEQ ID NO: 40) | QEITTEFDY (SEQ ID NO: 36) |
| MH5 | RASQSVSSYAQSYLH (SEQ ID NO: 57) | RGSTRET (SEQ ID NO: 56) | QQSGSSPLT (SEQ ID NO: 89) | GYTFTSYTMH (SEQ ID NO: 34) | MGWINPSGGSTSYAQKFQG (SEQ ID NO: 40) | QEITTEFDY (SEQ ID NO: 36) |
| MH6 | RASQSVSSYAQSYLH (SEQ ID NO: 57) | RGSTRET (SEQ ID NO: 56) | QQYGSSPLT (SEQ ID NO: 90) | GYTFTSYTMH (SEQ ID NO: 34) | MGWINPSGGSTSYAQKFQG (SEQ ID NO: 40) | QEITTEFDY (SEQ ID NO: 36) |
| MH7 | RASQSVSSYANSYLH (SEQ ID NO: 37) | RGSTRES (SEQ ID NO: 38) | QQSKSEPLT (SEQ ID NO: 39) | GYTFTSYTMH (SEQ ID NO: 34) | MGIINPSGGSTSYAQKFQG (SEQ ID NO: 35) | QEITTEFDY (SEQ ID NO: 36) |
| MH8 | RASQSVSSYAQSYLH (SEQ ID NO: 57) | RGSTRET (SEQ ID NO: 56) | QQSGSSPLT (SEQ ID NO: 89) | GYTFTSYTMH (SEQ ID NO: 34) | MGIINPSGGSTSYAQKFQG (SEQ ID NO: 35) | QEITTEFDY (SEQ ID NO: 36) |
| MH9 | RASQSVSSYAQSYLH (SEQ ID NO: 57) | RGSTRET (SEQ ID NO: 56) | QQYGSSPLT (SEQ ID NO: 90) | GYTFTSYTMH (SEQ ID NO: 34) | MGIINPSGGSTSYAQKFQG (SEQ ID NO: 35) | QEITTEFDY (SEQ ID NO: 36) |
| MH10 | RASQSVSSYANSYLH (SEQ ID NO: 37) | RGSTRES (SEQ ID NO: 38) | QQSKSEPLT (SEQ ID NO: 39) | GYTFTSYAMH (SEQ ID NO: 41) | MGWINPSGGSTSYAQKFQG (SEQ ID NO: 40) | QEITTEFDY (SEQ ID NO: 36) |
| MH11 | RASQSVSSYAQSYLH (SEQ ID NO: 57) | RGSTRET (SEQ ID NO: 56) | QQSGSSPLT (SEQ ID NO: 89) | GYTFTSYAMH (SEQ ID NO: 41) | MGWINPSGGSTSYAQKFQG (SEQ ID NO: 40) | QEITTEFDY (SEQ ID NO: 36) |
| MH12 | RASQSVSSYAQSYLH (SEQ ID NO: 57) | RGSTRET (SEQ ID NO: 56) | QQYGSSPLT (SEQ ID NO: 90) | GYTFTSYAMH (SEQ ID NO: 41) | MGWINPSGGSTSYAQKFQG (SEQ ID NO: 40) | QEITTEFDY (SEQ ID NO: 36) |

TABLE 5

Biacore® affinity values for IgG binding to human and cyno monomeric C-MET.

| Clone | Human C-MET | | | | Cyno C-MET | | | |
|---|---|---|---|---|---|---|---|---|
| name | ka (1/Ms) | kd (1/s) | Chi2 | KD (nM) | ka (1/Ms) | kd (1/s) | Chi2 | KD (nM) |
| Graft | 9.90E+04 | 3.70E−05 | 0.836 | 0.37 | 2.30E+05 | 5.20E−05 | 0.089 | 0.22 |
| h224G11 | 9.00E+04 | 4.20E−05 | 0.795 | 0.47 | 2.50E+05 | 1.10E−04 | 0.742 | 0.46 |
| 08G07 | 6.34E+04 | 7.54E−06 | 0.191 | 0.12 | 1.00E+05 | 2.40E−05 | 1.15 | 0.24 |
| 04F09 | 1.40E+05 | 1.80E−05 | 0.966 | 0.13 | 2.90E+05 | 5.60E−05 | 0.203 | 0.19 |
| 09E04 | 8.50E+04 | 1.60E−05 | 0.545 | 0.18 | 1.70E+05 | 6.40E−05 | 1.04 | 0.39 |
| 07A01 | 5.60E+04 | 1.30E−05 | 0.139 | 0.24 | 9.40E+04 | 1.60E−05 | 1.6 | 0.17 |
| MH4 | 8.70E+04 | 2.50E−05 | 1.62 | 0.28 | 2.60E+05 | 4.90E−05 | 0.099 | 0.19 |
| MH7 | 9.80E+04 | 2.90E−05 | 0.882 | 0.3 | 2.70E+05 | 5.20E−05 | 0.121 | 0.19 |
| MH10 | 7.10E+04 | 4.40E−05 | 0.496 | 0.63 | 1.80E+05 | 3.60E−05 | 1.07 | 0.2 |
| MH1 | 9.47E+04 | 7.11E−05 | 0.689 | 0.75 | 1.80E+05 | 2.60E−05 | 1.21 | 0.14 |
| 07C10 | 1.20E+05 | 9.40E−05 | 0.03 | 0.78 | 6.50E+04 | 2.10E−04 | 0.213 | 3.2 |
| 09B08 | 3.70E+04 | 4.10E−05 | 0.064 | 1.1 | 6.00E+04 | 1.20E−05 | 0.135 | 0.2 |
| 04E10 | 3.10E+04 | 5.00E−05 | 0.055 | 1.6 | 4.90E+04 | 1.10E−04 | 0.099 | 2.2 |
| MH5 | 7.70E+04 | 1.50E−04 | 0.883 | 2 | 1.70E+05 | 2.10E−04 | 1.63 | 1.3 |
| 09A12 | 7.40E+04 | 1.50E−04 | 0.671 | 2 | 1.60E+05 | 2.30E−04 | 0.919 | 1.5 |
| MH8 | 6.60E+04 | 1.50E−04 | 0.638 | 2.2 | 1.60E+05 | 2.10E−04 | 0.736 | 1.3 |
| MH2 | 7.30E+04 | 1.80E−04 | 1.2 | 2.5 | 2.40E+05 | 2.10E−04 | 0.068 | 0.87 |
| MH11 | 6.20E+04 | 1.60E−04 | 0.323 | 2.6 | 1.50E+05 | 1.80E−04 | 0.589 | 1.2 |
| MH12 | 5.60E+04 | 3.70E−04 | 0.134 | 6.5 | 1.10E+05 | 4.30E−04 | 1.29 | 4 |
| MH9 | 5.90E+04 | 3.90E−04 | 0.164 | 6.6 | 1.10E+05 | 4.80E−04 | 1.89 | 4.3 |
| MH03 | 6.80E+04 | 5.10E−04 | 0.505 | 7.6 | 1.50E+05 | 6.20E−04 | 1.06 | 4.1 |
| MH6 | 6.50E+04 | 5.30E−04 | 0.475 | 8.2 | 1.60E+05 | 6.30E−04 | 0.861 | 4 |
| 08B12 | 3.70E+04 | 3.10E−04 | 0.051 | 8.4 | 5.40E+04 | 4.30E−04 | 0.039 | 8.1 |

TABLE 6

Flow cytometric EC50 values for IgG binding to human and cyno CHO-K1.

| | EC50 (nM) | |
|---|---|---|
| Clone | hucMET | cycMET |
| MH7 | 1.14 | 0.54 |
| MH9 | 1.23 | 0.65 |
| MH8 | 1.24 | 0.57 |
| MH12 | 1.25 | 0.51 |
| MH6 | 1.33 | 0.72 |
| MH2 | 1.59 | 0.34 |
| MH3 | 1.66 | 0.27 |
| MH11 | 1.68 | 0.69 |
| MH4 | 1.72 | 0.48 |
| MH5 | 1.76 | 0.3 |
| MH1 | 2.02 | 0.26 |
| MH10 | 2.14 | 0.46 |
| 09A12 | 2.33 | 0.28 |
| 09E04 | 2.9 | 1.11 |
| 08G07 | 4.19 | 0.68 |
| h224G11 | 6.83 | 0.82 |
| 07A01 | 7.44 | 1.74 |
| 09B08 | 9.3 | 3.78 |
| 07C10 | 9.59 | 2.82 |
| 04E10 | 9.66 | 2.94 |
| 08B12 | 11.67 | 1.34 |
| 04F09 | 12.41 | 0.64 |
| Isotype IgG4 | N.D. | N.D. |

N.D.—Not determined

TABLE 7

Human T cell epitope content in v-domains predicted by iTOPE™ and TCED™.

| Clone Name | Germline epitopes | Low Affinity Foreign | High Affinity Foreign | TCED+ |
|---|---|---|---|---|
| h224G11 VL | 4 | 1 | 2 | 0 |
| h224G11 VH | 7 | 1 | 2 | 0 |
| 08G07 VL | 1 | 2 | 1 | 0 |
| 08G07 VH | 8 | 1 | 1 | 0 |
| 07A01 VL | 1 | 1 | 1 | 0 |
| 07A01 VH | 8 | 2 | 2 | 0 |
| MH1 VL | 1 | 2 | 1 | 0 |
| MH1 VH | 8 | 2 | 1 | 0 |
| MH4 VL | 1 | 2 | 1 | 0 |
| MH4 VH | 8 | 1 | 1 | 0 |
| MH7 VL | 1 | 2 | 1 | 0 |
| MH7 VH | 10 | 0 | 1 | 0 |
| MH7-1 VL | 1 | 2 | 0 | 0 |
| MH7-1 VH | 10 | 0 | 1 | 0 |
| MH7-2 VL | 1 | 1 | 0 | 0 |
| MH7-2 VH | 10 | 0 | 1 | 0 |
| MH7-3 VL | 1 | 1 | 0 | 0 |
| MH7-3 VH | 10 | 0 | 1 | 0 |

TABLE 8

Amino acid sequences of CDRs of unique, deimmunised, designer, human/cyno cross-reactive anti-C-MET IgGs.

| CLONE | LCDR1 | LCDR2 | LCDR3 | HCDR1 | HCDR2 | HCDR3 |
|---|---|---|---|---|---|---|
| MH7-1 | RASQSVSSYANSYLH (SEQ ID NO: 37) | RGSTRET (SEQ ID NO: 56) | QQSKSEPLT (SEQ ID NO: 39) | GYTFTSYTMH (SEQ ID NO: 34) | MGIINPSGGSTSYAQKFQG (SEQ ID NO: 35) | QEITTEFDY (SEQ ID NO: 36) |

TABLE 8-continued

Amino acid sequences of CDRs of unique, deimmunised, designer, human/cyno cross-reactive anti-C-MET IgGs.

| CLONE | LCDR1 | LCDR2 | LCDR3 | HCDR1 | HCDR2 | HCDR3 |
|---|---|---|---|---|---|---|
| MH7-2 | RASQSVSSYANSYLH (SEQ ID NO: 37) | RGSTRET (SEQ ID NO: 56) | QQSKESPLT (SEQ ID NO: 47) | GYTFTSYTMH (SEQ ID NO: 34) | MGIINPSGGSTSYAQKFQG (SEQ ID NO: 35) | QEITTEFDY (SEQ ID NO: 36) |
| MH7-3 | RASQSVSSYAQSYLH (SEQ ID NO: 57) | RGSTRET (SEQ ID NO: 56) | QQSKESPLT (SEQ ID ) NO: 47) | GYTFTSYTMH (SEQ ID NO: 34) | MGIINPSGGSTSYAQKFQG (SEQ ID NO: 35) | QEITTEFDY (SEQ ID NO: 36) |

TABLE 9

BIACORE® affinity values for IgG binding to human and cyno monomeric C-MET.

| Clone name | Human C-MET | | | | Cyno C-MET | | | |
|---|---|---|---|---|---|---|---|---|
| | ka (1/Ms) | kd (1/s) | Chi2 | KD (nM) | ka (1/Ms) | kd (1/s) | Chi2 | KD (nM) |
| MH7.1 | 9.79E+04 | 1.51E−04 | 0.11 | 1.54 | 1.81E+05 | 1.98E−04 | 0.683 | 1.1 |
| MH7.2 | 9.32E+04 | 1.98E−04 | 0.108 | 2.12 | 1.83E+05 | 1.59E−04 | 0.394 | 0.87 |
| MH7.3 | 9.44E+04 | 1.23E−04 | 0.137 | 1.31 | 1.68E+05 | 1.74E−04 | 0.687 | 1.03 |

TABLE 10

Examples of antibody variable region amino acid sequences.

Antibody MH7-3 heavy chain variable (VH) region
QVQLVQSGAEVKKPGASVKVSCKASGYTFTSYTMHWVRQAPGQGLEWMG
IINPSGGSTSYAQKFQGRVTMTRDTSTSTVYMELSSLRSEDTAVYYCAR
QEITTEFDYWGQGTLVTVSS (SEQ ID NO: 1)

Antibody MH7-3 light chain variable (VL) region
EIVLTQSPGTLSLSPGERATLSCRASQSVSSYAQSYLHWYQQKPGQAPR
LLIYRGSTRETGIPDRFSGSGSGTDFTLTISRLEPEDFAVYYCQQSKES
PLTFGGGTKVEIK (SEQ ID NO: 2)

Antibody MH7-2 heavy chain variable (VH) region
QVQLVQSGAEVKKPGASVKVSCKASGYTFTSYTMHWVRQAPGQGLEWMG
IINPSGGSTSYAQKFQGRVTMTRDTSTSTVYMELSSLRSEDTAVYYCAR
QEITTEFDYWGQGTLVTVSS (SEQ ID NO: 3)

Antibody MH7-2 light chain variable (VL) region
EIVLTQSPGTLSLSPGERATLSCRASQSVSSYANSYLHWYQQKPGQAPR
LLIYRGSTRETGIPDRFSGSGSGTDFTLTISRLEPEDFAVYYCQQSKES
PLTFGGGTKVEIK (SEQ ID NO: 4)

Antibody MH7-1 heavy chain variable (VH) region
QVQLVQSGAEVKKPGASVKVSCKASGYTFTSYTMHWVRQAPGQGLEWMG
IINPSGGSTSYAQKFQGRVTMTRDTSTSTVYMELSSLRSEDTAVYYCAR
QEITTEFDYWGQGTLVTVSS (SEQ ID NO: 5)

Antibody MH7-1 light chain variable (VL) region
EIVLTQSPGTLSLSPGERATLSCRASQSVSSYANSYLHWYQQKPGQAPR
LLIYRGSTRETGIPDRFSGSGSGTDFTLTISRLEPEDFAVYYCQQSKSE
PLTFGGGTKVEIK (SEQ ID NO: 6)

Antibody MH7 heavy chain variable (VH) region
QVQLVQSGAEVKKPGASVKVSCKASGYTFTSYTMHWVRQAPGQGLEWMG
IINPSGGSTSYAQKFQGRVTMTRDTSTSTVYMELSSLRSEDTAVYYCAR
QEITTEFDYWGQGTLVTVSS (SEQ ID NO: 7)

Antibody MH7 light chain variable (VL) region
EIVLTQSPGTLSLSPGERATLSCRASQSVSSYANSYLHWYQQKPGQAPR
LLIYRGSTRESGIPDRFSGSGSGTDFTLTISRLEPEDFAVYYCQQSKSE
PLTFGGGTKVEIK (SEQ ID NO: 8)

Antibody 08G07 heavy chain variable (VH) region
QVQLVQSGAEVKKPGASVKVSCKASGYTFTSYTMHWVRQAPGQGLEWMG
WINPSGGLANYAQKFQGRVTMTRDTSTSTVYMELSSLRSEDTAVYYCAR
SEITTDFDYWGQGTLVTVSS (SEQ ID NO: 9)

Antibody 08G07 light chain variable (VL) region
EIVLTQSPGTLSLSPGERATLSCRASQSVDSYANSYLHWYQQKPGQAPR
LLIYRGSTRESGIPDRFSGSGSGTDFTLTISRLEPEDFAVYYCQQSKSE
PLTFGGGTKVEIK (SEQ ID NO: 10)

TABLE 11

Examples of antibody Fc region amino acid sequences.

Human IgG4 wild type
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK (SEQ ID NO: 11)

Human IgG4 (S228P)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK (SEQ ID NO: 12)

Human IgG1 wild type
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK (SEQ ID NO: 13)

TABLE 11-continued

Examples of antibody Fc region amino acid sequences.

Human IgG1-3M
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAAGAPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPS<u>RDELT</u>KNQVSLTC
LVKGFYPSDIAVEWESNGQPENNYKTTPPVLDSDGSF<u>FLYSK</u>LTVDKSRW
QQGNVFSCSVMHEALHNHYTQKSLSLSPGK (SEQ ID NO: 14)

Human IgG2 wild type
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDISVEWESNGQPENNYKTTPPMLDSDGSFFLYSKLTVDKSRWQQGN
VFSCSVMHEALHNHYTQKSLSLSPGK (SEQ ID NO: 15)

TABLE 11-continued

Examples of antibody Fc region amino acid sequences.

Human IgG1 wild type "REEM" allotype
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPS<u>REEMT</u>KNQVSLTC
LVKGFYPSDIAVEWESNGQPENNYKTTPPVLDSDGSF<u>FLYSK</u>LTVDKSRW
QQGNVFSCSVMHEALHNHYTQKSLSLSPGK (SEQ ID NO: 16)

Human IgG1-3M "REEM" allotype
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAAGAPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPS<u>REEMK</u>NQVSLTCL
VKGFYPSDIAVEWESNGQPENNYKTTPPVLDSDGSFFLYSKLTVDKSRWQ
QGNVFSCSVMHEALHNHYTQKSLSLSPGK (SEQ ID NO: 17)

TABLE 12

Examples of C-MET protein amino acid sequences.

Human C-MET sequence
MKAPAVLAPGILVLLFTLVQRSNGECKEALAKSEMNVMKYQLPNFTAETPIQNVILHEH
HIFLGATNYIYVLNEEDLQKVAEYKTGPVLEHPDCFPCQDCSSKANLEGGVWKDNINMAL
VVDTYYDDQLISCGSVNRGTCQRHVFPHNHTADIQSEVHCIFSPQIEEPSQCPDCVVSAL
GAKVLSSVKDRFINFFVGNTINSSYFPDHPLHSISVRRLKETKDGFMFLTDQSYIDVLPE
FRDSYPIKYVHAFESNNFIYFLTVQRETLDAQTFHTRIIRFCSINSGLHSYMEMPLECIL
TEKRKKRSTKKEVFNILQAAYVSKPGAQLARQIGASLNDDILFGVFAQSKPDSAEPMDRS
AMCAFPIKYVNDFFNKIVNKNNVRCLQHFYGPNHEHCFNRTLLRNSSGCEARRDEYRTEF
TTALQRVDLFMGQFSEVLLTSISTFIKGDLTIANLGTSEGRFMQVVVERSGPSTPHVNFL
LDSHPVSPEVIVEHTLNQNGYTLVITGKKITKIPLNGLGCRHFQSCSQCLSAPPFVQCGW
CHDKCVRSEECLEGTWTQQICLPAIYKVFPNSAPLEGGTRLTICGWDFGFRRNNKFDLKK
TRVLLGNESCTLTLSESTMNTLKCTVGPAMNKHFNMSIIISNGHGTTQYSTFSYVDPVIT
SISPKYGPMAGGTLLTLTGNYLNEGNSRHISIGGKTCTLKSVSNSILECYTPAQTISTEF
AVKLKIDLANRETSIFSYREDPIVYEIHPTKSFISGGSTITGVGKNLNSVSVPRMVINVH
EAGRNFTVACQHRENSEIICCTTPSLQQLNLQLPLKTKAFFMLDGILSKYFDLIYVHNPV
FKPFEKPVMISMGNENVLEIKGNDIDPEAVKGEVLKVGNKSCENTHLHSEAVLCTVPNDL
LKLNSELNIEWKQAISSTVLGKVIVQPDQNFTGLIAGVVSISTALLLLLGFFLWLKKRKQ
IKDLGSELVRYDARVHTPHLDRLVSARSVSPTTEMVSNESVDYRATFPEDQFPNESQNGS
CRQVQYPLTDMSPILTSGDSDISSPLLQNTVHIDLSALNPELVQAVQHVVIGPSSLIVHF
NEVIGRGHFGCVYHGTLLDNDGKKIHCAVKSLNRITDIGEVSQFLTEGIIMKDFSHPNVL
SLLGICLRSEGSPLVVLPYMKHGDLRNFIRNETHNPTVKDLIGFGLQVAKGMKYLASKKF
VHRDLAARNCMLDEKFTVKVADFGLARDMYDKEYYSVHNKTGAKLPVKWMALESLQTQKF
TTKSDVWSFGVLLWELMTRGAPPYPDVNTFDITVYLLQGRRLLQPEYCPDPLYEVMLKCW
HPKAEMRPSFSELVERISAIFSTFIGEHYVHVNATYVNVKCVAPYPELLSSEDNADDEVD
TRPASFWETS (SEQ ID NO: 18)

Cynomolgus Monkey C-MET sequence
mkapavlvpg ilvllftlvq rsngeckeal aksemnvnmk yqlpnftaet
aiqnvilheh hiflgatnyi yvlneedlqk vaeyktgpvl ehpdcfpcqd
csskanlsgg vwkdninmal vvdtyyddql iscgsvnrgt cqrhvfphnh
tadiqsevhc ifspqieepn qcpdcvvsal gakvlssvkd rfinffvgnt
inssyfphhp lhsisvrrlk etkdgfmflt dqsyidvlpe frdsypikyi
hafesnnfiy fltvqgretln aqtfhtriir fcslnsglhs ymemplecil
tekrkkrstk kevfnilqaa yvskpgagla rqigaslndd ilfgvfaqsk
pdsaepmdrs amcafpikyv ndffnkivnk nnvrclqhfy gpnhehcfnr
tllrnssgce arrdeyraef ttalqrvdlf mgqfsevllt sistfvkgdl
tianlgtseg rfmqvvvsrs gpstphvnfl ldshpvspev ivehplnqng
ytlvvtgkki tkiplnglgc rhfqscsqcl sappfvqcgw chdkcvrsee
cpsgtwtqqi clpaiykvfp tsapleggtr lticgwdfgf rrnnkfdlkk
trvllgnesc tltlseestmn tlkctvgpam nkhfnmsiii snghgttqys
tfsyvdpiit sispkygpma ggtlltltgn ylnsgnsrhi siggktctlk
svsnsilecy tpaqtistef avklkidlan retsifsyre dpivyeihpt
ksfisggsti tgvgknlhsv svprmvinvh eagrnftvac qhrsnseiic
cttpslqqln lqlplktkaf fmldgilsky fdliyvhnpv fkpfekpvmi
smgnenvlei kgndidpeav kgevlkvgnk scenihlhse avlctvpndl
lklnselnie wkqaisstvl gkvivqpdqn ftgliagvvs isialllllg
lflwlkkrkq ikdlgselvr ydarvhtphl drlvsarsvs pttemvsnes
vdyratfped qfpnssqngs crqvqypltd mspiltsgds disspllqnt
vhidlsalnp elvqavqhvv igpsslivhf nevigrghfq cvyhgtlldn
dgkkihcavk slnritdige vsqfltegii mkdfshpnvl sllgiclrse
gsplvvlpym khgdlrnfir nethnptvkd ligfglqvak gmkylaskkf TABLE 12-continued Examples of C-MET protein amino acid sequences.

vhrdlaarnc mldekftvkv adfglardmy dkeyysvhnk tgaklpvkwm
aleslqtqkf ttksdvwsfg vllwelmtrg appypdvntf ditvyllqgr
rllqpeycpd plyevmlkcw hpkaemrpsf selvsrisai fstfigehyv
hvnatyvnvk cvapypslls sednaddevdt (SEQ ID NO: 19)

SEQUENCE LISTING

```
Sequence total quantity: 255
SEQ ID NO: 1               moltype = AA  length = 118
FEATURE                    Location/Qualifiers
REGION                     1..118
                           note = Antibody MH7-3 heavy chain variable (VH) region
source                     1..118
                           mol_type = protein
                           organism = synthetic construct
SEQUENCE: 1
QVQLVQSGAE VKKPGASVKV SCKASGYTFT SYTMHWVRQA PGQGLEWMGI INPSGGSTSY   60
AQKFQGRVTM TRDTSTSTVY MELSSLRSED TAVYYCARQE ITTEFDYWGQ GTLVTVSS   118

SEQ ID NO: 2               moltype = AA  length = 111
FEATURE                    Location/Qualifiers
REGION                     1..111
                           note = Antibody MH7-3 light chain variable (VL) region
source                     1..111
                           mol_type = protein
                           organism = synthetic construct
SEQUENCE: 2
EIVLTQSPGT LSLSPGERAT LSCRASQSVS SYAQSYLHWY QQKPGQAPRL LIYRGSTRET   60
GIPDRFSGSG SGTDFTLTIS RLEPEDFAVY YCQQSKESPL TFGGGTKVEI K           111

SEQ ID NO: 3               moltype = AA  length = 118
FEATURE                    Location/Qualifiers
REGION                     1..118
                           note = Antibody MH7-2 heavy chain variable (VH) region
source                     1..118
                           mol_type = protein
                           organism = synthetic construct
SEQUENCE: 3
QVQLVQSGAE VKKPGASVKV SCKASGYTFT SYTMHWVRQA PGQGLEWMGI INPSGGSTSY   60
AQKFQGRVTM TRDTSTSTVY MELSSLRSED TAVYYCARQE ITTEFDYWGQ GTLVTVSS   118

SEQ ID NO: 4               moltype = AA  length = 111
FEATURE                    Location/Qualifiers
REGION                     1..111
                           note = Antibody MH7-2 light chain variable (VL) region
source                     1..111
                           mol_type = protein
                           organism = synthetic construct
SEQUENCE: 4
EIVLTQSPGT LSLSPGERAT LSCRASQSVS SYANSYLHWY QQKPGQAPRL LIYRGSTRET   60
GIPDRFSGSG SGTDFTLTIS RLEPEDFAVY YCQQSKESPL TFGGGTKVEI K           111

SEQ ID NO: 5               moltype = AA  length = 118
FEATURE                    Location/Qualifiers
REGION                     1..118
                           note = Antibody MH7-1 heavy chain variable (VH) region
source                     1..118
                           mol_type = protein
                           organism = synthetic construct
SEQUENCE: 5
QVQLVQSGAE VKKPGASVKV SCKASGYTFT SYTMHWVRQA PGQGLEWMGI INPSGGSTSY   60
AQKFQGRVTM TRDTSTSTVY MELSSLRSED TAVYYCARQE ITTEFDYWGQ GTLVTVSS   118

SEQ ID NO: 6               moltype = AA  length = 111
FEATURE                    Location/Qualifiers
REGION                     1..111
                           note = Antibody MH7-1 light chain variable (VL) region
source                     1..111
                           mol_type = protein
                           organism = synthetic construct
SEQUENCE: 6
EIVLTQSPGT LSLSPGERAT LSCRASQSVS SYANSYLHWY QQKPGQAPRL LIYRGSTRET   60
GIPDRFSGSG SGTDFTLTIS RLEPEDFAVY YCQQSKSESPL TFGGGTKVEI K          111
```

```
SEQ ID NO: 7              moltype = AA   length = 118
FEATURE                   Location/Qualifiers
REGION                    1..118
                          note = Antibody MH7 heavy chain variable (VH) region
source                    1..118
                          mol_type = protein
                          organism = synthetic construct
SEQUENCE: 7
QVQLVQSGAE VKKPGASVKV SCKASGYTFT SYTMHWVRQA PGQGLEWMGI INPSGGSTSY     60
AQKFQGRVTM TRDTSTSTVY MELSSLRSED TAVYYCARQE ITTEFDYWGQ GTLVTVSS     118

SEQ ID NO: 8              moltype = AA   length = 111
FEATURE                   Location/Qualifiers
REGION                    1..111
                          note = Antibody MH7 light chain variable (VL) region
source                    1..111
                          mol_type = protein
                          organism = synthetic construct
SEQUENCE: 8
EIVLTQSPGT LSLSPGERAT LSCRASQSVS SYANSYLHWY QQKPGQAPRL LIYRGSTRES     60
GIPDRFSGSG SGTDFTLTIS RLEPEDFAVY YCQQSKSEPL TFGGGTKVEI K             111

SEQ ID NO: 9              moltype = AA   length = 118
FEATURE                   Location/Qualifiers
REGION                    1..118
                          note = Antibody 08G07 heavy chain variable (VH) region
source                    1..118
                          mol_type = protein
                          organism = synthetic construct
SEQUENCE: 9
QVQLVQSGAE VKKPGASVKV SCKASGYTFT SYTMHWVRQA PGQGLEWMGW INPSGGLANY     60
AQKFQGRVTM TRDTSTSTVY MELSSLRSED TAVYYCARSE ITTDFDYWGQ GTLVTVSS     118

SEQ ID NO: 10             moltype = AA   length = 111
FEATURE                   Location/Qualifiers
REGION                    1..111
                          note = Antibody 08G07 light chain variable (VL) region
source                    1..111
                          mol_type = protein
                          organism = synthetic construct
SEQUENCE: 10
EIVLTQSPGT LSLSPGERAT LSCRASQSVD SYANSYLHWY QQKPGQAPRL LIYRGSTRES     60
GIPDRFSGSG SGTDFTLTIS RLEPEDFAVY YCQQSKSEPL TFGGGTKVEI K             111

SEQ ID NO: 11             moltype = AA   length = 327
FEATURE                   Location/Qualifiers
source                    1..327
                          mol_type = protein
                          organism = Homo sapiens
SEQUENCE: 11
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                        327

SEQ ID NO: 12             moltype = AA   length = 327
FEATURE                   Location/Qualifiers
source                    1..327
                          mol_type = protein
                          organism = Homo sapiens
SEQUENCE: 12
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                        327

SEQ ID NO: 13             moltype = AA   length = 330
FEATURE                   Location/Qualifiers
source                    1..330
                          mol_type = protein
                          organism = Homo sapiens
SEQUENCE: 13
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG   120
```

```
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                    330

SEQ ID NO: 14           moltype = AA   length = 330
FEATURE                 Location/Qualifiers
source                  1..330
                        mol_type = protein
                        organism = Homo sapiens
SEQUENCE: 14
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                    330

SEQ ID NO: 15           moltype = AA   length = 326
FEATURE                 Location/Qualifiers
source                  1..326
                        mol_type = protein
                        organism = Homo sapiens
SEQUENCE: 15
ASTKGPSVFP LAPCSRSTSE STAALGCLVK DYFPEPVTVS WNSGALTSGV HTFPAVLQSS     60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDISVEW ESNGQPENNY KTTPPMLDSD GSFFLYSKLT VDKSRWQQGN    300
VFSCSVMHEA LHNHYTQKSL SLSPGK                                        326

SEQ ID NO: 16           moltype = AA   length = 330
FEATURE                 Location/Qualifiers
source                  1..330
                        mol_type = protein
                        organism = Homo sapiens
SEQUENCE: 16
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                    330

SEQ ID NO: 17           moltype = AA   length = 329
FEATURE                 Location/Qualifiers
source                  1..329
                        mol_type = protein
                        organism = Homo sapiens
SEQUENCE: 17
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MKNQVSLTCL VKGFYPSDIA VEWESNGQPE NNYKTTPPVL DSDGSFFLYS KLTVDKSRWQ    300
QGNVFSCSVM HEALHNHYTQ KSLSLSPGK                                     329

SEQ ID NO: 18           moltype = AA   length = 1390
FEATURE                 Location/Qualifiers
source                  1..1390
                        mol_type = protein
                        organism = Homo sapiens
SEQUENCE: 18
MKAPAVLAPG ILVLLFTLVQ RSNGECKEAL AKSEMNVNMK YQLPNFTAET PIQNVILHEH     60
HIFLGATNYI YVLNEEDLQK VAEYKTGPVL EHPDCFPCQD CSSKANLSGG VWKDNINMAL    120
VVDTYYDDQL ISCGSVNRGT CQRHVFPHNH TADIQSEVHC IFSPQIEEPS QCPDCVVSAL    180
GAKVLSSVKD RFINFFVGNT INSSYFPDHP LHSISVRRLK ETKDGFMFLT DQSYIDVLPE    240
FRDSYPIKYV HAFESNNFIY FLTVQRETLD AQTPHTRIIR FCSINSGLHS YMEMPLECIL    300
TEKRKKRSTK KEVFNILQAA YVSKPGAQLA RQIGASLNDD ILFGVFAQSK PDSAEPMDRS    360
AMCAFPIKYV NDFFNKIVNK NNVRCLQHFY GPNHEHCFNR TLLRNSSGCE ARRDEYRTEF    420
TTALQRVDLF MGQFSEVLLT SISTFIKGDL TIANLGTSEG RFMQVVVSRS GPSTPHVNFL    480
LDSHPVSPEV IVEHTLNQNG YTLVITGKKI TKIPLNGLGC RHFQSCSQCL SAPPFVQCGW    540
CHDKCVRSEE CLSGTWTQQI CLPAIYKVFP NSAPLEGGTR LTICGWDPGF RRNNKFDLKK    600
TRVLLGNESC TLTLSESTMN TLKCTVGPAM NKHFNMSIII SNGHGTTQYS TFSYVDPVIT    660
SISPKYGPMA GGTLLTLTGN YLNSGNSRHI SIGGKTCTLK SVSNSILECY TPAQTISTEF    720
AVKLKIDLAN RETSIFSYRE DPIVYEIHPT KSFISGGSTI TGVGKNLNSV SVPRMVINVH    780
EAGRNFTVAC QHRSNSEIIC CTTPSLQQLN LQLPLKTKAF FMLDGILSKY FDLIYVHNPV    840
FKPFEKPVMI SMGNENVLEI KGNDIDPEAV KGEVLKVGNK SCENIHLHSE AVLCTVPNDL    900
LKLNSELNIE WKQAISSTVL GKVIVQPDQN FTGLIAGVVS ISTALLLLLG FFLWLKKRKQ    960
```

```
IKDLGSELVR YDARVHTPHL DRLVSARSVS PTTEMVSNES VDYRATFPED QFPNSSQNGS    1020
CRQVQYPLTD MSPILTSGDS DISSPLLQNT VHIDLSALNP ELVQAVQHVV IGPSSLIVHF    1080
NEVIGRGHFG CVYHGTLLDN DGKKIHCAVK SLNRITDIGE VSQFLTEGII MKDFSHPNVL    1140
SLLGICLRSE GSPLVVLPYM KHGDLRNFIR NETHNPTVKD LIGFGLQVAK GMKYLASKKF    1200
VHRDLAARNC MLDEKFTVKV ADFGLARDMY DKEYYSHNK  TGAKLPVKWM ALESLQTQKF    1260
TTKSDVWSFG VLLWELMTRG APPYPDVNTF DITVYLLQGR RLLQPEYCPD PLYEVMLKCW    1320
HPKAEMRPSF SELVSRISAI FSTFIGEHYV HVNATYVNVK CVAPYPSLLS SEDNADDEVD    1380
TRPASFWETS                                                          1390

SEQ ID NO: 19              moltype = AA   length = 1381
FEATURE                    Location/Qualifiers
source                     1..1381
                           mol_type = protein
                           organism = Macaca fascicularis
SEQUENCE: 19
MKAPAVLVPG ILVLLFTLVQ RSNGECKEAL AKSEMNVNMK YQLPNFTAET AIQNVILHEH    60
HIFLGATNYI YVLNEEDLQK VAEYKTGPVL EHPDCFPCQD CSSKANLSGG VWKDNINMAL    120
VVDTYYDDQL ISCGSVNRGT CQRHVFPHHP TADIQSEVHC IFSPQIEEPN QCPDCVVSAL    180
GAKVLSSVKD RFINFFVGNT INSSYFPHHP LHSISVRRLK ETKDGFMFLT DQSYIDVLPE    240
FRDSYPIKYI HAFESNNFIY FLTVQRETLN AQTFHTRIIR FCSLNSGLHS YMEMPLECIL    300
TEKRKKRSTK KEVFNILQAA YVSKPGAQLA RQIGASLNDD ILFGVFAQSK PDSAEPMDRS    360
AMCAFPIKYV NDFFNKIVNK NNVRCLQHFY GPNHEHCFNR ARRDEYRAEF              420
TTALQRVDLF MGQFSEVLLT SISTFVKGDL TIANLGTSEG RFMQVVVSRS GPSTPHVNFL    480
LDSHPVSPEV IVEHPLNQNG YTLVVTGKKI TKIPLNGLGC RHFQSCSQCL SAPPFVQCGW    540
CHDKCVRSEE CPSGTWTQQI CLPAIYKVFP TSAPLEGGTR LTICGWDFGF RRNNKFDLKK    600
TRVLLGNESC TLTLSESTMN TLKCTVGPAM NKHFNMSIII SNGHGTTQYS TFSYVDPIIT    660
SISPKYGPMA GGTLLTLTGN YLNSGNSRHI SIGGKTCTLK SVSNSILECY TPAQTISTEF    720
AVKLKIDLAN RETSIFSYRE DPIVYEIHPT KSFISGGSTI TGVGKNLHSV SVPRMVINVH    780
EAGRNFTVAC QHRSNSEIIC CTTPSLQQLN LQLPLKTKAF FMLDGILSKY FDLIYVHNPV    840
FKPFEKPVMI SMGNENVLEI KGNDIDPEAV KGEVLKVGNK SCENIHLHSE AVLCTVPNDL    900
LKLNSELNIE WKQAISSTVL GKVIVQPDQN FTGLIAGVVS ISIALLLLLG LFLWLKKRKQ    960
IKDLGSELVR YDARVHTPHL DRLVSARSVS PTTEMVSNES VDYRATFPED QFPNSSQNGS    1020
CRQVQYPLTD MSPILTSGDS DISSPLLQNT VHIDLSALNP ELVQAVQHVV IGPSSLIVHF    1080
NEVIGRGHFG CVYHGTLLDN DGKKIHCAVK SLNRITDIGE VSQFLTEGII MKDFSHPNVL    1140
SLLGICLRSE GSPLVVLPYM KHGDLRNFIR NETHNPTVKD LIGFGLQVAK GMKYLASKKF    1200
VHRDLAARNC MLDEKFTVKV ADFGLARDMY DKEYYSVHNK TGAKLPVKWM ALESLQTQKF    1260
TTKSDVWSFG VLLWELMTRG APPYPDVNTF DITVYLLQGR RLLQPEYCPD PLYEVMLKCW    1320
HPKAEMRPSF SELVSRISAI FSTFIGEHYV HVNATYVNVK CVAPYPSLLS SEDNADDEVD    1380
T                                                                   1381

SEQ ID NO: 20              moltype = AA   length = 5
FEATURE                    Location/Qualifiers
source                     1..5
                           mol_type = protein
                           organism = Homo sapiens
SEQUENCE: 20
RDELT                                                               5

SEQ ID NO: 21              moltype = AA   length = 4
FEATURE                    Location/Qualifiers
source                     1..4
                           mol_type = protein
                           organism = Homo sapiens
SEQUENCE: 21
REEM                                                                4

SEQ ID NO: 22              moltype = AA   length = 10
FEATURE                    Location/Qualifiers
REGION                     1..10
                           note = anti-C-MET antibody molecule or antigen-binding
                            portion HCDR1
VARIANT                    3
                           note = I or or any other amino acid
VARIANT                    6
                           note = A or any other amino acid
VARIANT                    8
                           note = Y or any other amino acid
source                     1..10
                           mol_type = protein
                           organism = synthetic construct
SEQUENCE: 22
GYXFTXYXMH                                                          10

SEQ ID NO: 23              moltype = AA   length = 19
FEATURE                    Location/Qualifiers
REGION                     1..19
                           note = anti-C-MET antibody molecule or antigen-binding
                            portion HCDR2
VARIANT                    3
```

```
                        note = W or any other amino acid
VARIANT                 5
                        note = K or any other amino acid
VARIANT                 7
                        note = N or any other amino acid
VARIANT                 8
                        note = N or any other amino acid
VARIANT                 10
                        note = L or any other amino acid
VARIANT                 11
                        note = A or any other amino acid
VARIANT                 12
                        note = N or any other amino acid
source                  1..19
                        mol_type = protein
                        organism = synthetic construct
SEQUENCE: 23
MGXIXPXXGX XXYAQKFQG                                                            19

SEQ ID NO: 24           moltype = AA  length = 9
FEATURE                 Location/Qualifiers
REGION                  1..9
                        note = anti-C-MET antibody molecule or antigen-binding
                         portion HCDR3
VARIANT                 1
                        note = S or any other amino acid
VARIANT                 6
                        note = E or any other amino acid
VARIANT                 7
                        note = F or any other amino acid
VARIANT                 9
                        note = Y or any other amino acid
source                  1..9
                        mol_type = protein
                        organism = synthetic construct
SEQUENCE: 24
XEITTXXDX                                                                        9

SEQ ID NO: 25           moltype = AA  length = 10
FEATURE                 Location/Qualifiers
REGION                  1..10
                        note = 224G11 murine/humanized antibody HCDR1
source                  1..10
                        mol_type = protein
                        organism = synthetic construct
SEQUENCE: 25
GYIFTAYTMH                                                                      10

SEQ ID NO: 26           moltype = AA  length = 19
FEATURE                 Location/Qualifiers
REGION                  1..19
                        note = 224G11 murine/humanized antibody HCDR2
source                  1..19
                        mol_type = protein
                        organism = synthetic construct
SEQUENCE: 26
MGWIKPNNGL ANYAQKFQG                                                            19

SEQ ID NO: 27           moltype = AA  length = 9
FEATURE                 Location/Qualifiers
REGION                  1..9
                        note = 224G11 murine/humanized antibody HCDR3
source                  1..9
                        mol_type = protein
                        organism = synthetic construct
SEQUENCE: 27
SEITTEFDY                                                                        9

SEQ ID NO: 28           moltype = AA  length = 15
FEATURE                 Location/Qualifiers
REGION                  1..15
                        note = anti-C-MET antibody molecule or antigen-binding
                         portion LCDR1
VARIANT                 7
                        note = D or any other amino acid
VARIANT                 11
                        note = N or any other amino acid
VARIANT                 13
                        note = F or any other amino acid
```

```
VARIANT                 15
                        note = H or any other amino acid
source                  1..15
                        mol_type = protein
                        organism = synthetic construct
SEQUENCE: 28
RASQSVXSYA XSXLX                                                           15

SEQ ID NO: 29           moltype =    length =
SEQUENCE: 29
000

SEQ ID NO: 30           moltype = AA   length = 9
FEATURE                 Location/Qualifiers
REGION                  1..9
                        note = anti-C-MET antibody molecule or antigen-binding
                         portion LCDR3
VARIANT                 3
                        note = S or any other amino acid
VARIANT                 4
                        note = K or any other amino acid
VARIANT                 5
                        note = E or any other amino acid
VARIANT                 6
                        note = D or any other amino acid
source                  1..9
                        mol_type = protein
                        organism = synthetic construct
SEQUENCE: 30
QQXXXXPLT                                                                   9

SEQ ID NO: 31           moltype = AA   length = 15
FEATURE                 Location/Qualifiers
REGION                  1..15
                        note = 224G11 murine/humanized antibody LCDR1
source                  1..15
                        mol_type = protein
                        organism = synthetic construct
SEQUENCE: 31
KSSESVDSYA NSFLH                                                           15

SEQ ID NO: 32           moltype = AA   length = 7
FEATURE                 Location/Qualifiers
REGION                  1..7
                        note = 224G11 murine/humanized antibody LCDR2
source                  1..7
                        mol_type = protein
                        organism = synthetic construct
SEQUENCE: 32
RASTRES                                                                     7

SEQ ID NO: 33           moltype = AA   length = 9
FEATURE                 Location/Qualifiers
REGION                  1..9
                        note = 224G11 murine/humanized antibody LCDR3
source                  1..9
                        mol_type = protein
                        organism = synthetic construct
SEQUENCE: 33
QQSKEDPLT                                                                   9

SEQ ID NO: 34           moltype = AA   length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 34
GYTFTSYTMH                                                                 10

SEQ ID NO: 35           moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
```

```
                                     -continued

SEQUENCE: 35
MGIINPSGGS TSYAQKFQG                                                  19

SEQ ID NO: 36           moltype = AA   length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 36
QEITTEFDY                                                              9

SEQ ID NO: 37           moltype = AA   length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 37
RASQSVSSYA NSYLH                                                      15

SEQ ID NO: 38           moltype = AA   length = 7
FEATURE                 Location/Qualifiers
REGION                  1..7
                        note = anti-C-MET antibody molecule or antigen-binding
                         portion LCDR2
source                  1..7
                        mol_type = protein
                        organism = synthetic construct
SEQUENCE: 38
RGSTRES                                                                7

SEQ ID NO: 39           moltype = AA   length = 9
FEATURE                 Location/Qualifiers
REGION                  1..9
                        note = anti-C-MET antibody molecule or antigen-binding
                         portion LCDR3
source                  1..9
                        mol_type = protein
                        organism = synthetic construct
SEQUENCE: 39
QQSKSEPLT                                                              9

SEQ ID NO: 40           moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 40
MGWINPSGGS TSYAQKFQG                                                  19

SEQ ID NO: 41           moltype = AA   length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 41
GYTFTSYAMH                                                            10

SEQ ID NO: 42           moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 42
```

```
MGWINPNGGS TSYAQKFQG                                                    19

SEQ ID NO: 43           moltype = AA  length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 43
GYIFTSYSMH                                                              10

SEQ ID NO: 44           moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 44
MGWINPSNGL ANYAQKFQG                                                    19

SEQ ID NO: 45           moltype = AA  length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 45
QEITTEFDI                                                               9

SEQ ID NO: 46           moltype = AA  length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 46
RASQSVESYA QSYLH                                                        15

SEQ ID NO: 47           moltype = AA  length = 9
FEATURE                 Location/Qualifiers
REGION                  1..9
                        note = anti-C-MET antibody molecule or antigen-binding
                         portion LCDR3
source                  1..9
                        mol_type = protein
                        organism = synthetic construct
SEQUENCE: 47
QQSKSDPLT                                                               9

SEQ ID NO: 48           moltype = AA  length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 48
GYIFTSYTMH                                                              10

SEQ ID NO: 49           moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 49
MGWINPNGGL ASYAQKFQG                                                    19
```

```
SEQ ID NO: 50              moltype = AA   length = 9
FEATURE                    Location/Qualifiers
REGION                     1..9
                           note = anti-C-MET antibody molecule or antigen-binding
                            portion HCDR3
source                     1..9
                           mol_type = protein
                           organism = synthetic construct
SEQUENCE: 50
SEITTEQDY                                                                9

SEQ ID NO: 51              moltype = AA   length = 15
FEATURE                    Location/Qualifiers
REGION                     1..15
                           note = anti-C-MET antibody molecule or antigen-binding
                            portion LCDR1
source                     1..15
                           mol_type = protein
                           organism = synthetic construct
SEQUENCE: 51
RASQSVDSYA NSYLH                                                        15

SEQ ID NO: 52              moltype = AA   length = 15
FEATURE                    Location/Qualifiers
REGION                     1..15
                           note = anti-C-MET antibody molecule or antigen-binding
                            portion LCDR1
source                     1..15
                           mol_type = protein
                           organism = synthetic construct
SEQUENCE: 52
RASQSVESYA NSYLH                                                        15

SEQ ID NO: 53              moltype = AA   length = 9
FEATURE                    Location/Qualifiers
REGION                     1..9
                           note = anti-C-MET antibody molecule or antigen-binding
                            portion LCDR3
source                     1..9
                           mol_type = protein
                           organism = synthetic construct
SEQUENCE: 53
QQYGSEPLT                                                                9

SEQ ID NO: 54              moltype = AA   length = 19
FEATURE                    Location/Qualifiers
REGION                     1..19
                           note = anti-C-MET antibody molecule or antigen-binding
                            portion HCDR2
source                     1..19
                           mol_type = protein
                           organism = synthetic construct
SEQUENCE: 54
MGWINPSGGL ANYAQKFQG                                                    19

SEQ ID NO: 55              moltype = AA   length = 9
FEATURE                    Location/Qualifiers
REGION                     1..9
                           note = anti-C-MET antibody molecule or antigen-binding
                            portion HCDR3
source                     1..9
                           mol_type = protein
                           organism = synthetic construct
SEQUENCE: 55
SEITTDFDY                                                                9

SEQ ID NO: 56              moltype = AA   length = 7
FEATURE                    Location/Qualifiers
REGION                     1..7
                           note = anti-C-MET antibody molecule or antigen-binding
                            portion LCDR2
source                     1..7
                           mol_type = protein
                           organism = synthetic construct
SEQUENCE: 56
RGSTRET                                                                  7

SEQ ID NO: 57              moltype = AA   length = 15
FEATURE                    Location/Qualifiers
```

```
REGION                  1..15
                        note = anti-C-MET antibody molecule or antigen-binding
                         portion LCDR1
source                  1..15
                        mol_type = protein
                        organism = synthetic construct
SEQUENCE: 57
RASQSVSSYA QSYLH                                                              15

SEQ ID NO: 58           moltype = AA  length = 15
FEATURE                 Location/Qualifiers
REGION                  1..15
                        note = anti-C-MET antibody molecule or antigen-binding
                         portion consensus LCDR1
source                  1..15
                        mol_type = protein
                        organism = synthetic construct
SEQUENCE: 58
KSSESVDSYA NSFLH                                                              15

SEQ ID NO: 59           moltype = AA  length = 7
FEATURE                 Location/Qualifiers
REGION                  1..7
                        note = anti-C-MET antibody molecule or antigen-binding
                         portion consensus LCDR2
source                  1..7
                        mol_type = protein
                        organism = synthetic construct
SEQUENCE: 59
RASTRES                                                                        7

SEQ ID NO: 60           moltype = AA  length = 9
FEATURE                 Location/Qualifiers
REGION                  1..9
                        note = anti-C-MET antibody molecule or antigen-binding
                         portion consensus LCDR3
source                  1..9
                        mol_type = protein
                        organism = synthetic construct
SEQUENCE: 60
QQSKEDPLT                                                                      9

SEQ ID NO: 61           moltype = AA  length = 10
FEATURE                 Location/Qualifiers
REGION                  1..10
                        note = anti-C-MET antibody molecule or antigen-binding
                         portion consensus HCDR1
source                  1..10
                        mol_type = protein
                        organism = synthetic construct
SEQUENCE: 61
GYIFTAYTMH                                                                    10

SEQ ID NO: 62           moltype = AA  length = 19
FEATURE                 Location/Qualifiers
REGION                  1..19
                        note = anti-C-MET antibody molecule or antigen-binding
                         portion consensus HCDR2
source                  1..19
                        mol_type = protein
                        organism = synthetic construct
SEQUENCE: 62
MGWIKPNNGL ANYAQKFQG                                                          19

SEQ ID NO: 63           moltype = AA  length = 9
FEATURE                 Location/Qualifiers
REGION                  1..9
                        note = anti-C-MET antibody molecule or antigen-binding
                         portion consensus HCDR3
source                  1..9
                        mol_type = protein
                        organism = synthetic construct
SEQUENCE: 63
SEITTEFDY                                                                      9

SEQ ID NO: 64           moltype = AA  length = 10
FEATURE                 Location/Qualifiers
REGION                  1..10
                        note = anti-C-MET antibody molecule or antigen-binding
```

```
                        portion HCDR1
VARIANT                 3
                        note = I or T
VARIANT                 6
                        note = A or S
VARIANT                 8
                        note = Y, S, T or A
source                  1..10
                        mol_type = protein
                        organism = synthetic construct
SEQUENCE: 64
GYXFTXYXMH                                                              10

SEQ ID NO: 65           moltype = AA  length = 19
FEATURE                 Location/Qualifiers
REGION                  1..19
                        note = anti-C-MET antibody molecule or antigen-binding
                         portion HCDR2
VARIANT                 3
                        note = W or I
VARIANT                 5
                        note = K or N
VARIANT                 7
                        note = N or S
VARIANT                 8
                        note = N or G
VARIANT                 10
                        note = L or S
VARIANT                 11
                        note = A or T
VARIANT                 12
                        note = N or S
source                  1..19
                        mol_type = protein
                        organism = synthetic construct
SEQUENCE: 65
MGXIXPXXGX XXYAQKFQG                                                    19

SEQ ID NO: 66           moltype = AA  length = 9
FEATURE                 Location/Qualifiers
REGION                  1..9
                        note = anti-C-MET antibody molecule or antigen-binding
                         portion HCDR3
VARIANT                 1
                        note = S, A, E, H, M, Q, T or V
VARIANT                 6
                        note = E or D
VARIANT                 7
                        note = F or L
VARIANT                 9
                        note = Y, A, E, F, I, K, L, M, Q, S, V or W
source                  1..9
                        mol_type = protein
                        organism = synthetic construct
SEQUENCE: 66
XEITTXXDX                                                               9

SEQ ID NO: 67           moltype = AA  length = 10
FEATURE                 Location/Qualifiers
REGION                  1..10
                        note = anti-C-MET antibody molecule or antigen-binding
                         portion HCDR1
VARIANT                 8
                        note = A, S or T
source                  1..10
                        mol_type = protein
                        organism = synthetic construct
SEQUENCE: 67
GYTFTSYXMH                                                              10

SEQ ID NO: 68           moltype = AA  length = 19
FEATURE                 Location/Qualifiers
REGION                  1..19
                        note = anti-C-MET antibody molecule or antigen-binding
                         portion HCDR2
VARIANT                 3
                        note = W or I
source                  1..19
                        mol_type = protein
```

```
                                    organism = synthetic construct
SEQUENCE: 68
MGXINPSGGS TSYAQKFQG                                                            19

SEQ ID NO: 69           moltype = AA   length = 9
FEATURE                 Location/Qualifiers
REGION                  1..9
                        note = anti-C-MET antibody molecule or antigen-binding
                         portion HCDR3
VARIANT                 1
                        note = S, A, E, Q or T
VARIANT                 6
                        note = E or D
VARIANT                 9
                        note = Y or I
source                  1..9
                        mol_type = protein
                        organism = synthetic construct
SEQUENCE: 69
XEITTXFDX                                                                        9

SEQ ID NO: 70           moltype = AA   length = 15
FEATURE                 Location/Qualifiers
REGION                  1..15
                        note = anti-C-MET antibody molecule or antigen-binding
                         portion LCDR1
VARIANT                 7
                        note = D, S or E
VARIANT                 11
                        note = N or Q
VARIANT                 13
                        note = F or Y
VARIANT                 15
                        note = H or A
source                  1..15
                        mol_type = protein
                        organism = synthetic construct
SEQUENCE: 70
RASQSVXSYA XSXLX                                                                15

SEQ ID NO: 71           moltype =    length =
SEQUENCE: 71
000

SEQ ID NO: 72           moltype = AA   length = 9
FEATURE                 Location/Qualifiers
REGION                  1..9
                        note = anti-C-MET antibody molecule or antigen-binding
                         portion LCDR3
VARIANT                 3
                        note = S or Y
VARIANT                 4
                        note = K or G
VARIANT                 5
                        note = E, D or S
VARIANT                 6
                        note = D, S, E or R
source                  1..9
                        mol_type = protein
                        organism = synthetic construct
SEQUENCE: 72
QQXXXXPLT                                                                        9

SEQ ID NO: 73           moltype = AA   length = 15
FEATURE                 Location/Qualifiers
REGION                  1..15
                        note = anti-C-MET antibody molecule or antigen-binding
                         portion LCDR1
VARIANT                 7
                        note = D, S or E
VARIANT                 11
                        note = N or Q
source                  1..15
                        mol_type = protein
                        organism = synthetic construct
SEQUENCE: 73
RASQSVXSYA XSYLH                                                                15

SEQ ID NO: 74           moltype = AA   length = 7
```

```
FEATURE              Location/Qualifiers
REGION               1..7
                     note = anti-C-MET antibody molecule or antigen-binding
                      portion LCDR2
VARIANT              7
                     note = T or S
source               1..7
                     mol_type = protein
                     organism = synthetic construct
SEQUENCE: 74
RGSTREX                                                                       7

SEQ ID NO: 75        moltype = AA  length = 9
FEATURE              Location/Qualifiers
REGION               1..9
                     note = anti-C-MET antibody molecule or antigen-binding
                      portion LCDR3
VARIANT              3
                     note = S or Y
VARIANT              4
                     note = K or G
VARIANT              5
                     note = E or S
VARIANT              6
                     note = D, S or E
source               1..9
                     mol_type = protein
                     organism = synthetic construct
SEQUENCE: 75
QQXXXXPLT                                                                     9

SEQ ID NO: 76        moltype = AA  length = 9
FEATURE              Location/Qualifiers
REGION               1..9
                     note = anti-C-MET antibody molecule or antigen-binding
                      portion LCDR3
source               1..9
                     mol_type = protein
                     organism = synthetic construct
SEQUENCE: 76
QQSKSDPLT                                                                     9

SEQ ID NO: 77        moltype = AA  length = 7
FEATURE              Location/Qualifiers
REGION               1..7
                     note = anti-C-MET antibody molecule or antigen-binding
                      portion LCDR2
source               1..7
                     mol_type = protein
                     organism = synthetic construct
SEQUENCE: 77
RASTRET                                                                       7

SEQ ID NO: 78        moltype = AA  length = 10
FEATURE              Location/Qualifiers
REGION               1..10
                     note = anti-C-MET antibody molecule or antigen-binding
                      portion HCDR1
source               1..10
                     mol_type = protein
                     organism = synthetic construct
SEQUENCE: 78
GYTFTSYSMH                                                                    10

SEQ ID NO: 79        moltype = AA  length = 19
FEATURE              Location/Qualifiers
REGION               1..19
                     note = anti-C-MET antibody molecule or antigen-binding
                      portion HCDR2
source               1..19
                     mol_type = protein
                     organism = synthetic construct
SEQUENCE: 79
MGWINPNGGL TNYAQKFRG                                                          19

SEQ ID NO: 80        moltype = AA  length = 9
FEATURE              Location/Qualifiers
REGION               1..9
                     note = anti-C-MET antibody molecule or antigen-binding
```

```
                              portion HCDR3
source                        1..9
                              mol_type = protein
                              organism = synthetic construct
SEQUENCE: 80
EEITTEFDY                                                                        9

SEQ ID NO: 81                 moltype = AA  length = 19
FEATURE                       Location/Qualifiers
REGION                        1..19
                              note = anti-C-MET antibody molecule or antigen-binding
                              portion HCDR2
source                        1..19
                              mol_type = protein
                              organism = synthetic construct
SEQUENCE: 81
MGWINPNNGS TNYAQKFQG                                                             19

SEQ ID NO: 82                 moltype = AA  length = 9
FEATURE                       Location/Qualifiers
REGION                        1..9
                              note = anti-C-MET antibody molecule or antigen-binding
                              portion LCDR3
source                        1..9
                              mol_type = protein
                              organism = synthetic construct
SEQUENCE: 82
QQSKEEPLT                                                                        9

SEQ ID NO: 83                 moltype = AA  length = 10
FEATURE                       Location/Qualifiers
REGION                        1..10
                              note = anti-C-MET antibody molecule or antigen-binding
                              portion HCDR1
source                        1..10
                              mol_type = protein
                              organism = synthetic construct
SEQUENCE: 83
GYIFTAYSMH                                                                       10

SEQ ID NO: 84                 moltype = AA  length = 19
FEATURE                       Location/Qualifiers
REGION                        1..19
                              note = anti-C-MET antibody molecule or antigen-binding
                              portion HCDR2
source                        1..19
                              mol_type = protein
                              organism = synthetic construct
SEQUENCE: 84
MGIIKPSNGS TNYAQKFQG                                                             19

SEQ ID NO: 85                 moltype = AA  length = 9
FEATURE                       Location/Qualifiers
REGION                        1..9
                              note = anti-C-MET antibody molecule or antigen-binding
                              portion HCDR3
source                        1..9
                              mol_type = protein
                              organism = synthetic construct
SEQUENCE: 85
AEITTEFDY                                                                        9

SEQ ID NO: 86                 moltype = AA  length = 19
FEATURE                       Location/Qualifiers
REGION                        1..19
                              note = anti-C-MET antibody molecule or antigen-binding
                              portion HCDR2
source                        1..19
                              mol_type = protein
                              organism = synthetic construct
SEQUENCE: 86
MGWIKPNNGS ASYAQKFQG                                                             19

SEQ ID NO: 87                 moltype = AA  length = 19
FEATURE                       Location/Qualifiers
REGION                        1..19
                              note = anti-C-MET antibody molecule or antigen-binding
                              portion HCDR2
source                        1..19
```

```
                        mol_type = protein
                        organism = synthetic construct
SEQUENCE: 87
MGWIKPNNGS TNYAQKFQG                                                    19

SEQ ID NO: 88           moltype = AA   length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 88
TEITTEFDY                                                                9

SEQ ID NO: 89           moltype = AA   length = 9
FEATURE                 Location/Qualifiers
REGION                  1..9
                        note = anti-C-MET antibody molecule or antigen-binding
                         portion LCDR3
source                  1..9
                        mol_type = protein
                        organism = synthetic construct
SEQUENCE: 89
QQSGSSPLT                                                                9

SEQ ID NO: 90           moltype = AA   length = 9
FEATURE                 Location/Qualifiers
REGION                  1..9
                        note = anti-C-MET antibody molecule or antigen-binding
                         portion LCDR3
source                  1..9
                        mol_type = protein
                        organism = synthetic construct
SEQUENCE: 90
QQYGSSPLT                                                                9

SEQ ID NO: 91           moltype = AA   length = 9
FEATURE                 Location/Qualifiers
REGION                  1..9
                        note = HAF peptide motif
source                  1..9
                        mol_type = protein
                        organism = synthetic construct
SEQUENCE: 91
LLIYRASTR                                                                9

SEQ ID NO: 92           moltype = AA   length = 9
FEATURE                 Location/Qualifiers
REGION                  1..9
                        note = HAF peptide motif
source                  1..9
                        mol_type = protein
                        organism = synthetic construct
SEQUENCE: 92
IYRASTRES                                                                9

SEQ ID NO: 93           moltype = AA   length = 9
FEATURE                 Location/Qualifiers
REGION                  1..9
                        note = LAF peptide motif
source                  1..9
                        mol_type = protein
                        organism = synthetic construct
SEQUENCE: 93
VAVYYCQQS                                                                9

SEQ ID NO: 94           moltype = AA   length = 8
FEATURE                 Location/Qualifiers
REGION                  1..8
                        note = HAF peptide motif
source                  1..8
                        mol_type = protein
                        organism = synthetic construct
SEQUENCE: 94
IFTAYTMH                                                                 8

SEQ ID NO: 95           moltype = AA   length = 9
```

```
FEATURE                 Location/Qualifiers
REGION                  1..9
                        note = HAF peptide motif
source                  1..9
                        mol_type = protein
                        organism = synthetic construct
SEQUENCE: 95
VYYCARSEI                                                                     9

SEQ ID NO: 96           moltype = AA   length = 9
FEATURE                 Location/Qualifiers
REGION                  1..9
                        note = LAF peptide motif
source                  1..9
                        mol_type = protein
                        organism = synthetic construct
SEQUENCE: 96
MGWIKPNNG                                                                     9

SEQ ID NO: 97           moltype = AA   length = 9
FEATURE                 Location/Qualifiers
REGION                  1..9
                        note = HAF peptide motif
source                  1..9
                        mol_type = protein
                        organism = synthetic construct
SEQUENCE: 97
IFTAYTMHW                                                                     9

SEQ ID NO: 98           moltype = AA   length = 9
FEATURE                 Location/Qualifiers
REGION                  1..9
                        note = germline epitope peptide
source                  1..9
                        mol_type = protein
                        organism = synthetic construct
SEQUENCE: 98
LEWMGIINP                                                                     9

SEQ ID NO: 99           moltype = AA   length = 9
FEATURE                 Location/Qualifiers
REGION                  1..9
                        note = germline epitope peptide
source                  1..9
                        mol_type = protein
                        organism = synthetic construct
SEQUENCE: 99
MGIINPSGG                                                                     9

SEQ ID NO: 100          moltype = AA   length = 10
FEATURE                 Location/Qualifiers
source                  1..10
                        mol_type = protein
                        organism = Mus musculus
SEQUENCE: 100
GYIFTAYTMH                                                                    10

SEQ ID NO: 101          moltype = AA   length = 5
FEATURE                 Location/Qualifiers
source                  1..5
                        mol_type = protein
                        organism = Mus musculus
SEQUENCE: 101
AYTMH                                                                         5

SEQ ID NO: 102          moltype = AA   length = 7
FEATURE                 Location/Qualifiers
source                  1..7
                        mol_type = protein
                        organism = Mus musculus
SEQUENCE: 102
GYIFTAY                                                                       7

SEQ ID NO: 103          moltype = AA   length = 8
FEATURE                 Location/Qualifiers
source                  1..8
                        mol_type = protein
                        organism = Mus musculus
SEQUENCE: 103
```

```
GYIFTAYT                                                                  8

SEQ ID NO: 104         moltype = AA  length = 12
FEATURE                Location/Qualifiers
source                 1..12
                       mol_type = protein
                       organism = Mus musculus SEQUENCE: 104
ASGYIFTAYT MH                                                            12

SEQ ID NO: 105         moltype = AA  length = 6
FEATURE                Location/Qualifiers
source                 1..6
                       mol_type = protein
                       organism = Mus musculus SEQUENCE: 105
TAYTMH                                                                    6

SEQ ID NO: 106         moltype = AA  length = 19
FEATURE                Location/Qualifiers
source                 1..19
                       mol_type = protein
                       organism = Mus musculus SEQUENCE: 106
MGWIKPNNGL ANYAQKFQG                                                     19

SEQ ID NO: 107         moltype = AA  length = 17
FEATURE                Location/Qualifiers
source                 1..17
                       mol_type = protein
                       organism = Mus musculus SEQUENCE: 107
WIKPNNGLAN YAQKFQG                                                       17

SEQ ID NO: 108         moltype = AA  length = 6
FEATURE                Location/Qualifiers
source                 1..6
                       mol_type = protein
                       organism = Mus musculus SEQUENCE: 108
KPNNGL                                                                    6

SEQ ID NO: 109         moltype = AA  length = 8
FEATURE                Location/Qualifiers
source                 1..8
                       mol_type = protein
                       organism = Mus musculus SEQUENCE: 109
IKPNNGLA                                                                  8

SEQ ID NO: 110         moltype = AA  length = 16
FEATURE                Location/Qualifiers
source                 1..16
                       mol_type = protein
                       organism = Mus musculus SEQUENCE: 110
IKPNNGLANY AQKFQG                                                        16

SEQ ID NO: 111         moltype = AA  length = 10
FEATURE                Location/Qualifiers
source                 1..10
                       mol_type = protein
                       organism = Mus musculus SEQUENCE: 111
WIKPNNGLAN                                                               10

SEQ ID NO: 112         moltype = AA  length = 12
FEATURE                Location/Qualifiers
source                 1..12
                       mol_type = protein
                       organism = Mus musculus SEQUENCE: 112
MGWIKPNNGL AN                                                            12

SEQ ID NO: 113         moltype = AA  length = 9
FEATURE                Location/Qualifiers
source                 1..9
                       mol_type = protein
                       organism = Mus musculus
```

```
SEQUENCE: 113
SEITTEFDY                                                                        9

SEQ ID NO: 114          moltype = AA  length = 11
FEATURE                 Location/Qualifiers
source                  1..11
                        mol_type = protein
                        organism = Mus musculus
SEQUENCE: 114
ARSEITTEFD Y                                                                    11

SEQ ID NO: 115          moltype = AA  length = 8
FEATURE                 Location/Qualifiers
source                  1..8
                        mol_type = protein
                        organism = Mus musculus
SEQUENCE: 115
SEITTEFD                                                                         8

SEQ ID NO: 116          moltype = AA  length = 10
FEATURE                 Location/Qualifiers
source                  1..10
                        mol_type = protein
                        organism = Mus musculus
SEQUENCE: 116
ARSEITTEFD                                                                      10

SEQ ID NO: 117          moltype = AA  length = 15
FEATURE                 Location/Qualifiers
source                  1..15
                        mol_type = protein
                        organism = Mus musculus
SEQUENCE: 117
KSSESVDSYA NSFLH                                                                15

SEQ ID NO: 118          moltype = AA  length = 10
FEATURE                 Location/Qualifiers
source                  1..10
                        mol_type = protein
                        organism = Mus musculus
SEQUENCE: 118
ESVDSYANSF                                                                      10

SEQ ID NO: 119          moltype = AA  length = 12
FEATURE                 Location/Qualifiers
source                  1..12
                        mol_type = protein
                        organism = Mus musculus
SEQUENCE: 119
SSESVDSYAN SF                                                                   12

SEQ ID NO: 120          moltype = AA  length = 12
FEATURE                 Location/Qualifiers
source                  1..12
                        mol_type = protein
                        organism = Mus musculus
SEQUENCE: 120
VDSYANSFLH WY                                                                   12

SEQ ID NO: 121          moltype = AA  length = 7
FEATURE                 Location/Qualifiers
source                  1..7
                        mol_type = protein
                        organism = Mus musculus
SEQUENCE: 121
RASTRES                                                                          7

SEQ ID NO: 122          moltype = AA  length = 10
FEATURE                 Location/Qualifiers
source                  1..10
                        mol_type = protein
                        organism = Mus musculus
SEQUENCE: 122
LLIYRASTRE                                                                      10

SEQ ID NO: 123          moltype = AA  length = 9
FEATURE                 Location/Qualifiers
source                  1..9
                        mol_type = protein
```

```
                        organism = Mus musculus
SEQUENCE: 123
QQSKEDPLT                                                               9

SEQ ID NO: 124          moltype = AA  length = 6
FEATURE                 Location/Qualifiers
source                  1..6
                        mol_type = protein
                        organism = Mus musculus
SEQUENCE: 124
SKEDPL                                                                  6

SEQ ID NO: 125          moltype = AA  length = 8
FEATURE                 Location/Qualifiers
source                  1..8
                        mol_type = protein
                        organism = Mus musculus
SEQUENCE: 125
QQSKEDPL                                                                8

SEQ ID NO: 126          moltype = AA  length = 118
FEATURE                 Location/Qualifiers
REGION                  1..118
                        note = h224G11-VH IGHV1-2
source                  1..118
                        mol_type = protein
                        organism = synthetic construct
SEQUENCE: 126
QVQLVQSGAE VKKPGASVKV SCKASGYIFT AYTMHWVRQA PGQGLEWMGW IKPNNGLANY        60
AQKFQGRVTM TRDTSISTAY MELSRLRSDD TAVYYCARSE ITTEFDYWGQ GTLVTVSS         118

SEQ ID NO: 127          moltype = AA  length = 118
FEATURE                 Location/Qualifiers
REGION                  1..118
                        note = VH graft IGHV1-46
source                  1..118
                        mol_type = protein
                        organism = synthetic construct
SEQUENCE: 127
QVQLVQSGAE VKKPGASVKV SCKASGYIFT AYTMHWVRQA PGQGLEWMGW IKPNNGLANY        60
AQKFQGRVTM TRDTSTSTVY MELSSLRSED TAVYYCARSE ITTEFDYWGQ GTLVTVSS         118

SEQ ID NO: 128          moltype = AA  length = 111
FEATURE                 Location/Qualifiers
REGION                  1..111
                        note = h224G11-VL IGKV4-1
source                  1..111
                        mol_type = protein
                        organism = synthetic construct
SEQUENCE: 128
DIVMTQSPDS LAVSLGERAT INCKSSESVD SYANSFLHWY QQKPGQPPKL LIYRASTRES        60
GVPDRFSGSG SGTDFTLTIS SLQAEDVAVY YCQQSKEDPL TFGGGTKVEI K                111

SEQ ID NO: 129          moltype = AA  length = 111
FEATURE                 Location/Qualifiers
REGION                  1..111
                        note = VL graft IGKV3-20
source                  1..111
                        mol_type = protein
                        organism = synthetic construct
SEQUENCE: 129
EIVLTQSPGT LSLSPGERAT LSCRASQSVD SYANSFLHWY QQKPGQAPRL LIYRASTRES        60
GIPDRFSGSG SGTDFTLTIS RLEPEDFAVY YCQQSKEDPL TFGGGTKVEI K                111

SEQ ID NO: 130          moltype = AA  length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 130
RASQSVDSYA NSFLA                                                       15

SEQ ID NO: 131          moltype = AA  length = 15
FEATURE                 Location/Qualifiers
REGION                  1..15
                        note = anti-C-MET antibody molecule or antigen-binding
```

```
                        portion LCDR1
source                  1..15
                        mol_type = protein
                        organism = synthetic construct
SEQUENCE: 131
RASQSVDSYA NSFLH                                                          15

SEQ ID NO: 132          moltype = AA  length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 132
RASQSVDSYA NSYLA                                                          15

SEQ ID NO: 133          moltype = AA  length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 133
RASQSVDSYA QSFLH                                                          15

SEQ ID NO: 134          moltype = AA  length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 134
RASQSVDSYA QSYLA                                                          15

SEQ ID NO: 135          moltype = AA  length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 135
RASQSVDSYA QSYLH                                                          15

SEQ ID NO: 136          moltype = AA  length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 136
RASQSVESYA NSFLA                                                          15

SEQ ID NO: 137          moltype = AA  length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 137
RASQSVESYA NSYLA                                                          15

SEQ ID NO: 138          moltype = AA  length = 15
FEATURE                 Location/Qualifiers
REGION                  1..15
                        note = anti-C-MET antibody molecule or antigen-binding
                         portion LCDR1
source                  1..15
```

```
                        mol_type = protein
                        organism = synthetic construct
SEQUENCE: 138
RASQSVESYA QSFLH                                                            15

SEQ ID NO: 139          moltype = AA   length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 139
RASQSVSSYA NSFLH                                                            15

SEQ ID NO: 140          moltype = AA   length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 140
RASQSVSSYA NSYLA                                                            15

SEQ ID NO: 141          moltype = AA   length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 141
RASQSVSSYA QSFLA                                                            15

SEQ ID NO: 142          moltype = AA   length = 15
FEATURE                 Location/Qualifiers
REGION                  1..15
                        note = anti-C-MET antibody molecule or antigen-binding
                         portion LCDR1
source                  1..15
                        mol_type = protein
                        organism = synthetic construct
SEQUENCE: 142
RASQSVSSYA QSFLH                                                            15

SEQ ID NO: 143          moltype = AA   length = 7
FEATURE                 Location/Qualifiers
REGION                  1..7
                        note = anti-C-MET antibody molecule or antigen-binding
                         portion LCDR2
source                  1..7
                        mol_type = protein
                        organism = synthetic construct
SEQUENCE: 143
AASTRES                                                                      7

SEQ ID NO: 144          moltype = AA   length = 7
FEATURE                 Location/Qualifiers
REGION                  1..7
                        note = anti-C-MET antibody molecule or antigen-binding
                         portion LCDR2
source                  1..7
                        mol_type = protein
                        organism = synthetic construct
SEQUENCE: 144
AGSTRES                                                                      7

SEQ ID NO: 145          moltype = AA   length = 7
FEATURE                 Location/Qualifiers
REGION                  1..7
                        note = anti-C-MET antibody molecule or antigen-binding
                         portion LCDR2
source                  1..7
                        mol_type = protein
                        organism = synthetic construct
```

```
SEQUENCE: 145
AGSTRET                                                                   7

SEQ ID NO: 146           moltype = AA  length = 7
FEATURE                  Location/Qualifiers
REGION                   1..7
                         note = anti-C-MET antibody molecule or antigen-binding
                          portion LCDR2
source                   1..7
                         mol_type = protein
                         organism = synthetic construct
SEQUENCE: 146
RASSRES                                                                   7

SEQ ID NO: 147           moltype = AA  length = 7
FEATURE                  Location/Qualifiers
REGION                   1..7
                         note = anti-C-MET antibody molecule or antigen-binding
                          portion LCDR2
source                   1..7
                         mol_type = protein
                         organism = synthetic construct
SEQUENCE: 147
RASSRET                                                                   7

SEQ ID NO: 148           moltype = AA  length = 7
FEATURE                  Location/Qualifiers
REGION                   1..7
                         note = anti-C-MET antibody molecule or antigen-binding
                          portion LCDR2
source                   1..7
                         mol_type = protein
                         organism = synthetic construct
SEQUENCE: 148
RGSSRES                                                                   7

SEQ ID NO: 149           moltype = AA  length = 7
FEATURE                  Location/Qualifiers
REGION                   1..7
                         note = anti-C-MET antibody molecule or antigen-binding
                          portion LCDR2
source                   1..7
                         mol_type = protein
                         organism = synthetic construct
SEQUENCE: 149
RGSSRET                                                                   7

SEQ ID NO: 150           moltype = AA  length = 10
FEATURE                  Location/Qualifiers
REGION                   1..10
                         note = anti-C-MET antibody molecule or antigen-binding
                          portion LCDR3
source                   1..10
                         mol_type = protein
                         organism = synthetic construct
SEQUENCE: 150
QQSGEDPLTF                                                               10

SEQ ID NO: 151           moltype = AA  length = 10
FEATURE                  Location/Qualifiers
REGION                   1..10
                         note = anti-C-MET antibody molecule or antigen-binding
                          portion LCDR3
source                   1..10
                         mol_type = protein
                         organism = synthetic construct
SEQUENCE: 151
QQSGEEPLTF                                                               10

SEQ ID NO: 152           moltype = AA  length = 10
FEATURE                  Location/Qualifiers
REGION                   1..10
                         note = anti-C-MET antibody molecule or antigen-binding
                          portion LCDR3
source                   1..10
                         mol_type = protein
                         organism = synthetic construct
SEQUENCE: 152
QQSGESPLTF                                                               10
```

```
SEQ ID NO: 153        moltype = AA  length = 10
FEATURE               Location/Qualifiers
REGION                1..10
                      note = anti-C-MET antibody molecule or antigen-binding
                       portion LCDR3
source                1..10
                      mol_type = protein
                      organism = synthetic construct
SEQUENCE: 153
QQSGSDPLTF                                                                10

SEQ ID NO: 154        moltype = AA  length = 10
FEATURE               Location/Qualifiers
REGION                1..10
                      note = anti-C-MET antibody molecule or antigen-binding
                       portion LCDR3
source                1..10
                      mol_type = protein
                      organism = synthetic construct
SEQUENCE: 154
QQSGSEPLTF                                                                10

SEQ ID NO: 155        moltype = AA  length = 10
FEATURE               Location/Qualifiers
REGION                1..10
                      note = anti-C-MET antibody molecule or antigen-binding
                       portion LCDR3
source                1..10
                      mol_type = protein
                      organism = synthetic construct
SEQUENCE: 155
QQSGSRPLTF                                                                10

SEQ ID NO: 156        moltype = AA  length = 10
FEATURE               Location/Qualifiers
REGION                1..10
                      note = anti-C-MET antibody molecule or antigen-binding
                       portion LCDR3
source                1..10
                      mol_type = protein
                      organism = synthetic construct
SEQUENCE: 156
QQSGSSPLTF                                                                10

SEQ ID NO: 157        moltype = AA  length = 10
FEATURE               Location/Qualifiers
REGION                1..10
                      note = anti-C-MET antibody molecule or antigen-binding
                       portion LCDR3
source                1..10
                      mol_type = protein
                      organism = synthetic construct
SEQUENCE: 157
QQSKEEPLTF                                                                10

SEQ ID NO: 158        moltype = AA  length = 10
FEATURE               Location/Qualifiers
REGION                1..10
                      note = anti-C-MET antibody molecule or antigen-binding
                       portion LCDR3
source                1..10
                      mol_type = protein
                      organism = synthetic construct
SEQUENCE: 158
QQSKESPLTF                                                                10

SEQ ID NO: 159        moltype = AA  length = 10
FEATURE               Location/Qualifiers
REGION                1..10
                      note = anti-C-MET antibody molecule or antigen-binding
                       portion LCDR3
source                1..10
                      mol_type = protein
                      organism = synthetic construct
SEQUENCE: 159
QQSKSDPLTF                                                                10

SEQ ID NO: 160        moltype = AA  length = 10
```

```
FEATURE                 Location/Qualifiers
REGION                  1..10
                        note = anti-C-MET antibody molecule or antigen-binding
                         portion LCDR3
source                  1..10
                        mol_type = protein
                        organism = synthetic construct
SEQUENCE: 160
QQSKSEPLTF                                                                    10

SEQ ID NO: 161          moltype = AA  length = 10
FEATURE                 Location/Qualifiers
REGION                  1..10
                        note = anti-C-MET antibody molecule or antigen-binding
                         portion LCDR3
source                  1..10
                        mol_type = protein
                        organism = synthetic construct
SEQUENCE: 161
QQSKSSPLTF                                                                    10

SEQ ID NO: 162          moltype = AA  length = 10
FEATURE                 Location/Qualifiers
REGION                  1..10
                        note = anti-C-MET antibody molecule or antigen-binding
                         portion LCDR3
source                  1..10
                        mol_type = protein
                        organism = synthetic construct
SEQUENCE: 162
QQYGSDPLTF                                                                    10

SEQ ID NO: 163          moltype = AA  length = 10
FEATURE                 Location/Qualifiers
REGION                  1..10
                        note = anti-C-MET antibody molecule or antigen-binding
                         portion LCDR3
source                  1..10
                        mol_type = protein
                        organism = synthetic construct
SEQUENCE: 163
QQYGSEPLTF                                                                    10

SEQ ID NO: 164          moltype = AA  length = 10
FEATURE                 Location/Qualifiers
REGION                  1..10
                        note = anti-C-MET antibody molecule or antigen-binding
                         portion LCDR3
source                  1..10
                        mol_type = protein
                        organism = synthetic construct
SEQUENCE: 164
QQYKEEPLTF                                                                    10

SEQ ID NO: 165          moltype = AA  length = 10
FEATURE                 Location/Qualifiers
REGION                  1..10
                        note = anti-C-MET antibody molecule or antigen-binding
                         portion LCDR3
source                  1..10
                        mol_type = protein
                        organism = synthetic construct
SEQUENCE: 165
QQYKESPLTF                                                                    10

SEQ ID NO: 166          moltype = AA  length = 10
FEATURE                 Location/Qualifiers
REGION                  1..10
                        note = anti-C-MET antibody molecule or antigen-binding
                         portion LCDR3
source                  1..10
                        mol_type = protein
                        organism = synthetic construct
SEQUENCE: 166
QQYKSDPLTF                                                                    10

SEQ ID NO: 167          moltype = AA  length = 10
FEATURE                 Location/Qualifiers
REGION                  1..10
```

```
                        note = anti-C-MET antibody molecule or antigen-binding
                         portion LCDR3
source                  1..10
                        mol_type = protein
                        organism = synthetic construct
SEQUENCE: 167
QQYKSSPLTF                                                                   10

SEQ ID NO: 168          moltype = AA  length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 168
GYIFTAYYMH                                                                   10

SEQ ID NO: 169          moltype = AA  length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 169
GYIFTSYYMH                                                                   10

SEQ ID NO: 170          moltype = AA  length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 170
GYTFTAYSMH                                                                   10

SEQ ID NO: 171          moltype = AA  length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 171
GYTFTAYTMH                                                                   10

SEQ ID NO: 172          moltype = AA  length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 172
GYTFTAYYMH                                                                   10

SEQ ID NO: 173          moltype = AA  length = 10
FEATURE                 Location/Qualifiers
REGION                  1..10
                        note = anti-C-MET antibody molecule or antigen-binding
                         portion HCDR1
source                  1..10
                        mol_type = protein
                        organism = synthetic construct
SEQUENCE: 173
GYTFTSYYMH                                                                   10

SEQ ID NO: 174          moltype = AA  length = 19
FEATURE                 Location/Qualifiers
REGION                  1..19
                        note = anti-C-MET antibody molecule or antigen-binding
                         portion HCDR2
```

```
source                  1..19
                        mol_type = protein
                        organism = synthetic construct
SEQUENCE: 174
MGIIKPNGGL ASYAQKFQG                                                    19

SEQ ID NO: 175          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 175
MGIIKPNGGS TSYAQKFQG                                                    19

SEQ ID NO: 176          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 176
MGIIKPNNGS TSYAQKFQG                                                    19

SEQ ID NO: 177          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 177
MGIIKPSNGS TSYAQKFQG                                                    19

SEQ ID NO: 178          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 178
MGIINPNNGS ASYAQKFQG                                                    19

SEQ ID NO: 179          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 179
MGIINPSGGL ANYAQKFQG                                                    19

SEQ ID NO: 180          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 180
MGIINPSGGS TNYAQKFQG                                                    19

SEQ ID NO: 181          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
```

```
                                    organism = synthetic construct
SEQUENCE: 181
MGWIKPNGGS TNYAQKFQG                                                      19

SEQ ID NO: 182          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 182
MGWIKPSGGS TSYAQKFQG                                                      19

SEQ ID NO: 183          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 183
MGWIKPSNGL ASYAQKFQG                                                      19

SEQ ID NO: 184          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 184
MGWIKPSNGS ANYAQKFQG                                                      19

SEQ ID NO: 185          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 185
MGWIKPSNGS ASYAQKFQG                                                      19

SEQ ID NO: 186          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 186
MGWIKPSNGS TSYAQKFQG                                                      19

SEQ ID NO: 187          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 187
MGWINPNGGL TSYAQKFQG                                                      19

SEQ ID NO: 188          moltype = AA   length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 188
```

```
MGWINPNNGL ANYAQKFQG                                              19

SEQ ID NO: 189         moltype = AA  length = 19
FEATURE                Location/Qualifiers
REGION                 1..19
                       note = anti-C-MET antibody molecule or antigen-binding
                        portion HCDR2
source                 1..19
                       mol_type = protein
                       organism = synthetic construct
SEQUENCE: 189
MGWINPNNGL ASYAQKFQG                                              19

SEQ ID NO: 190         moltype = AA  length = 19
FEATURE                Location/Qualifiers
REGION                 1..19
                       note = anti-C-MET antibody molecule or antigen-binding
                        portion HCDR2
source                 1..19
                       mol_type = protein
                       organism = synthetic construct
SEQUENCE: 190
MGWINPSGGL ASYAQKFQG                                              19

SEQ ID NO: 191         moltype = AA  length = 19
FEATURE                Location/Qualifiers
REGION                 1..19
                       note = anti-C-MET antibody molecule or antigen-binding
                        portion HCDR2
source                 1..19
                       mol_type = protein
                       organism = synthetic construct
SEQUENCE: 191
MGWINPSGGS ASYAQKFQG                                              19

SEQ ID NO: 192         moltype = AA  length = 19
FEATURE                Location/Qualifiers
REGION                 1..19
                       note = anti-C-MET antibody molecule or antigen-binding
                        portion HCDR2
source                 1..19
                       mol_type = protein
                       organism = synthetic construct
SEQUENCE: 192
MGWINPSNGL TNYAQKFQG                                              19

SEQ ID NO: 193         moltype = AA  length = 19
FEATURE                Location/Qualifiers
REGION                 1..19
                       note = anti-C-MET antibody molecule or antigen-binding
                        portion HCDR2
source                 1..19
                       mol_type = protein
                       organism = synthetic construct
SEQUENCE: 193
MGIIKPSGGS TNYAQKFQG                                              19

SEQ ID NO: 194         moltype = AA  length = 19
FEATURE                Location/Qualifiers
REGION                 1..19
                       note = anti-C-MET antibody molecule or antigen-binding
                        portion HCDR2
source                 1..19
                       mol_type = protein
                       organism = synthetic construct
SEQUENCE: 194
MGIIKPSNGL ASYAQKFQG                                              19

SEQ ID NO: 195         moltype = AA  length = 19
FEATURE                Location/Qualifiers
REGION                 1..19
                       note = anti-C-MET antibody molecule or antigen-binding
                        portion HCDR2
source                 1..19
                       mol_type = protein
                       organism = synthetic construct
SEQUENCE: 195
MGIINPNGGL TNYAQKFQG                                              19
```

```
SEQ ID NO: 196           moltype = AA  length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 196
MGIINPNGGL TSYAQKFQG                                                   19

SEQ ID NO: 197           moltype = AA  length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 197
MGIINPNGGS ANYAQKFQG                                                   19

SEQ ID NO: 198           moltype = AA  length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 198
MGIINPNGGS TNYAQKFQG                                                   19

SEQ ID NO: 199           moltype = AA  length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 199
MGIINPNNGL ASYAQKFQG                                                   19

SEQ ID NO: 200           moltype = AA  length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 200
MGIINPSGGS ASYAQKFQG                                                   19

SEQ ID NO: 201           moltype = AA  length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 201
MGIINPSNGL ANYAQKFQG                                                   19

SEQ ID NO: 202           moltype = AA  length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 202
MGIINPSNGL ASYAQKFQG                                                   19

SEQ ID NO: 203           moltype = AA  length = 19
FEATURE                  Location/Qualifiers
```

```
REGION                      1..19
                            note = anti-C-MET antibody molecule or antigen-binding
                             portion HCDR2
source                      1..19
                            mol_type = protein
                            organism = synthetic construct
SEQUENCE: 203
MGIINPSNGL TSYAQKFQG                                                        19

SEQ ID NO: 204              moltype = AA  length = 19
FEATURE                     Location/Qualifiers
REGION                      1..19
                            note = anti-C-MET antibody molecule or antigen-binding
                             portion HCDR2
source                      1..19
                            mol_type = protein
                            organism = synthetic construct
SEQUENCE: 204
MGIINPSNGS ANYAQKFQG                                                        19

SEQ ID NO: 205              moltype = AA  length = 19
FEATURE                     Location/Qualifiers
REGION                      1..19
                            note = anti-C-MET antibody molecule or antigen-binding
                             portion HCDR2
source                      1..19
                            mol_type = protein
                            organism = synthetic construct
SEQUENCE: 205
MGWIKPNGGL ANYAQKFQG                                                        19

SEQ ID NO: 206              moltype = AA  length = 19
FEATURE                     Location/Qualifiers
REGION                      1..19
                            note = anti-C-MET antibody molecule or antigen-binding
                             portion HCDR2
source                      1..19
                            mol_type = protein
                            organism = synthetic construct
SEQUENCE: 206
MGWIKPNGGS ASYAQKFQG                                                        19

SEQ ID NO: 207              moltype = AA  length = 19
FEATURE                     Location/Qualifiers
REGION                      1..19
                            note = anti-C-MET antibody molecule or antigen-binding
                             portion HCDR2
source                      1..19
                            mol_type = protein
                            organism = synthetic construct
SEQUENCE: 207
MGWIKPNGGS TSYAQKFQG                                                        19

SEQ ID NO: 208              moltype = AA  length = 19
FEATURE                     Location/Qualifiers
REGION                      1..19
                            note = anti-C-MET antibody molecule or antigen-binding
                             portion HCDR2
source                      1..19
                            mol_type = protein
                            organism = synthetic construct
SEQUENCE: 208
MGWIKPNNGS TSYAQKFQG                                                        19

SEQ ID NO: 209              moltype = AA  length = 19
FEATURE                     Location/Qualifiers
REGION                      1..19
                            note = anti-C-MET antibody molecule or antigen-binding
                             portion HCDR2
source                      1..19
                            mol_type = protein
                            organism = synthetic construct
SEQUENCE: 209
MGWINPNGGL TNYAQKFQG                                                        19

SEQ ID NO: 210              moltype = AA  length = 19
FEATURE                     Location/Qualifiers
REGION                      1..19
                            note = anti-C-MET antibody molecule or antigen-binding
```

```
                            portion HCDR2
source                      1..19
                            mol_type = protein
                            organism = synthetic construct
SEQUENCE: 210
MGWINPNGGS TNYAQKFQG                                                        19

SEQ ID NO: 211              moltype = AA  length = 19
FEATURE                     Location/Qualifiers
REGION                      1..19
                            note = anti-C-MET antibody molecule or antigen-binding
                            portion HCDR2
source                      1..19
                            mol_type = protein
                            organism = synthetic construct
SEQUENCE: 211
MGWINPNNGS TSYAQKFQG                                                        19

SEQ ID NO: 212              moltype = AA  length = 19
FEATURE                     Location/Qualifiers
REGION                      1..19
                            note = anti-C-MET antibody molecule or antigen-binding
                            portion HCDR2
source                      1..19
                            mol_type = protein
                            organism = synthetic construct
SEQUENCE: 212
MGWINPSGGL TSYAQKFQG                                                        19

SEQ ID NO: 213              moltype = AA  length = 19
FEATURE                     Location/Qualifiers
REGION                      1..19
                            note = anti-C-MET antibody molecule or antigen-binding
                            portion HCDR2
source                      1..19
                            mol_type = protein
                            organism = synthetic construct
SEQUENCE: 213
MGWINPSGGS ANYAQKFQG                                                        19

SEQ ID NO: 214              moltype = AA  length = 19
FEATURE                     Location/Qualifiers
REGION                      1..19
                            note = anti-C-MET antibody molecule or antigen-binding
                            portion HCDR2
source                      1..19
                            mol_type = protein
                            organism = synthetic construct
SEQUENCE: 214
MGWINPSGGS TNYAQKFQG                                                        19

SEQ ID NO: 215              moltype = AA  length = 19
FEATURE                     Location/Qualifiers
REGION                      1..19
                            note = anti-C-MET antibody molecule or antigen-binding
                            portion HCDR2
source                      1..19
                            mol_type = protein
                            organism = synthetic construct
SEQUENCE: 215
MGIIKPNGGS ANYAQKFQG                                                        19

SEQ ID NO: 216              moltype = AA  length = 19
FEATURE                     Location/Qualifiers
REGION                      1..19
                            note = anti-C-MET antibody molecule or antigen-binding
                            portion HCDR2
source                      1..19
                            mol_type = protein
                            organism = synthetic construct
SEQUENCE: 216
MGIIKPNNGS ASYAQKFQG                                                        19

SEQ ID NO: 217              moltype = AA  length = 19
FEATURE                     Location/Qualifiers
REGION                      1..19
                            note = anti-C-MET antibody molecule or antigen-binding
                            portion HCDR2
source                      1..19
```

```
                        mol_type = protein
                        organism = synthetic construct
SEQUENCE: 217
MGIIKPSGGL ANYAQKFQG                                                 19

SEQ ID NO: 218          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 218
MGIIKPSNGS ASYAQKFQG                                                 19

SEQ ID NO: 219          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 219
MGIINPNGGL ASYAQKFQG                                                 19

SEQ ID NO: 220          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 220
MGIINPNGGS ASYAQKFQG                                                 19

SEQ ID NO: 221          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 221
MGIINPNNGL ANYAQKFQG                                                 19

SEQ ID NO: 222          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 222
MGIINPSGGL ASYAQKFQG                                                 19

SEQ ID NO: 223          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 223
MGIINPSNGS TNYAQKFQG                                                 19

SEQ ID NO: 224          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
```

```
SEQUENCE: 224
MGIINPSNGS TSYAQKFQG                                                  19

SEQ ID NO: 225          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 225
MGWIKPNGGL TSYAQKFQG                                                  19

SEQ ID NO: 226          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 226
MGWIKPNNGL TSYAQKFQG                                                  19

SEQ ID NO: 227          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 227
MGWIKPNNGS ANYAQKFQG                                                  19

SEQ ID NO: 228          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 228
MGWIKPSGGL TSYAQKFQG                                                  19

SEQ ID NO: 229          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 229
MGWIKPSNGL TSYAQKFQG                                                  19

SEQ ID NO: 230          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 230
MGWIKPSNGS TNYAQKFQG                                                  19

SEQ ID NO: 231          moltype = AA  length = 19
FEATURE                 Location/Qualifiers
REGION                  1..19
                        note = anti-C-MET antibody molecule or antigen-binding
                         portion HCDR2
source                  1..19
                        mol_type = protein
                        organism = synthetic construct
SEQUENCE: 231
MGWINPNGGS ASYAQKFQG                                                  19
```

```
SEQ ID NO: 232           moltype = AA   length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 232
MGWINPNNGL TNYAQKFQG                                                    19

SEQ ID NO: 233           moltype = AA   length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 233
MGWINPNNGS ANYAQKFQG                                                    19

SEQ ID NO: 234           moltype = AA   length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 234
MGWINPNNGS ASYAQKFQG                                                    19

SEQ ID NO: 235           moltype = AA   length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 235
MGWINPSGGL TNYAQKFQG                                                    19

SEQ ID NO: 236           moltype = AA   length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 236
MGWINPSNGS ASYAQKFQG                                                    19

SEQ ID NO: 237           moltype = AA   length = 19
FEATURE                  Location/Qualifiers
REGION                   1..19
                         note = anti-C-MET antibody molecule or antigen-binding
                          portion HCDR2
source                   1..19
                         mol_type = protein
                         organism = synthetic construct
SEQUENCE: 237
MGWINPSNGS TSYAQKFQG                                                    19

SEQ ID NO: 238           moltype = AA   length = 9
FEATURE                  Location/Qualifiers
REGION                   1..9
                         note = anti-C-MET antibody molecule or antigen-binding
                          portion HCDR3
source                   1..9
                         mol_type = protein
                         organism = synthetic construct
SEQUENCE: 238
HEITTEFDY                                                                9

SEQ ID NO: 239           moltype = AA   length = 9
```

```
FEATURE              Location/Qualifiers
REGION               1..9
                     note = anti-C-MET antibody molecule or antigen-binding
                      portion HCDR3
source               1..9
                     mol_type = protein
                     organism = synthetic construct
SEQUENCE: 239
MEITTEFDY                                                                    9

SEQ ID NO: 240       moltype = AA  length = 9
FEATURE              Location/Qualifiers
REGION               1..9
                     note = anti-C-MET antibody molecule or antigen-binding
                      portion HCDR3
source               1..9
                     mol_type = protein
                     organism = synthetic construct
SEQUENCE: 240
QEITTELDY                                                                    9

SEQ ID NO: 241       moltype = AA  length = 9
FEATURE              Location/Qualifiers
REGION               1..9
                     note = anti-C-MET antibody molecule or antigen-binding
                      portion HCDR3
source               1..9
                     mol_type = protein
                     organism = synthetic construct
SEQUENCE: 241
SEITTEEDY                                                                    9

SEQ ID NO: 242       moltype = AA  length = 9
FEATURE              Location/Qualifiers
REGION               1..9
                     note = anti-C-MET antibody molecule or antigen-binding
                      portion HCDR3
source               1..9
                     mol_type = protein
                     organism = synthetic construct
SEQUENCE: 242
SEITTEFDA                                                                    9

SEQ ID NO: 243       moltype = AA  length = 9
FEATURE              Location/Qualifiers
REGION               1..9
                     note = anti-C-MET antibody molecule or antigen-binding
                      portion HCDR3
source               1..9
                     mol_type = protein
                     organism = synthetic construct
SEQUENCE: 243
SEITTEFDE                                                                    9

SEQ ID NO: 244       moltype = AA  length = 9
FEATURE              Location/Qualifiers
REGION               1..9
                     note = anti-C-MET antibody molecule or antigen-binding
                      portion HCDR3
source               1..9
                     mol_type = protein
                     organism = synthetic construct
SEQUENCE: 244
SEITTEFDF                                                                    9

SEQ ID NO: 245       moltype = AA  length = 9
FEATURE              Location/Qualifiers
REGION               1..9
                     note = anti-C-MET antibody molecule or antigen-binding
                      portion HCDR3
source               1..9
                     mol_type = protein
                     organism = synthetic construct
SEQUENCE: 245
SEITTEFDI                                                                    9

SEQ ID NO: 246       moltype = AA  length = 9
FEATURE              Location/Qualifiers
REGION               1..9
```

```
                        note = anti-C-MET antibody molecule or antigen-binding
                         portion HCDR3
source                  1..9
                        mol_type = protein
                        organism = synthetic construct
SEQUENCE: 246
SEITTEFDK                                                                    9

SEQ ID NO: 247          moltype = AA  length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 247
SEITTEFDL                                                                    9

SEQ ID NO: 248          moltype = AA  length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 248
SEITTEFDM                                                                    9

SEQ ID NO: 249          moltype = AA  length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 249
SEITTEFDQ                                                                    9

SEQ ID NO: 250          moltype = AA  length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 250
SEITTEFDS                                                                    9

SEQ ID NO: 251          moltype = AA  length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 251
SEITTEFDV                                                                    9

SEQ ID NO: 252          moltype = AA  length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 252
SEITTEFDW                                                                    9

SEQ ID NO: 253          moltype = AA  length = 9
FEATURE                 Location/Qualifiers
REGION                  1..9
                        note = anti-C-MET antibody molecule or antigen-binding
                         portion HCDR3
```

```
source                  1..9
                        mol_type = protein
                        organism = synthetic construct
SEQUENCE: 253
SEITTELDY                                                                          9

SEQ ID NO: 254          moltype = AA   length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 254
SEITTEWDY                                                                          9

SEQ ID NO: 255          moltype = AA   length = 9
FEATURE                 Location/Qualifiers
REGION                  1..9
                        note = anti-C-MET antibody molecule or antigen-binding
                         portion HCDR3
source                  1..9
                        mol_type = protein
                        organism = synthetic construct
SEQUENCE: 255
VEITTEFDL                                                                          9
```

The invention claimed is:

1. An anti-C-MET antibody or an antigen-binding portion thereof, wherein the antibody comprises a heavy chain variable (VH) region and a light chain variable (VL) region, wherein (a) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(b) the VH region amino acid sequence comprises HCDR1 of GYTFTSYTMH (SEQ ID NO: 34), HCDR2 of MGWINPSGGLANYAQKFQG (SEQ ID NO: 54) and HCDR3 of SEITTDFDY (SEQ ID NO: 55); and the VL region amino acid sequence comprises LCDR1 of RASQSVDSYANSYLH (SEQ ID NO: 51), LCDR2 of RGSTRES (LCDR2; SEQ ID NO: 38) and LCDR3 of QQSKSEPLT (SEQ ID NO: 39);

(c) the VH region amino acid sequence comprises HCDR1 of GYTFTSYTMH (SEQ ID NO: 34), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(d) the VH region amino acid sequence comprises HCDR1 of GYTFTSYAMH (SEQ ID NO: 41), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(e) the VH region amino acid sequence comprises HCDR1 of GYTFTSYTMH (SEQ ID NO: 34), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(f) the VH region amino acid sequence comprises HCDR1 of GYIFTSYSMH (SEQ ID NO: 43), HCDR2 of MGWINPSNGLANYAQKFQG (SEQ ID NO: 44) and HCDR3 of QEITTEFDI (SEQ ID NO: 45); and the VL region amino acid sequence comprises LCDR1 of RASQSVESYAQSYLH (SEQ ID NO: 46), LCDR2 of RGSTRES (SEQ ID NO: 38) and LCDR3 of QQSKSDPLT (SEQ ID NO: 76);

(g) the VH region amino acid sequence comprises HCDR1 of GYIFTSYTMH (SEQ ID NO: 48), HCDR2 of MGWINPNGGLASYAQKFQG (SEQ ID NO: 49) and HCDR3 of SEITTEQDY (SEQ ID NO: 50); and the VL region amino acid sequence comprises LCDR1 of RASQSVDSYANSYLH (SEQ ID NO: 51), LCDR2 of RGSTRES (SEQ ID NO: 38) and LCDR3 of QQSKESPLT (SEQ ID NO: 47); or (h) the VH region amino acid sequence comprises HCDR1 of GYIFTSYTMH (SEQ ID NO: 48), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVESYANSYLH (SEQ ID NO: 52), LCDR2 of RGSTRES (SEQ ID NO: 38) and LCDR3 of QQYGSEPLT (SEQ ID NO: 53).

2. The antibody or antigen-binding portion of claim 1, wherein (a) the VH region amino acid sequence comprises SEQ ID NO:7 and the VL region amino acid sequence comprises SEQ ID NO:8; or (b) the VH region amino acid sequence comprises SEQ ID NO:9 and the VL region amino acid sequence comprises SEQ ID NO:10.

3. The antibody or antigen-binding portion of claim 1, wherein the antibody is humanized or chimeric.

4. The antibody or antigen-binding portion of claim 1, wherein the VH region, the VL region, or both the VH and the VL region comprise one or more human framework region amino acid sequences.

5. The antibody or antigen-binding portion of claim 1, wherein the VH region, the VL region, or both the VH and the VL region comprise a human variable region framework scaffold amino acid sequence into which the CDRs have been inserted.

6. The antibody or antigen-binding portion of claim 1, wherein the VH region comprises an IGHV1-46 human germline scaffold amino acid sequence into which the HCDR1, HCDR2 and HCDR3 amino acid sequences have been inserted.

7. The antibody or antigen-binding portion of claim 1, wherein the VL region comprises an IGKV3-20 human germline scaffold amino acid sequence into which the LCDR1, LCDR2 and LCDR3 amino acid sequences have been inserted.

8. The antibody or antigen-binding portion of claim 1, wherein the antibody comprises an immunoglobulin constant region.

9. The antibody or antigen-binding portion of claim 8, wherein the immunoglobulin constant region is IgG, IgE, IgM, IgD, IgA or IgY.

10. The antibody or antigen-binding portion of claim 8, wherein the immunoglobulin constant region comprises any one of SEQ ID NOS: 11-17.

11. The antibody or antigen-binding portion of claim 1, wherein the antibody or antigen-binding portion is an Fab, an Fab', an F(ab')$_2$, an Fv, an scFv, a maxibody, a minibody, a diabody, a triabody, a tetrabody, or a bis-scFv.

12. The antibody or antigen-binding portion of claim 1, wherein the antibody is monoclonal.

13. The antibody or antigen-binding portion of claim 1, wherein the antibody is a tetrameric antibody, a tetravalent antibody or a multispecific antibody.

14. The antibody or antigen-binding portion of claim 1, wherein the antibody is a bispecific antibody that binds specifically to a first antigen and a second antigen, wherein the first antigen is C-MET and the second antigen is not C-MET.

15. The antibody or antigen-binding portion of claim 1, wherein the antibody or antigen-binding portion binds specifically to (a) human C-MET or (b) human C-MET and cynomolgus C-MET.

16. The antibody or antigen-binding portion of claim 1, wherein the antibody or antigen-binding portion is in a human IgG4 format comprising the amino acid substitution S228P, and wherein the antibody or antigen-binding portion has
 (a) a melting temperature (Tm) from about 77° C. to about 81° C.; and/or
 (b) an isoelectric point (pI) greater than about pH 7.4.

17. A pharmaceutical composition comprising the antibody or antigen-binding portion of claim 1, and a pharmaceutically acceptable carrier, diluent or excipient.

18. A nucleic acid molecule encoding
 (a) the VH region amino acid sequence;
 (b) the VL region amino acid sequence; or
 (c) both the VH and the VL region amino acid sequences of the antibody or antigen-binding portion of claim 1.

19. An expression vector comprising the nucleic acid molecule of claim 18.

* * * * *